(12) United States Patent
Gross et al.

(10) Patent No.: US 7,510,880 B2
(45) Date of Patent: *Mar. 31, 2009

(54) MULTIDIMENSIONAL MASS SPECTROMETRY OF SERUM AND CELLULAR LIPIDS DIRECTLY FROM BIOLOGIC EXTRACTS

(76) Inventors: Richard W. Gross, 307 Chesterfield Oaks, Chesterfield, MO (US) 63005; Xianlin Han, 427 N. Polo Dr., Clayton, MO (US) 63105

( * ) Notice: Subject to any disclaimer, the term of this patent is extended or adjusted under 35 U.S.C. 154(b) by 711 days.

This patent is subject to a terminal disclaimer.

(21) Appl. No.: 10/797,616

(22) Filed: Mar. 10, 2004

(65) Prior Publication Data

US 2004/0191916 A1 Sep. 30, 2004

Related U.S. Application Data

(63) Continuation-in-part of application No. 10/606,601, filed on Jun. 26, 2003, now Pat. No. 7,306,952.

(60) Provisional application No. 60/458,733, filed on Mar. 28, 2003, provisional application No. 60/391,711, filed on Jun. 26, 2002.

(51) Int. Cl.
*G01N 24/00* (2006.01)
*G01N 33/22* (2006.01)
*G01N 31/00* (2006.01)
*G01N 33/53* (2006.01)

(52) U.S. Cl. .................... 436/71; 436/13; 436/173; 436/811

(58) Field of Classification Search ............... 436/13, 436/71, 173, 811
See application file for complete search history.

(56) References Cited

OTHER PUBLICATIONS

Han et al., Proceedings of the National Academy of Sciences, vol. 91, pp. 10635-10639, 1994.*
Brugger et al., Proceedings of the National Academy of Sciences, vol. 94, pp. 2339-2344, 1997.*
Koivusalo et al, Journal of Lipid Research, vol. 42, pp. 663-672, 2001.*

* cited by examiner

*Primary Examiner*—Yelena G Gakh
*Assistant Examiner*—Keri A Moss
(74) *Attorney, Agent, or Firm*—Armstrong Teasdale LLP

(57) ABSTRACT

A method for determination of at least one of the lipid species in a biological sample comprising subjecting the sample to lipid extraction to obtain a lipid extract and subjecting the resulting lipid extract to multidimensional electrospray ionization mass spectrometry using either precursor ion or neutral loss scanning (or both) of all naturally occurring aliphatic chains, lipid fragments and precursor ions leading to observed fragments to generate a multidimensional matrix whose contour densities provides structural and quantitative information directly without chromatography. A method for determination of lipid content and/or lipid molecular species composition and quantity directly from lipid extracts of a biological sample comprising subjecting said lipid extract to electrospray ionization multidimensional mass spectrometry by comparisons to standards and algorithms described herein.

20 Claims, 22 Drawing Sheets

MULTIDIMENSIONAL MASS SPECTROMETRY OF SERUM AND CELLULAR LIPIDS DIRECTLY FROM BIOLOGIC EXTRACTS

CROSS REFERENCE TO RELATED APPLICATION

This application is a continuation in part of pending U.S. nonprovisional patent application Ser. No. 10/606,601, filed Jun. 26, 2003 now U.S. Pat. No. 7,306,952 which claims priority to U.S. provisional patent application 60/391,711 filed Jun. 26, 2002, and claims the benefit of U.S. provisional patent application 60/458,733 filed Mar. 28, 2003 all of which are incorporated by reference in their entirety.

STATEMENT REGARDING FEDERALLY SPONSORED RESEARCH & DEVELOPMENT

This work was supported by grants from NIH including grants W/H P01 HL57278/JDFI 996003, R02HL41250, RO1 AA11094, P41-RR00954, P60-DK20579, and P30-DK56341. The government has certain rights in the invention.

FIELD OF THE INVENTION

This invention relates generally to a method of analysis for lipids including triglycerides and other mentioned cellular lipids in a biological sample. More particularly this invention relates to a method for analysis and individual molecular species quantification of triglycerides and other cellular lipids in a biological sample.

This invention also relates to the fingerprinting detection, diagnosis and treatment of triglycerides and other cellular lipids in blood, vessels, atheroma, liver, stool and other body tissues as well as biopsies of body organs such as a liver or a muscle biopsy.

This invention also relates to a method of determining the risk to an individual of TG molecular species as an independent factor in the development of coronary artery disease, stroke, atherosclerosis and obesity as well as to target agents to selectively modify triglyceride (hereinafter "TG") molecular species.

This invention also relates to the fingerprinting, detection, diagnosis and treatment of triglycerides in blood, liver, stool, sputum and other body tissues as well as biopsies of body organs such as a liver or a muscle biopsy. Also this invention relates to a method of screening drugs to determine those lipid modulating drugs which are efficacious in clinical trials and to monitor the response of patients to a specific drug therapy to determine the best or optimum drug for each patient.

BACKGROUND OF THE INVENTION

Triglycerides comprise linear combinations of aliphatic chains covalently attached to a glycerol backbone. Triglycerides serve as vital sources of cellular energy and caloric potential in living organisms. Recent work has provided unambiguous evidence of the importance of total triglycerides as a lipid class to the development of heart disease, stroke, obesity and diabetes in humans all of which are life taking diseases which take a staggering toll of human lives each year. Additionally, such afflictions destroy or significantly reduce the quality of life even if not immediately fatal.

Triglycerides (TG) includes molecules of glycerol esterified with three fatty acids. TG have a glycerol backbone structure while the associated fatty acids are predominately unsaturated. Dihydroxyacetone phosphate (DHAP) or glycerophosphate produced during glycolysis is the precursor for triacylglycerol synthesis (Triacylglycerides are triglycerides) in mammalian cells including adipocytes and hepatocytes.

In mammals, complex and diverse mechanisms have evolved to regulate the TG content in serum, the delivery of fatty acids derived from serum TG molecular species to cells (e.g., lipoprotein lipase and fatty acid transport protein), and the intracellular storage of fatty acids by esterification to a glycerol backbone for subsequent storage as TG molecular species. It is highly desired to be able to readily determine the identity of TG molecular species along with their respective quantity present in biological samples including living mammalian and plant samples. In many such areas of research and medical therapy it is desired and necessary to analyze large and increasing numbers of biological samples in an enhanced fashion such as those samples comprising TG molecular species.

For at least the aforegoing reasons biological analytical methods which readily and directly identify and quantify TG molecular species in biological samples will be an integral and vital part of research which produces discoveries of benefit to mankind in the biochemistry of plants and animals dealing with coronary artery disease, stroke, atherosclerosis and obesity. Accordingly an enhanced analysis of such biological samples is needed which provides a TG molecular species profile.

The TG molecular species profile reflects the nutritional and metabolic history of each cell as well as its anticipated energy storage requirements. Alterations in TG molecular species synthesis and catabolism have been demonstrated to play prominent roles in obesity, atherosclerosis, insulin release from pancreatic β cells, and alcohol-induced hepatic dysfunction (1-7). Moreover, recent studies have identified the importance of alterations in intracellular triglycerides as a potential mediator of diabetic cardiomyopathy (5,8).

Although some studies have measured total TG molecular species content in multiple different disease states, a paucity of information on TG molecular species changes during pathophysiological alterations is available. The first detailed molecular species analyses of TG in diabetic rat myocardium demonstrated a dramatic alteration in TG molecular species composition without substantial changes in TG mass (8). Accordingly, it seems likely that changes in TG molecular species composition also contributes to the pathophysiological sequelae of other disease states.

Previous attempts at direct TG quantitation by positive-ion electrospray ionization mass spectrometry (ESI/MS) were undesirably confounded by the presence of overlapping peaks from choline glycerophospholipids requiring chromatographic separation of lipid extracts prior to ESI/MS analyses. Thus it is highly desired to have an enhanced method and system for determining TG content in various living mammalian and plant cellular systems which obviates the chromatographic separation process requirement. Moreover, isobaric molecular species present in all biological tissues prevent determination of individual molecular species of triglycerides from molecular weight determinations alone.

BRIEF DESCRIPTION OF THE INVENTION

In a first embodiment, a method for the determination of lipid such as TG individual (i.e. separate) molecular species composition of matter in a biological sample comprises subjecting the biological sample to lipid extraction to obtain a lipid extract and subjecting the lipid extract to electrospray ionization tandem mass spectrometry (ESI/MS/MS) providing lipid such as TG molecular species composition as a useful output determination.

Lipids are essential cellular constituents that have multiple distinct yet critical roles in cellular function. Lipids provide an impermeable barrier which separate intracellular and extracellular compartments without which life and self-renewal would be impossible. Moreover, lipids concurrently provide a matrix for the appropriate interactions of membrane-associated proteins to interact with each other as well as promote interactions of membrane proteins with cognate intra- and extracellular binding partners. Finally biologic membranes serve as storage reservoirs for biologically active 2nd messengers (eicosanoids, diglycerides, ceramides, etc.) that allow each cell to effectively respond to internal and external stimuli. Biologic membranes fulfill these multiple functions through the synthesis of multiple distinct covalent entities each with its unique structural and physical characteristics. The inherent chemical diversity present in biologic lipids is achieved through multiple discrete covalent assemblies of lipid backbone (typically glycerol) with linear combinations of various aliphatic chains (typically 14-22 carbons long containing variable amounts of unsaturation). This biologic diversity facilitates the specific tailoring of individual cellular responses to alterations in cellular nutrient status, metabolic history and signaling events. Accordingly, many groups have rigorously pursued the identification of alterations in cellular lipid constituents to identify the chemical mechanisms underlying such diverse diseases as obesity, atherosclerosis and lipotoxicity now endemic in industrialized populations.

The precise complement of chemically distinct covalent entities in cellular lipids has been referred to as the cellular lipidome. Research in lipidomics incorporates multiple different techniques to first quantify the precise chemical constituents present in the cellular lipidome, determine their subcellular organization (subcellular membrane compartments and microdomains) and delineate lipid-lipid and lipid-protein conformational space and dynamics. Through these methods, the role of lipids in biologic processes can ultimately be determined. The first step in global lipidomics is to obtain a detailed account of the precise chemical entities (i.e. composition of matter) present in a cell's lipidome and identify alterations that precipitate, or are associated with, phenotypic alterations after cellular perturbation.

In an aspect, a method for the determination of lipid such as TG individual (i.e. separate) molecular species composition of matter directly from a lipid extract of a biological sample comprises subjecting the lipid extract to electrospray ionization tandem mass spectrometry using neutral loss scanning and two dimensional (or multidimensional) density contour analysis.

In an aspect, neutral loss scanning is used with electrospray ionization tandem mass spectrometry.

In an aspect, at least one of lipid and TG content is obtained by summing and obtaining the total of the TG individual (i.e. separate) molecular species.

In an aspect, the inventive concept comprises analyzing a biological sample using electrospray ionization tandem mass spectrometry (ESI/MS/MS) and performing a two dimensional (or multidimensional) analysis with cross peak contour analysis on the output of the ESI/MS/MS to provide a fingerprint of at least one of lipid or triglyceride individual (i.e. separate) molecular species.

In an aspect, lipid such as (TG) content is obtained by summing and obtaining the total of the lipid or TG individual (i.e. separate) molecular species.

In an aspect, a diagnostic kit for the determination of triglyceride molecular species in a biological sample comprises components suitable for carrying out at least one of a method for the determination of triglyceride (TG) content and/or molecular species composition of matter in a mammalian and plant biological sample comprises subjecting said biological sample to lipid extraction to obtain a lipid extract and subjecting the lipid extract to electrospray ionization tandem mass spectrometry (ESI/MS/MS) using neutral loss scanning providing as output the TG content and a method for the determination of triglyceride content and/or molecular species directly from a lipid extract of a biological sample comprising subjecting the lipid extract to electrospray ionization tandem mass spectrometry using neutral loss scanning.

In an aspect, the kit is housed in a container.

In an aspect, a method for assessing a risk to each (individual) subject (or group of individuals) based on lipid including TG molecular species as an independent factor in the development of at least one condition in that individual for a medical condition selected from coronary artery disease, stroke, atherosclerosis and obesity which comprises analyzing a biological sample of an individual for TG molecular species determination, administering of a drug to the individual, analyzing a corresponding biological sample of said administered to treated individual for TG molecular species determination, comparing the TG molecular species determination after drug administration with the TG molecular species determination prior to drug administration and determining a risk therefrom associated with that individual. In an aspect, the comparison of the TG molecular species determination of the biological samples is predictive of the likelihood of development of the condition for that subject and its prevention by tailored drug therapy.

In an aspect, the comparison is indicative of a predisposition of an individual to develop a condition. In an aspect, the condition is a desirable condition. In an aspect the condition is an undesirable condition. In an aspect, the condition is a medical condition which is desirable or undesirable. In an aspect, a desirable medical condition is a lowered triglyceride content of a human's blood.

In an aspect, a method for determining an agent which selectively targets lipid i.e. triglyceride molecular species (e.g., saturated triglycerides) comprises analyzing a biological sample of at least one individual for TG molecular species determination, administering a therapeutic amount of a drug to the individual, analyzing a biological sample of said administered individual for TG molecular species determination, comparing the TG molecular species determination after said administration with the TG molecular species determination prior to the drug administration and determining an effect if any on the individual of the drug administration. In an aspect, the comparison of the TG molecular species determination of the biological samples is indicative of development of the condition for that (treated) individual.

In an aspect, a method of identifying a candidate lipid modulating drug having lipid modulating drug efficacy comprises selecting a biological sample to be taken, analyzing a biological sample of at least one individual for lipid i.e. TG molecular species determination, administering of a candidate lipid modulating drug to the individual, analyzing a biological sample of treated individual, comparing the TG molecular species determination after said administration with the TG molecular species determination prior to the drug administration and determining an effect on the individual of the drug administration. In an aspect, the comparison of TG analysis is indicative of the efficacy a lipid modulating capacity of an administered drug.

In an aspect, a method to diagnose and determine the response of patients to tailored drug therapy comprises analyzing a biological sample taken of at least one individual for lipid i.e. TG molecular species determination, administering a drug to the patient (hereinafter treated patient), analyzing a biological sample taken of the treated patient for TG molecular species determination, comparing the TG molecular species determination after the administration with the TG molecular species determination prior to the drug administration and determining an effect on the individual of the drug administration. In an aspect, the comparison of TG molecular species determination (analysis) is indicative of the efficacy a tailored drug therapy. In several aspects, the effect comprises a positive effect, a negative effect and no effect.

In an aspect, a method of screening candidate chemicals for lipid modulating potential in a subject comprises analyzing a biological sample of at least one individual for lipid i.e. TG molecular species determination, administering a therapeutic amount of a drug to that biological subject, analyzing a biological sample taken from the administered to subject for TG molecular species determination, comparing the TG molecular species determination after said administration with the TG molecular species determination prior to the drug administration and determining an effect if any on the subject of the drug administration. In an aspect, the comparison of TG analysis is indicative of the efficacy a candidate chemical having a lipid modulating potential.

In an aspect, a method of treating a subject comprises analyzing a biological sample taken of that subject for lipid i.e. TG molecular species determination by a method comprising ESI/MS/MS with neutral loss scanning and two dimensional (or multidimensional) contour analysis. In an aspect, the subject is human.

In an another aspect, a medical treatment comprises analyzing a biological sample taken of a subject for lipid i.e. TG molecular analysis by ESI/MS/MS. In an aspect the medical treatment is for a human.

In an aspect, a method of customizing drug therapy for a subject comprises analyzing a biological sample taken of the subject for lipid i.e. TG molecular species determination by ESI/MS/MS and adjusting the subject's drug therapy based on the results of the TG molecular species determination. In an aspect, the subject is human.

In an aspect, a method of retarding, preventing, and ameliorating disease or a medical affliction in a subject comprises analyzing a biological sample taken of a subject for TG molecular analysis by ESI/MS/MS with neutral loss scanning and prescribing a therapy for the subject based on that TG molecular species determination. In an aspect, the subject is human.

In an aspect, a method is provided to identify and quantify multiple lipid species concurrently directly from their lipid extracts of biologic samples through intrasource separation and multidimensional analysis of mass spectra from precursor ion and neutral loss scans of naturally occurring lipid fragments.

In an aspect, multidimensional analysis of samples which are subject to derivatizations to those skilled in the art such as derivatization of primary amines (aldehydes and other agents), double bonds (dimethyldisulfide, diborane or other common reagents), sugars, phosphates, primary hydroxyl (trimethylsilysl chloride) and other common derivatizing agents.

In an aspect, a ratiometric comparison of lipids between two states (e.g., control and disease) is carried out by derivatization with light and heavy isotopes to determine the relative amounts of each molecular species after multidimensional mass spectrometric analysis by these methods.

In an aspect, a method for identification of biomarkers of disease, prognostic indicators of disease outcome or markers of treatment efficacy in disease states which can be identified through multidimensional mass spectrometry by a systems biology bioinformatics approach which is provided by correlating the mass of lipid products and met6abolites with disease onset, severity or progression.

In an aspect, this methodology of this discovery encompasses a method for an automated platform for multidimensional lipid analysis capable of analyzing thousands of different lipids through multidimensional mass spectrometry through commonly employed principles of automation (e.g., automated sample injection) and data analysis (e.g., deisotope deconvolution) as routinely employed by those skilled in the field.

In an aspect, this discovery of a multidimensional mass spectrometry provides a means for obtaining abundant novel chemical information about spatial relationships in lipid molecules (e.g., regiospecificity, chemical linkages and relative abundance of isobaric and other species) not accessible by the one dimensional approach.

In an aspect, a method for determination of at least one of the lipid species in a biological sample comprising subjecting the sample to lipid extraction to obtain a lipid extract and subjecting the resulting lipid extract to multidimensional electrospray ionization mass spectrometry using either precursor ion or neutral loss scanning (or both) of all naturally occurring aliphatic chains, lipid fragments and precursor ions leading to observed fragments to generate a multidimensional matrix whose contour densities provides structural and quantitative information directly without chromatography. A method for determination of lipid content and/or lipid molecular species composition and quantity directly from lipid extracts of a biological sample comprising subjecting said lipid extract to electrospray ionization multidimensional mass spectrometry by comparisons to standards and algorithms described herein.

BRIEF DESCRIPTION OF THE DRAWINGS

More in detail, FIGS. 1A and 1B depict positive-ion electrospray ionization mass spectrum of an equimolar mixture of triaglycerides. FIG. 1A depicts an ESI/MS analysis of an equimolar mixture of twelve species of TG. FIG. 1B depicts an ESI/MS of six triglyceride species.

FIGS. 2A and 2B depict a relationship of ESI/MS relative peak intensities with TG molecular species concentration.

FIGS. 3A and 3B depict positive-ion electro spray ionization tandem mass spectra of triglyceride molecular species in the product ion mode. FIG. 3(A) depicts an ESI tandem mass spectrum of lithiated 16:0/18:1/20:4 TG. FIG. 3B depicts an ESI tandem mass spectrum of lithiated 18:1/20:4/18:1 TG.

FIG. 4 depicts a positive-ion electrospray ionization mass spectrum and tandem mass spectra of an equimolar mixture of triglycerides by neutral loss scanning.

FIG. 5 depicts a positive-ion electrospray ionization mass spectrum and neutral loss mass spectra of lipid extracts from rat myocardium.

DETAILED DESCRIPTION OF THE INVENTION

Figure 1:
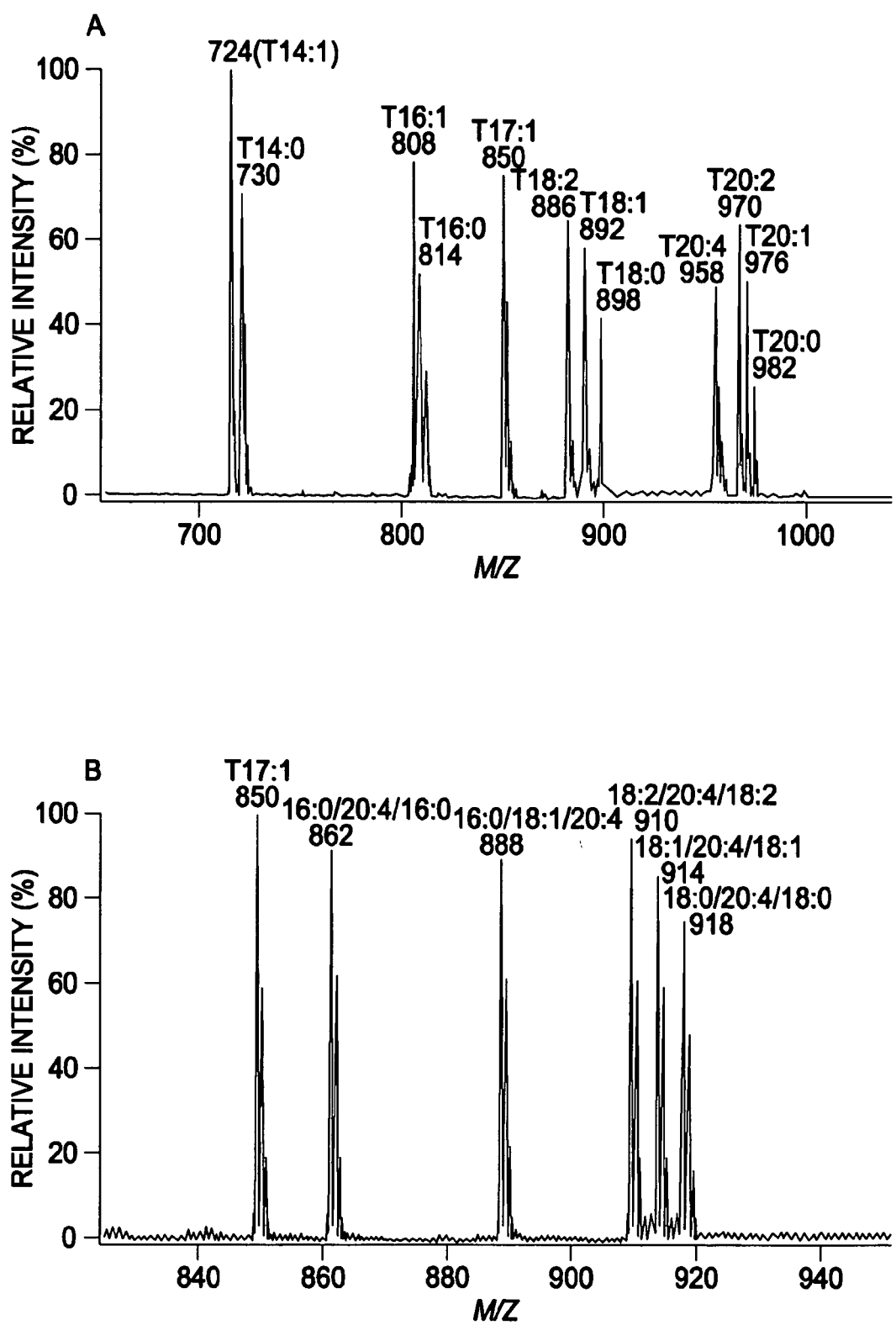
FIGS. 1A and 1B, FIGS. 2A and 2B, FIGS. 3A and 3B and FIGS. 4-5 depict analytical results of tests conducted using the inventive ESI/MS/MS process herein.

The present invention is understood more readily by reference to the following detailed description of the invention and the Example included therein.

Before the present method and kit are disclosed and described, it is to be understood that this invention is not limited to specific apparatus or to a specific method. It is also to be understood that the terminology used herein is for the purpose of describing particular embodiments only and is not intended to be limiting.

It must be noted that, as used in the specification the singular forms "a," "an," and "the" include plural referents unless the context clearly dictates otherwise.

In an aspect, the term "patient" includes subject and individual. In an aspect, the patient includes a living human, feline, canine, horses and murine.

In an aspect, the invention comprises a rapid, simple, and reliable method for the quantitative analysis and molecular species fingerprinting of triglycerides (TG) directly from chloroform extracts of biological samples.

The term "Multidimensional" spectra, as it is referred to in this present application, comprises the organized collection of primary ion manipulations through multiplexed neutral loss fragmentations and/or precursor ion scannings to collectively generate a n-dimensional matrix (i.e., multidimensional spectra). Examples of dimensions include head groups, aliphatic chains, all derivatized moieties which together contains a complete set, or nearly complete set of information which can structurally identify each of the primary ions class, subclass and molecular species distributions, deconvolute isobaric molecular species and provide the enabling technology for construction of an automated platform for lipid analysis identifying class assignments, aliphatic chain length compositions and composition of isobaric species. Moreover, through judicious use of bioinformatics weighting algorithms the matrices described herein facilitates molecular species quantitation directly from a biologic extract by multidimensional scanning by the methods described herein which segregates each primary ion peak into a resolvable set of densities whose form and content in each dimension can be used for identification of each primary ion's structure, isobaric species composition, and through the combined sets of precursor ion scans and neutral scans (multidimensions) in conjunction with bioinformatics approaches can be used for quantitation through appropriately referenced internal standards in each dimension by ratiometric comparisons.

In an aspect, a method for the determination of triglyceride (TG) content and/or molecular species composition of matter in a mammalian and plant biological sample comprises subjecting said biological sample to lipid extraction to obtain a lipid extract and subjecting the lipid extract to electrospray ionization tandem mass spectrometry (ESI/MS/MS) providing the TG mass and individual molecular species content as an output.

In an aspect, a biological sample comprises a sample taken of at least one of blood, vessels, atheroma, liver, stool and other body tissues as well as biopsies of body organs such as a liver biopsy or a muscle biopsy.

As used here, the term "contour analysis" is an analysis based on the shape or periphery of the outline of data, such as external periphery on a 2 dimensional drawing. In an aspect, a contour is presented in some Figures of this application.

In an aspect, the inventive method provides for mass accuracy of detecting and quantifying specific components of a biological sample via a systematic toxicological analysis using a mass spectrometer/mass spectrometer herein after referred to as a tandem mass spectrometer.

In an aspect, the term "deconvulution" includes the use of appropriate deconvuluting algorithms which provide for a systematic procedure for removing noise, extraneous signals and haze from output of a device such as from the output of an ESI/MS/MS. In an aspect, an illustrative useful deconvolution method is present in the Examples. Use of the deconvolution algorithms provides a deconvoluted determination.

In an aspect, the inventive methodology comprises a total analysis of triglyceride individual composition of matter of each triglyceride molecular species of each triglyceride molecular species in a biologic sample through a high throughput procedure.

Briefly, the inventive methods present a novel multidimensional such as a two-dimensional approach/method which quantitates individual molecular species of triglycerides by two dimensional (or multidimensional) electrospray ionization mass spectroscopy with neutral loss scanning. This method provides a facile way to fingerprint each patient's (or biologic sample's) triglyceride composition of matter (individual molecular species content) directly from chloroform extracts of biologic samples. Through selective ionization and subsequent deconvolution of 2D (or multidimensional ESI/MS) intercept density contours of the pseudomolecular parent ions and their neutral loss products, the individual molecular species of triglycerides can be determined directly from chloroform extracts of biological material. This 2D (or multidimensional ESI/MS) (two dimensional (or multidimensional)) approach comprises a novel enhanced successful functional therapy model for the automated determination and global fingerprinting of each patient's serum or cellular triglyceride content thus providing the facile determination of detailed aspects of lipid metabolism underlying disease states and their response to diet, exercise or drug therapy.

In an aspect of this inventive method, we employ tandem mass spectroscopic separation of specific lipid class-reagent ion pairs is used in conjunction with contour density deconvolution of cross peaks resulting from neutral losses of aliphatic chains to determine the individual triglyceride molecular species from a biological sample (blood, liver, muscle, feces, urine, tissue biopsy, or rat myocardium.).

As used herein the term "tandem mass spectrometer" includes a functional analytical instrument having the technical capability to capably measure the mass of molecules, identify those molecules and provide such identifying information in digitized or hard copy output format.

As used herein the term "fingerprinting" includes a biological sample analysis including quantification and qualification of the numbers and types of TG molecular species present in a biological (biologic) analyzed sample. In an aspect, the sample is a biological sample form a mammal or a plant.

In an aspect, a TG molecular species determination comprises a determination of at least one TG in a biological sample. In an aspect, the TG molecular species determination comprises the determination of 2, 3, 4, 5, 6, 7, 8, 9, 10 TG molecular species in a biological sample.

As used herein, the term "triglycerides", denoted symbolically as TG, includes the alpha and beta forms, multiple beta' and beta forms, single, multiple and mixed acyl triglycerides and triglyceride mixtures and includes compounds having three glycerol residues (e.g. cardiolipin). TG includes molecules of glycerol esterified with three fatty acids and corresponding ether or oxidized molecular species. As used herein, the term "acyl" refers to an organic acid group in which the —OH of the carboxyl group is replaced by some other substituent. Useful non-limiting TG include compounds in which three aliphatic chains are linked to a glycerol independently with ester, ether, and/or vinyl ether linkage.

As used herein the term "TG molecular species profile" includes the relative and actual distribution of TG molecular species composition of matter in a biological sample such as in a mammalian or plant living cell having a genome.

Abbreviations used herein include DAG, diacylglyceride; DMAP, N,N-dimethyl-4-aminopyridine; Dm:n DAD, di m:n glyceride; ESI, electrospray ionization; FA, fatty acid; MS/MS tandem mass spectrometry; m:n, fatty acyl chain containing m carbons and n double bonds; NL, neutral loss; TG, tracyglycerides; Tm:n TG and tri m:n glyceride.

As used herein, the term "m" represents an integer in the range from about 1 to about 22. As used herein the term "n" independently of m represents an integer from about 0 to about 6 such as independently integers 1, 2, 3, 4, 5 and 6.

As used herein, the term "biological sample" includes a sample of a suitable size such as a sample of size and composition suitable to a TG analysis of biological matter. In an aspect the biological sample includes serum, blood, urine, mammalian and human bodily fluid and a cell, such as a mammalian cell or a recombinant cell, a native or modified mammalian cell In an aspect, bodily fluid comprises a solid, semi-solid, liquid or semi-liquid mass exiting or excreted from the human body.

As used herein the term "mass spectrometer" includes and is synonymous with the term mass analyzer and may be used interchangeably herein.

In an aspect a biological sample comprises a composition comprising TG which is nonantagonistically accommodating to a TG analysis using ESI and tandem mass spectrometry.

As used herein the term "agent" includes atoms, cells and molecules.

As used herein, the term "normalization" include a method where peaks or numbers of an output are proportionally calculated or plotted to a selected peak or number which is generally arbitrarily assigned a value such as 1 or 100.

As used herein, the term "TAG" throughout the specification and claims includes lipids such as triglycerides and is intended to include other lipid classes subject to analysis by the multidimensional ESI methods described herein including, but not limited to, phospholipids (e.g., choline) glycerophospholipides (e.g., plasmenycholine, phosphatidylcholine, plasmanylcholine), sphingomeyelin, ethanolamine glycerophospholipids, mono and dimethyl ethanolamine, glycerophospholipds, serine glycerophospholipids, inositol glycerophospholipids, cardiolipin, phosphatidic acid, phosphatidylglycerol, phasphatidylethanol and oxidized derivatives thereof), fatty acids, fatty amides, eicosanoids, sphingolipids, glycolipids, steroids, ceramides, acylCoA, acylcamitine, acylprotiens, acylpeptides, diglycerides, monoglycerides, anadamide and 2-arachidonyl glycerol. Further, the description provided herein with regards to TAG applies to lipids as aforementioned in all regards including in the claims.

In an aspect one mass analyzer is connected to another sequentially coupled mass analyzer mechanically by an interpositioned chamber (the chamber referred to as a collision cell or chamber) that can break a molecule undergoing analysis and emitted by the first mass analyzer into two or more component parts. In an aspect a tandem mass spectrometer comprises first and second sequentially coupled mass analyzers. The biological sample is a sample representative of a portion of the subject such as of a human, wherein the result of having a TG analysis presents a meaningful point of medical research or treatment to one taking or having the biological sample taken and analyzed. In another aspect a tandem mass spectrometer comprises a first, second and third sequentially coupled mass analyzers.

Advantageously, tandem mass spectrometry (MS/MS) is accurate and specific in its identification of TG individual molecular species. Tandem mass spectrometry analyzes small amounts of biological sample and provides a multicomponent analysis simultaneously or nearly simultaneously of a biological sample in an elapsed analysis time of about two to three minutes or so.

In an aspect the weight of a biological sample is at a minimum of tissue about 1 mg, of cells about 2,000, and of blood about 2 µl or comparable functionally adequate amounts, quantities or volumes of other biologic samples. In an aspect, the amount of biological sample is that amount or volume which is sufficient to provide for an analysis.

In an aspect, a biological sample is processed in tandem mass spectrometer a first mass spectrometer set up in a tandem arrangement with another mass spectrometer. In that regard the biological sample can be considered as sorted and weighed in the first mass spectrometer, then broken into parts in an inter-mass spectrometer collision cell, and a part or parts of the biological sample are thereafter sorted and weighed in the second mass spectrometer thereby providing a mass spectrometric output readily and directly useable from the tandem mass spectrometer.

In an aspect, the output of the tandem mass spectrometer which is TG molecular species determination, is presented visually and optionally and can be recorded on a recorder output. Typically the tandem mass spectrometer output is shown or displayed visually as an abscissa and ordinate graph having ordinate lines spread across an abscissa at a right angle to each other such as on a display or graphic surface visible to the eye. This organized display output is a mass spectrum. The point at which the vertical line occurs in the spectrum is the place which identifies a compound's mass while the height of that vertical line associated with the analyzed compound represents the amount of the compound present in the biological sample fed to the mass spectrometer. Typically, the biological sample is fed by hand or robotics to the ESI/tandem mass spectrometer.

In analysis, a sample is generally taken of the subject to be analyzed. In an aspect, the sample is part of, or the entire subject to be analyzed. In an aspect a subject to be sampled comprises a plant. In another aspect the subject comprises an animal such as a human, porcine, feline, equistrine and murine, a part or portion thereof.

If desired, samples can be prepared by chromatography or other purification methods as well, prior to analysis with electrospray ionization tandem mass spectrometry (ESI/MS/MS).

In an aspect, a pre-analysis separation comprises a separation of lipoproteins prior to lipid extraction. In an aspect, the pre-analysis separation comprises at least one operation or process which is useful to provide an enhanced biological sample to the electrospray ionization tandem mass spectrometry (ESI/MS/MS). In an aspect, a pre-analysis separation is performed on a biological sample and two compositions are prepared accordingly from the biological sample. In an aspect one composition comprises high density lipoproteins and another composition comprises low density lipoproteins.

Generally, a biological sample taken is representative of the subject from which or of which the sample is taken so that an analysis of the sample is representative of the subject. In an aspect a representative number of samples are taken and analyzed of a subject such that a recognized and accepted statistical analysis indicates that the analytic results are statistically valid. Typically the composition is aqueous based and contains proteinaceous matter along with triglycerides. For example, a human blood sample is sometimes used. Through use of this inventive method, a plasma sample can be analyzed and appropriate information from the plasma can be extracted in a few minutes. Alternatively, information can be taken from the cells in the blood as well.

In an aspect, serum is utilized as a biological sample. After whole blood is removed from a human body and the blood clots outside the body, blood cells and some of the proteins become solid leaving a residual liquid which is serum.

In an aspect a control sample is employed in the analysis.

In an aspect, the biological sample or a representative aliquot or portion thereof is subjected to lipid extraction to obtain a lipid extract suitable for ESI/MS/MS. In an aspect lipids are extracted from the sample which in an aspect contains a tissue matrix. Non-lipid contaminants should be removed from the lipid extract.

In one aspect lipid extraction is carried by the known lipid extraction process of Folch as well as by the known lipid extraction process of Bligh and Dyer. These useful lipid extraction process are described in Christie, W. W. Preparation of lipid extracts from tissues. In: Advances in Lipid Methodology—Two, pp. 195-213 (1993) (edited by W. W. Christie, Oily Press, Dundee) EXTRACTION OF LIPIDS FROM SAMPLES William W. Christie The Scottish Crop Research Institute, Invergowrie, Dundee DD2 5DA, Scotland all of which are incorporated herein in their entirety by reference. The useful Folch extraction process is reported at Folch et al., J Biol Chem 1957, 226, 497 which is incorporated herein in its entirety by reference.

Generally, lipid extraction is carried out very soon in time on the tissue matrix or immediately after removal (harvest) of tissues (tissue matrix) from humanely sacrificed organisms which have been living (carried out using and following acceptable animal welfare protocols). Alternatively, tissues are stored in such a way that they are conservatively preserved for future use. In an aspect, a lipid extract is provided and used to produce ionized atoms and molecules in the inventive analytical method as feed to the ESI n our novel analysis method.

In an aspect a chloroform lipid extract is employed as a lipid extract composition fed to the ESI. The effluent from the ESI is fed to the tandem mass spectrometer (i.e. from the exit of the ESI).

In an aspect, a Freezer Mill 6800 from Fisher Bioblock Scientific is used to finely pulverize soft or hard harvested tissues of a biological sample in one or two minutes in liquid nitrogen to render the tissue sufficiently pliable and porous for lipid extraction. Alternatively, the pulverization of the harvested tissue is carried out by subjecting the harvested tissue to hand directed mashing and pulverization using a hand directed stainless-steel mortar and pestle. In a further aspect, an enzymatic digestion is carried out on the harvested tissue which is harvested from a preserved cadaver.

In an aspect, lipids are contained in the lipid extract following the lipid extraction. Generally the extraction is a suitable liquid/liquid or liquid/solid extraction whereby the TG are contained in the extract. In an aspect the extractant has sufficient solvating capability power and solvating capacity so as to solvate a substantial portion of the TG therein or substantially all of the TG present in the biological sample and is contained in the lipid extract.

In an aspect, chloroform is employed as an extractant to produce a useful lipid extract. Other useful extractants include but are not limited to those extractants which have a solvating power, capability and efficiency substantially that of chloroform with regard to the TG molecular species.

The inventive process creates charged forms of very high molecular weight TG molecules obtained via lipid extraction of a biological sample as a part of the process of detecting and analyzing biological samples containing TG.

In an aspect, in order to detect for and analyze ionized atoms and molecules such as TG molecular species in a biological sample, the lipid extract of that biological sample is used to produce ionized atoms and molecules by an ionization method such as electrospray ionization (ESI). As used herein, the term ESI includes both conventional and pneumatically-assisted electrospray.

In use, the inventive procedure operates by producing droplets of a sample composition by pneumatic nebulization which compresses and forces a biological sample composition containing TG such as an analyte containing TG into a proximal end of a mechanical means housing or holding a fine sized orifice such as a needle or capillary exiting at the distal end of the orifice at which there is applied a sufficient potential. Generally the orifice is a very small bore full length orifice having an internal average diameter or bore in the range from about 0.2 to about 0.5 mm.

In an aspect formation of a suitable spray is a critical operating parameter in ESI. Suitable solvent removable filters may be used to remove undesired solvents in the biological sample composition prior to being fed to the ESI. Generally high concentrations of electrolytes are avoided in samples fed to ESI.

The composition of materials of the means housing or holding the orifice and the orifice are compatible with the compositions of the biological sample to be processed through the orifice. Metallic and composition plastic compositions may be employed. In an aspect the orifice is a capillary or has a conical or capillary shape. In another aspect the orifice is cone shaped with the exterior converging from the proximate end to the distal end.

In an aspect the biologic sample is forced through the orifice by application of air pressure to the sample at the proximate end of the orifice or the sample is forced through the orifice or capillary by the application of vacuum at the distal end of the orifice. The net result is that ions are suitably formed at atmospheric pressure and progress through the cone shaped orifice. In an aspect the orifice is a first vacuum stage and the ions undergo free jet expansion. A collector at the distal end of the orifice collects the ions and guides the ions to a tandem mass spectrometer (MS/MS).

As used herein, the terms biologic samples and biological sample are synonymous with regard to one another and are used interchangeably.

In an aspect a suitable potential is applied via a field to the sample composition discharged from or at the distal end of the orifice. This potential is sufficiently high so that it capably and effectively converts the composition exiting the distal end of the orifice into a fine spay of droplets all at the same or substantially the same potential. See http://methods.ch.com.ac.uk/meth/ms/theory/esi.html for a description of ESI which is incorporated herein by reference in its entirety. The potential is in the range from about 3 to about 5 kv (kv is kilovolts).

ESI is followed by tandem mass spectrometry (MS/MS) which is an analytical method to separate and measure charge to mass ratios (M/Z) of ionized molecules and/or atoms. See http://nanogenesys.maxbizcenter.comm/new2183.html. In an aspect a tandem mass spectrometer is utilized which quantifies the amounts of individual ionized atoms or molecules and as noted in the above web site provides detailed information on structure of molecules of the sample undergoing analysis therein.

In another aspect, ESI useful herein is also described at http://chm.bris.ac.uk/omsf/interface.html wherein a sample solution is described as being sprayed across a highly protected diffuser of a few kilovolts from a needle into an orifice in an interface. Thereafter according to that web site (The NERC Organic Mass Spectrometry Facility) heat and gas fumes are used to desolvate ions in the sample solution undergoing ESI.

In an aspect, a tandem mass spectrometer is employed and is fed the biologic sample affluent from the ESI. The tandem mass spectrometer is an instrument that detects molecules by measuring their weight (mass). Mass spectrometers measure weight electronically and display output analytical results in the form of a mass spectrum. In an aspect, mass spectrum is the readable and visual output of a mass spectrometer a.e., a graph, in digital or hard copy form that shows each specific molecule by weight and how much of each molecule is present in the sample which was fed to the tandem mass spectrometer for analysis therein.

In an aspect collision activated dissociation is employed in preparing the feed composition (i.e. sample from the ESD) to the tandem mass spectrometer. A useful reference on tandem mass spectrometry is Mass Spectrometry/Mass Spectrometry: Techniques and Applications of Tandem Mass Spectrometry, Busch, K. L., Glish, G. L., McLuckey, S. A., ISBN: -471-18699-6, Hardcover, January 1989. This reference is incorporated herein by reference in its entirety.

In an aspect, the ESI/MS/MS is powered by 110 volt electrical supply. To turn on, a user connects the ESI/MS/MS to an electric power supply and turns on the appropriate electrical switches providing current to the ESI/MS/MS.

In an aspect, tandem mass spectrometry provides the needed specificity and selectivity for analysis of TG molecular species including trace analysis in complex biological samples including complex tissue analysis of such biological samples comprising TG.

Advantageously, the inventive methods herein comprise an unexpected but successful translation of an enhanced analytical procedure comprising ESI/MS/MS for TG molecular species determination of a biological sample providing high throughput global fingerprinting of each patient's serum or cellular triglyceride molecular species facilitate or optimize medicinal therapies for subjects.

In an aspect, deconvolution is carried out by applying any useful and acceptable deconvolution algorithm to the output of the ESI/MS/MS providing as a result a deconvoluted data output product.

In an aspect, data is normalized by applying a mathematically and statistically useful and acceptable normalization technique to deconvoluted data output product providing as a result normalized data output.

In an aspect, appropriate computer software and hardware is provided and is programmed to provide appropriate deconvolution and normalization as aforedescribed using appropriate devonvolution and optionally normalization algorithms.

The following Examples are presented merely to further illustrate and explain the present invention and should not be taken as limiting the invention in any regard.

EXAMPLES

The present invention is more particularly described in the following Examples which are intended as illustrative only since numerous modifications and variations therein will be apparent to those skilled in the art. All weights and ratios used herein are on a weight basis unless otherwise specified.

Materials and Methods

A. Materials Obtained and Sources

In this Example, triglycerides (TG) were employed as illustrative TG.

All triglycerides containing three homogeneous acyl chains including tritetradecanoin (T14:0 TG), tritetradecenoin (T14:1 TG), trihexadecanoin (T16:0 TG), trihexadecenoin (T16:1 TG), triheptadecenoin (T17:1 TG), trioctadecanoin (T18:0 TG), trioctadecenoin ($\Delta 9$ cis) (T18:1 TG), trioctadecadienoin ($\Delta 9$, 12 cis) (T18:2 TG), trieicosanoin (T20:0 TG), trieicosenoin ($\Delta 11$ cis) (T20:1 TG), trieicosadienenoin ($\Delta 11$, 14 cis) (T20:2 TG), and trieicosatetraenoin ($\Delta 5$, 8, 11, 14 cis) (T20:4 TG) and all 1,3-diacylglycerides (DAG) containing two homogeneous acyl chains including dihexadecanoin (D16:0 DAG), dioctadecanoin (D18:0 DAG), diotadecenoin ($\Delta 9$ cis) (D18:1 DAG), and dioctadecadienoin ($\Delta 9$, 12 cis) (D18:2 DAG) were purchased from Nu Chek Prep, Inc. P.O. Box 295, Elysian, Minn. 56028. All TG molecular species containing mixed acyl chains including 1-octadec-9'-enoyl-2,3-dihexadecanoyl-rac-glycerol (18:2/16:0/16:0 TG), 1-octadecanoyl-2,3-dihexadecanoyl-rac-glycerol (18:0/16:0/16:0 TG), 1-hexadecanoyl-2-octadecanoyl-3-hexadecanoyl-rac-glycerol (16:0/18:0/16:0 TG), 1-hexadecanoyl-2-octadex-9'-enoyl-3-octadecanoyl-racglycerol (16:0/18:1/18:0 TG), 1-hexadecanoyl-2-octadecanoyl-3-octadec-9'-enoyl-3-octadecanoyl-rac-glycerol (16:0/18:1/18:0 TG), 1-hexadecanoyl-2-octadecanoyl-3-octadec-9'-enoyl-rac-glycerol (16.0/18:0/18:1 TG), and 1,2-octadec-9'-enoyl-3-octadecanoyl-rac-glycerol (18:1/18:1/18:0 TG) were obtained from Matreya, Inc. (2011 Pine Hall Drive, State College, Pa. 16803, also in Pleasant Gap, Pa.). 1-Hexadecanoyl-2-octadec-9'-enoyl-sn-glycerol (16:0/18:1 DAG) were purchased from Avanti Polar Lipids, Inc. (700 Industrial Park Drive, Alabaster, Ala.).

Synthetic heptadecanoyl ceramide (N17:0 ceramide) and phospholipids including 1,2-dimyristoleoyl-sn-glycero-3-phosphocholine (14:1-14:1 PtdCho), 1,2-dipentadecanoyl-sn-glycero-3-phosphoethanolamine (15:0-15:0 PtdEtn), 1,2-dipentadecanoyl-sn-glycero-3-phosphoglycerol (15:0-15:0 PtdGro), 1,2-dimyristoyl-sn-glycero-3-phosphoserine (14:0-14:0 PtdSer), and 1-heptadecanoyl-2-hydroxyl-sn-glycero-3-phosphocholine (17:0 lysoPtdCho) were purchased from Avanti Polar Lipids, Inc. (Alabaster, Ala., USA).

The purity of all TG (commercial and synthetic) was determined by ESI/MS prior to use in quantitative analyses. All solvents were HPLC grade (or higher) and were obtained from Fisher Scientific (Pittsburgh, Pa.). Reagents were of analytical grade and were purchased from Sigma-Aldrich 2909 Laclede St. Louis, Mo. 63103.

B. Synthesis and Purification of TG Molecular Species Containing Arachidonoyl Constituents The reaction procedure was performed in a dry nitrogen atmosphere at 22° C. and care was taken to minimize exposure of the reaction vessel to light. Ten milligrams of each individual DAG molecular specie[D16:0 DAG, D18:0 DAG, D18:1 DAG, D18:2 DAG, and 16:0/18:1 DAG, stored in chloroform/methanol (2/1, v/v)] was dried under a nitrogen stream. Dried DAGs and recrystallized N,N-dimethyl-4-aminopyridine (DMAP) were further individually dried under high vacuum overnight in the presence of phosphorus pentoxide. Each individual DAG molecular species was dissolved in 1 mL of freshly distilled chloroform in a 5-mL conical vial prior to the addition of 3 mg of re-crystallized DMAP in solid. Next, 15 mg of arachidonoyl chloride (previously dissolved in 1 mL of distilled chloroform) was added dropwise to the reaction vessel over 10 min with constant stirring. The reaction mixture was stirred for an additional 30 min prior to termination by addition of distilled water and subsequent Bligh and Dyer extraction.

Synthetic arachidonoyl-containing TG molecular species were purified by TLC (silica LK6D plates, Whatman) employing a mobile phase comprised of petroleum ether/ethyl ether/acetic acid (80/20/1 v/v/v). The band on the TLC plate corresponding to TG molecular species, which was recognized by comparison to a TG standard spotted on the side of the same plate, was scraped, the silica powder was loaded onto a pre-rinsed Sep-Pak silica column, and TG molecular species were eluted utilizing 10 mL of chloroform. Purified arachidonoyl-containing TG molecular species were quantitated by capillary gas chromatography after acid methanolysis utilizing arachidonic acid (20:0) as an internal standard (23).

C. Preparation of the Mixtures of TG Molecular Species

A stock solution of each TG molecular species in chloroform was quantitatively prepared and stored under nitrogen at −20° C. The TG solutions were brought to room temperature (or 25° C.) just prior to utilization. Mixtures of TG molecular species were prepared from these stock solutions using gas-tight syringes. The concentration of each TG molecular species in the mixtures was ranged from 1 to 1000 nM. Since sodium ions could complicate the ESI mass spectra of TG and interfere with the quantitative analyses of TG molecular species, all the mixed solutions were extracted by a modified Bligh and Dyer technique (24) utilizing 50 mM LiOH in an aqueous layer to minimize the presence of sodium ion in the solutions. The extracts were dried under a nitrogen stream, dissolved in chloroform, filtered with 0.2 μm Gelman acrodisc CR PTFE syringe filters (Gelman Science, Ann Arbor, Mich.), and dried under a nitrogen stream. The final residues of TG mixtures were resuspended in 0.2 mL of 1:1 chloroform/methanol for ESI/MS analyses.

D. Preparation of Lipid Extracts from Rat Tissues

Male Sprague-Dawley rats (a universally used, widely accepted and general purpose research model rat of about 350-450 grams body weight) were purchased from Charles River Laboratories, Inc. (251 Ballardvale Street Wilmington, Mass. 01887-1000) and humanely sacrificed according to accepted animal welfare protocols.

The Sprague-Dawley rat hearts were excised quickly and immersed in ice-cold buffer (250 mM sucrose/25 mM imidazole, pH 8.0, at 4° C.). After removing extraneous tissue and epicardial fat, each heart tissue was blotted to remove excess buffer and immediately freeze-clamped at the temperature of liquid nitrogen. Myocardial wafers were pulverized into a fine powder with a stainless-steel mortar and pestle. A protein assay was performed on homogenized myocardial wafers and data were normalized to the protein content of the rat heart tissues. A ~30 mg myocardial wafer was weighed from each harvested rat heart and lipids were extracted by a modified Bligh and Dyer technique (24) utilizing 50 mM LiOH in an aqueous layer in the presence of T17:1 TG (150 pmol/mg of protein; used as an internal standard for TG quantification). This molecular species of endogenous TG represents <1% of lipid mass. ESI mass spectra from control experiments in which the internal standard was not exogenously added were also taken to ensure the absence of any demonstrable endogenous molecular ions in that region. The lipid extracts were dried under a nitrogen stream, dissolved in chloroform, desalted with Sep-Pak columns, filtered with 0.2 μm Gelman acrodisc CR PTFE syringe filters (Gelman Science), reextracted, and dried under a nitrogen stream. The final lipid residue was resuspended in 0.2 mL of 1:1 chloroform/methanl for ESI/MS analyses.

Male mice (4 month of age) were purchased from The Jackson Laboratory (Bar Harbor, Me., USA). Mice were sacrificed by inhalation of carbon dioxide prior to tissue collection. Each mouse liver was collected and washed in 20 ml of PBS twice. Then half of the liver was cut into small pieces followed by homogenization in 2 ml of ice-cold LiCl solution (50 mM) by using a Potter-Elvehjem tissue grinder. Protein concentration of homogenates were then determined using a bicinchoninic acid protein assay kit (Pierce, Rockford, Ill., USA) using bovine serum albumin as a standard. A small volume of homogenate containing 2 to 5 mg of protein was transferred to a glass test tube. Methanol and chloroform (2 ml of each) as well as additional volume of LiCl solution to make a solution of 1.8 ml with a final LiCl solution of 50 mM were added to the test tube containing the liver homogenate for lipid extraction by the Bligh and Dyer procedure (13).

At this point, internal standards including 14:0-14:0 PtdSer (1.0 nmol/mg protein), 15:0-15:0 PtdGro (4.2 nmol/mg protein), 15:0-15:0 PtdEtn (18.75 nmol/mg protein), 14:1-14:1 PtdCho (15 nmol/mg protein), 17:0 lysoPtdCho (1 nmol/mg protein), N17:0 ceramide (40 pmol/mg protein), T17:1 TAG (10 nmol/mg protein), and 20:0 FA (2 nmol/mg protein) were added to each homogenate based on protein concentration.

Thus, the quantified lipid content can be normalized to the protein content. These internal standards were selected because they only represent <<1% of endogenous cellular lipid mass as demonstrated by ESI/MS lipid analysis without addition of these internal standards. The selected set of internal standards represent the minimal number of internal standards necessary for lipid quantitation. If much higher accuracy for quantitation is desired, one internal standard for each class of lipids is recommended, or if the focus of the study is on a single lipid class even multiple internal standards for each class of lipids can be employed [14-16].

Next, the extraction mixture was centrifuged at 2,500 rpm for 10 min. The chloroform layer was carefully removed and saved. Into the MeOH and aqueous layer of each test tube, an additional 2 ml of chloroform was added and chloroform layer was separated as above. The chloroform extracts from each identical sample were combined and dried under a nitrogen stream. Each individual residue was then resuspended in 4 ml of chloroform/methanol (1:1), re-extracted against 1.8 ml of 20 mM LiCl aqueous solution, and the extract was dried as described above. Each individual residue was resuspended in ~1 ml of chloroform and filtered with a 0.2-µm PFTE syringe filter into a 5-ml glass centrifuge tube (this step was repeated twice). The chloroform solution was subsequently dried under a nitrogen stream and each individual residue was resuspended with a volume of 500 µl/mg of protein in 1:1 chloroform/methanol. The lipid extracts were finally flushed with nitrogen, capped, and stored at −20° C. for ESI/MS analyses (typically within one week). Each lipid solution has to be further diluted approximately 50 fold just prior to infusion and lipid analysis in negative-ion mode (Experimental condition 1 in FIG. 1). This diluted lipid solution contains approximately 4 pmol/µl of total lipids. To this diluted lipid solution, LiOH (50 nmol/mg of protein) was added just prior to performing further lipid analyses in both negative- and positive-ion modes (Experimental conditions 2 and 3, respectively, in FIG. 6).

E. Electrospray Ionization Mass Spectrometry of Triglycerides (TG)

ESI mass spectral analyses of TG molecular species were performed similarly to the analyses of phospholipids utilizing a Finnigan TSQ-7000 spectrometer equipped with an electrospray ion source as described previously (25, 26). (Thermo Finnigan, Global Headquarters, 355 Fiver Oaks Parkway, San Jose, Calif. 95134-1991 USA).

Typically, a 5-min period of signal averaging in the profile mode was employed for each (mass spectrum)s of a TG sample or lipid extract. All samples were appropriately diluted in 1:1 chloroform/methanol prior to direct infusion into the ESI chamber using a syringe pump at a flow rate of 1 µL/min. TG molecular species were directly ionized in the positive-ion mode by ESI. Tandem mass spectrometry of TG after electrospray ionization of TG after electrospray ionization was performed by collisional activation with argon gas. The resultant product ions were analyzed after passage into the third quadrupole. The degree of collisional activation as adjusted through variation of the cd offset voltage and collision gas pressure. During this study, a collision energy of 35 eV and collision gas pressure of 2.5 mTorr were used. Two types of tandem mass spectrometric analyses were employed (i.e., product-ion scanning and neutral loss scanning). Product-ion tandem mass spectrometry was conducted similarly as described previously (27). Tandem mass spectrometry utilizing neutral losses were performed through the simultaneous scanning of both the first and third quadrupoles at a fixed different mass (i.e., neutral loss) corresponding to the mass of the fatty acids of interest.

TG molecular species were directly quantitated by comparisons of ion peak intensities with that of internal standard (i.e., T17:1 TG) after correction for C isotope effects in the positive-ion mode. Two types of $^{13}$C isotope effects were considered. First, correction for the effect from the carbon number difference between a given TG molecular species and the internal standard was calculated as follows:

$$Z_1=(1+0.011n+0.011^2n(n-1)/2)/(1+0.011s+0.011^2s(s-1)/2)=0.5648+6.213\times10^{-3}n+3.417\times10^{-5}n^2, \quad [1]$$

where $Z_1$ is a type I $^{13}$C isotope correction factor, n is the total carbon number in the molecular species of interest, and s is the total carbon number of internal standard, and s is 54 for T17:1 TG. n is in the range from about 0 to about 6.

The degree of type I isotope correction is less than 10% in most cases. The second type of $^{13}$C isotope effect comes from the overlapping of the M+2 isotope peak with the molecular ion peak of a species, which has a 2-Da higher mass. The general correction factor for this type of $^{13}$C isotope effect is as follows:

$$Z_2=1-(I_{m-2}/I_m)0.011^2m(m-1)/2=1-6.05\times10^{-5}m^2(I_{M-2}/I_M), \quad [2]$$

where $Z_2$ is a type II $^{13}$C isotope correction factor, m is the total carbon number in the molecular species with lower molecular mass, and m ranges from about 30 to about 70 and $I_{M-1}$ and $I_M$ are peak intensities of ions at molecular weight (M−2) and M, respectively.

As used herein, the alphabetical symbols m, n, s represent integers which vary independently of each other and may be the same or different. As used herein, "C" means carbon 13 isotope. Deisotope approach of al lipids are included.

Protein concentration was determined with a bicinchoninic acid protein assay kit (Pierce Biotechnology, Inc., P.O. Box 117, Rockford, Ill., 61105) using bovine serum albumin as a standard. Quantitative data from biological samples were normalized to the protein content of the tissues and all data are presented as means ±SEM of a minimum of three independent preparations.

A triple-quadrupole mass spectrometer (ThermoFinnigan TSQ Quantum, San Jose, Calif., USA) operating under Xcalibur software was utilized in the study. The first and third quadrupoles served as independent mass analyzers while the second quadrupole served as a collision cell for tandem mass spectrometry. The spray voltage was maintained at +3.6 kV in positive-ion mode and −3.6 kV in the negative-ion mode. An offset voltage on the ion transfer capillary was set to 17 V and −17 V in the positive- and negative-ion modes, respectively. The heater temperature along the ion transfer capillary was maintained at 350° C. The sheath gas (nitrogen) pressure was 2 psi. The diluted lipid extract solution was directly infused into the ESI source at a flow rate of 2 µl/min with a syringe pump using an orthogonal injection. Typically, a 1-min period of signal averaging in the profile mode was employed for each MS spectrum. Under these condition, we have demonstrated that an ion peak of any anionic phospholipid molecular species with S/N=10 could be readily obtained from 1 fmol of sample consumed (Spectra not shown).

For tandem mass spectrometry, a collision gas pressure was set at 1.0 mTorr but the collision energy was varied with the classes of lipids as follows: neutral loss scanning for ceramides in negative-ion mode, 34 eV; neutral loss scanning of fatty acids in both PtdCho and TAG species as well as precursor ion scanning of 183.1 amu (phosphocholine) for PtdCho in positive-ion mode, 35 eV; precursor-ion scanning at m/z for acyl carboxylate anions in PtdEtn, chlorinated PtdCho, and anionic phospholipids in negative-ion mode, 28 eV; neutral loss of 87.0 amu (serine) for PtdSer in negative-ion mode, 28 eV; neutral loss of 50.0 amu ($CH_3Cl$) for chlorinated PtdCho in negative-ion mode, 23.5 eV; precursor-ion scanning of m/z 241.1 (inositol phosphate) for PtdIns in negative-ion mode, 38 eV, and precursor-ion scanning of m/z 153.0 (phosphate derivative) for anionic phospholipids in negative-ion mode, 35 eV. Typically, a 2-min period of signal averaging in the profile mode was employed for each tandem MS spectrum.

F. Results—Detailed Description of the Drawings

G. (FIGS. 1A and 1B, FIGS. 2A and 2B, FIGS. 3A and 3B, FIGS. 4-5, FIGS. 6-7, FIGS. 8A and 8B, FIGS. 9A and 9B, FIGS. 10A and 10B, FIGS. 11-12, FIGS. 13A and 13B and 13C, FIG. 14, FIGS. 15A and 15B and FIG. 16 Depict Analytical Results of Tests Run using the Inventive ESI/MS/MS Process Herein.)

FIG. 1 depicts positive-ion electrospary ionization mass spectrum of an equimolar mixture of triglycerides. Equimolar mixtures of 12 triglyceride molecular species (i.e., T14:1, T14:0, T16:1, T16:0, T17:1, T18:2, T18:1, T20:4, T20:2, T20:1, and T20:0, 10 nM each in a total volume of 200 μL) (A) or 6 triglyceride molecular species (i.e., 16:0/20:4/16:0, 16:0/18:1/20:4, 18:2/20:4/18:2 18:1/20:4/18:1, 18:0/20:4/ 18:0, and T17:1 TG, 10 nM each in a total volume of 200 μL) (B) were prepared from stock solutions and extracted by a modified Bligh-Dyer method in the presence of 50 nM LiOH in the acqueous phase as described herein under Materials and Methods.

The solutions of TG mixtures in chloroform/methanol (1:1, by volume) were directly infused into the ESI ion source using a Harvard syringe pump at a flow rate of 1 μL/min. Mass spectrometry of triglycerides was performed as previously described under Materials and Methods. Molecular ions in the mass spectra have been labeled with masses corresponding to their lithiated TG molecular species adducts. The masses of all ion peaks are rounded to the nearest integer.

FIG. 2 depicts relationship of ESI/MS/relative peak intensities with TG molecular species concentration. In A, mixtures of TG molecular species containing identical molar ratios, but different concentrations, of individual TG components were prepared as described under Materials and Methods. Positive-ion ESI mass spectra were acquired as described in the legend to FIG. 1. The lithiated molecular ion peaks of each individual TG molecular species were quantified relative to the internal standard (T17:1 TG) after corrections were made for $^{13}C$ isotope effects. Experiments were performed over a three-order magnitude of concentration range (1 to 1000 nM) in mixtures containing T14:1 TG (□), T16:1 TG (◇), T18:1 TG (o), or T20:1 TG (Δ). In B, samples were prepared containing different molar ratio relative to the internal standard (T17:1) and the intensity of the molecular ion was quantified by ESI/MS after corrections for $^{13}C$ isotope effects. The ratios of molecular ion intensities of T14:1 TG (□), T16:1 TG (◇), T18:1 TG (o), or T20:1 TG (Δ) with the molar ratio in the prepared solutions had coefficients ($\delta^2$)>0.99. The slope for each individual TG molecular species was defined as the correction factor for the sensitivity effect relative to T17:1 TG. Data are presented as a means ±SEM from at least four separate sample presentations.

FIG. 3 depicts positive-ion electrospray ionization tandem mass spectra of triglyceride molecular species in the production mode. (A) ESI tandem mass spectrum of lithiated 16:0/ 18:1/20:4 TG. (B) ESI tandem mass spectrum of lithiated 18:1/20:4/18:1 TG. Samples of the TG mixture were prepared and ESI/MS was performed as described in the legend to FIG. 1. After selection of the lithiated pseudo-molecular ion of TG molecular species in the first quadrupole, collision activation was performed in the second quadrupole and the resultant product ions were analyzed in the third quadrupole as described under Materials and Methods.

Figure 4:
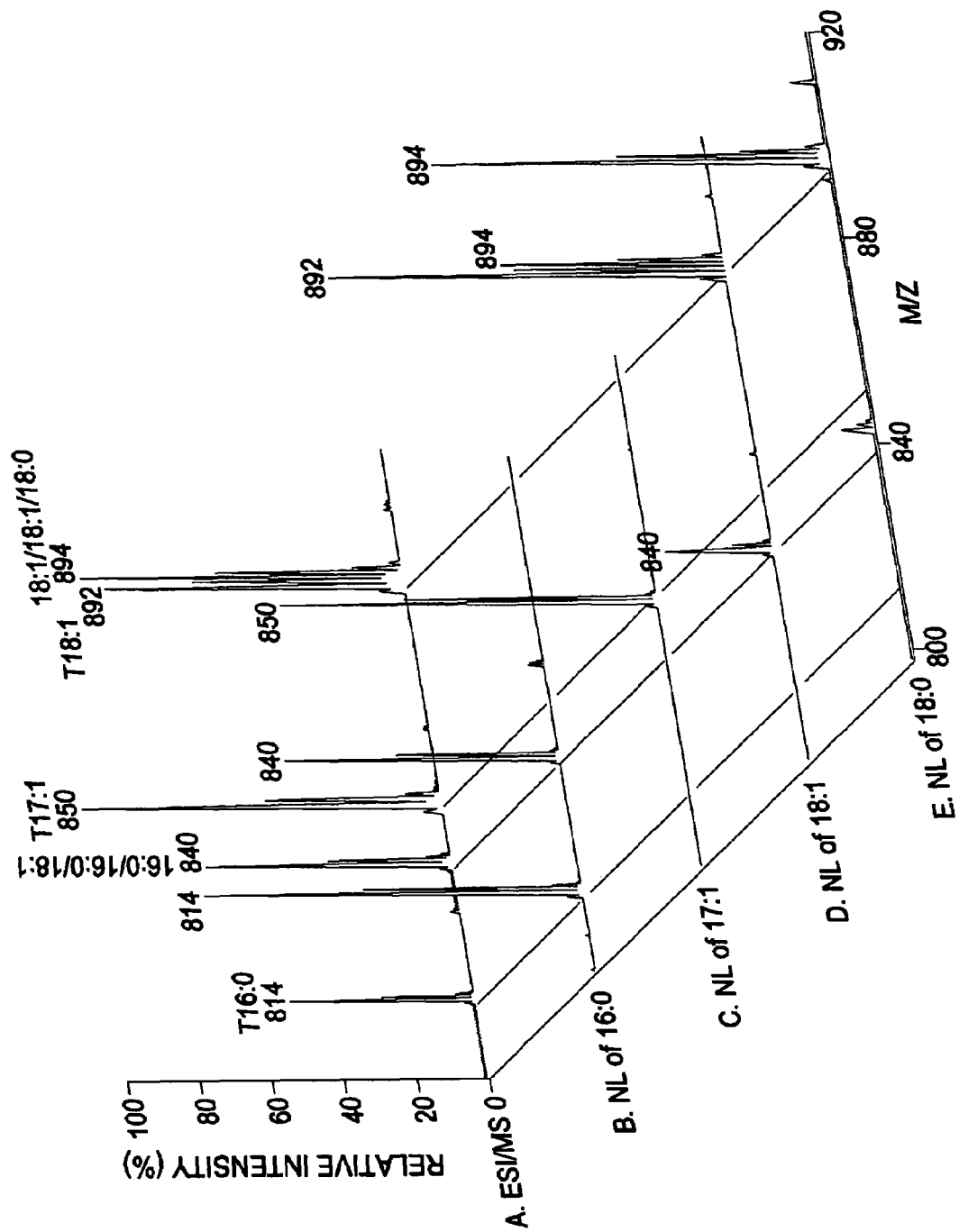

FIG. 4 depicts Positive-ion electrospray ionization mass spectrum and tandem mass spectra of an equimolar mixture of triglycerides by neutral loss scanning. An equimolar mixture of T16:0, 18:1/16:0/16:0, T17:1, T18:1, and 18:1/18:1; 18:0 TG (2 pmol each in a total volume of 200 μL) was prepared from stock solutions and extracted by a modified method of Bligh-Dyer in the presence of 50 mM LiOH in the aqueous phase as described under Materials and Methods. The solution of the TG mixture (in chloroform/methanol, 1:1 volume) was directly infused into the ESI ion source using a Harvard syringe pump at a flow rate of 1 μL/min. Positive-ion ESI mass spectrum (Row A) of the mixture was acquired as described under Materials and Methods. Positive-ion ESI tandem mass spectra with neutral loss of 16:0 (Row B), 17:1 (Row C), 18:1 (Row D), and 18:0 (Row E) were acquired through simultaneous scanning of both the first and third quadrupoles at fixed different masses (neutral loss) as described under Materials and Methods. All NL mass spectra were displayed after normalization to the base peak in the individual spectrum. The total ion counts of each individual ion in all neutral loss mass spectra were determined from four individually prepared solutions and the averaged results are tabulated in Table 2.

Figure 5:
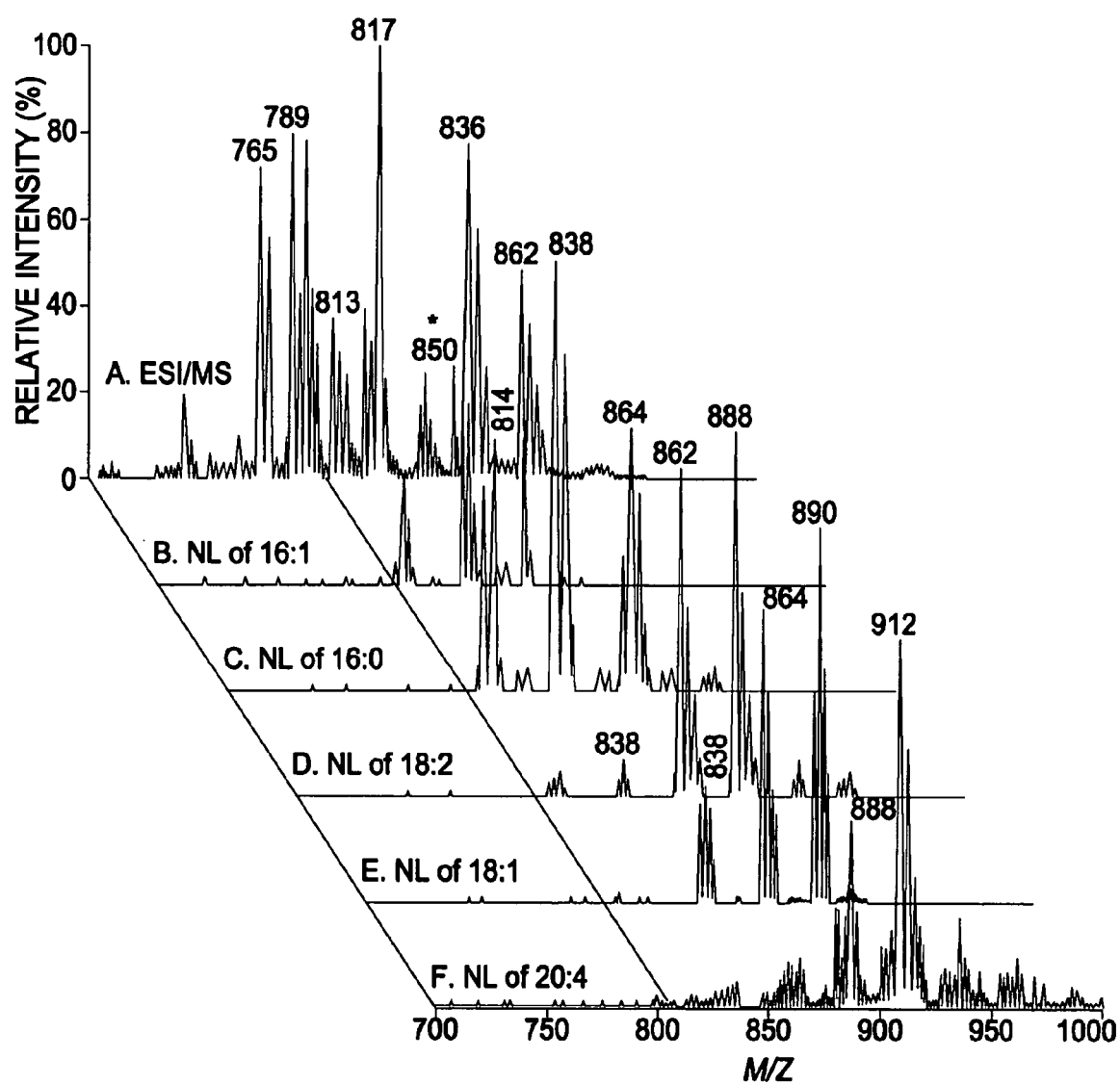

FIG. 5 depicts positive-ion electrospray ionization mass spectrum and neutral loss mass spectra of lipid extracts from rat myocardium. Lipid samples from rat myocrdium (~20 mg of wet tissue) were extracted by a modified method of Bligh-Dyer in the presence of 50 mM LiOH in the aqueous phase as described under Materials and Methods. Aliquots of the extracts in 1:1 chloroform/methanol were infused directly into the ESI source using a Harvard syringe pump at a flow rate of 1 μL/min. Positive-ion ESI mass spectrum (Row A) of lipid extracts was acquired as described under Materials and Methods. Positive-ion ESI tandem mass spectra of TG in lipid extracts with neutral loss of palmitoleic acid (16:1) (Row B), palmitic acid (16:0) (Row C), oleic acid (18:1) (Row D), linoleic acid (18:2) (Row E), and arachidonic acid (20:4) (Row F) were acquired through simultaneous scanning both first and third quadrupoles at fixed different mass values (neutral loss) as described under Materials and Methods. All NL mass spectra were displayed after normalization to the base peak in the individual spectrum. The total ion counts of each individual ion in mass spectra with neutral loss of each fatty acid were determined from four individually prepared mixture solutions and the averaged results are tabulated in Table 3. The internal standard peak (i.e. lithiated T17:1, TG) for TG quantification is indicated by the asterisk in Row A.

The data shown in the Figures is data of a tandem mass spectrum utilizing a neutral loss scanning. Data points on the ordinate(s) represent the number of ions (intensity) detected for a specific mass to charge ratio (mass to charge ratio is represented on the abscissa). The ion intensity at each mass to charge ratio is expressed relative to highest ion intensity at a specific mass to charge ratio. These ratios are expressed as a percent.

Multiple individual peaks are shown on the figures. Individual peaks are shown as one peak among many in the mass spectrum output. An individual peak represents a numerical count of the total ions detected at say m/z 849.7. In an aspect, we read from the tandem mass spectrometer output that this peak is the largest peak in the mass spectrum (100% relative ion intensity). We assume in our applications that the charge is one, so that the mass of this lithiated molecule is 849.7 DA.

H. Quantitation of TG Molecular Species using ESI/MS/MS

Figure 2A:
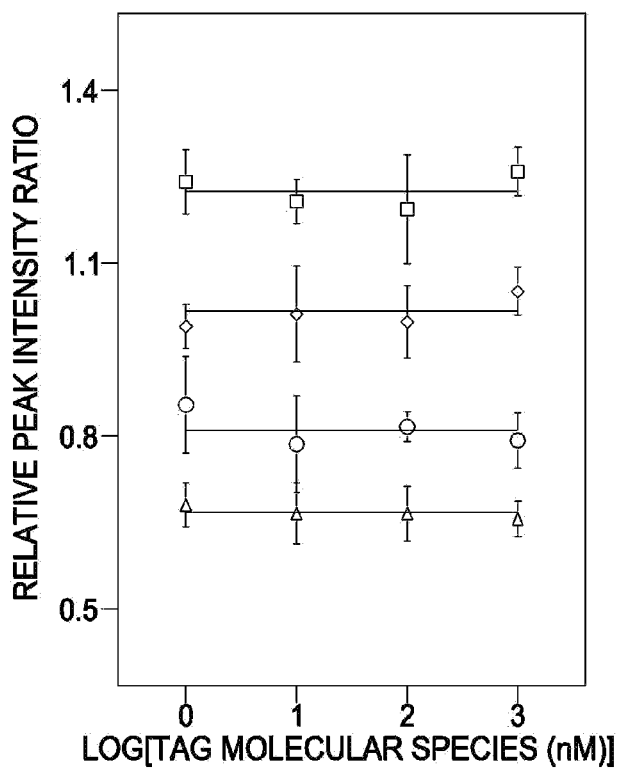

Our work has demonstrated that positive-ion ESI mass spectra of TG in the presence of lithium ion displayed predominant (>98%) lithiated TG molecular ions (8). However, the sensitivity of each TG molecular species in positive-ion ESI/MS was modestly (approximately 2-fold in the worst cases) dependent on the chain length and unsaturation index. For example, the positive-ion ESI mass spectrum of an equimolar mixture of T14:1, T14:0, T16:1, T16:0, T17:1, T18:2, T18:1, T18:0, T20:4, T20:2, T20:1, and T20:0 TG (10 nM for each molecular species) in the presence of LiOH displayed 12 molecular ion peaks with peak intensities which differed by at most 2-fold from internal standard, T17:1 TG (FIG. 1A). The sensitivity of each molecular species correlated with its unsaturation index and inversely correlated with its chain length. The intensity of each molecular species during positive-ion ESI mass spectra of TG was linear over a 1000-fold dynamic range examined (FIG. 2A).

Figure 2B:
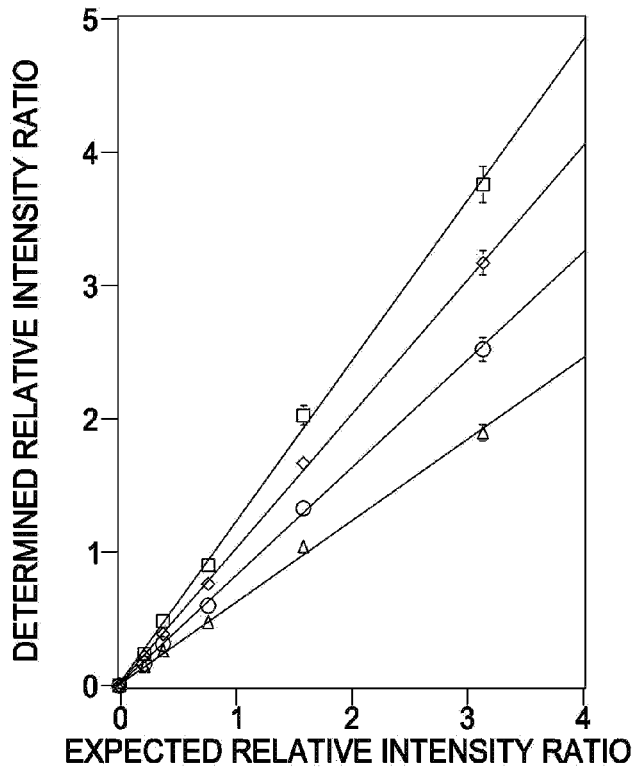

Detailed analyses of the concentration-response profile of TG molecular species after correction for $^{13}C$ isotope effects demonstrated a strictly linear response which possessed different slopes for each molecular species relative to the internal standard (FIG. 2B). Accordingly, comparisons between different TG molecular species can be directly observed, but absolute quantitation requires consideration of factors which lead to the differential sensitivities between molecular species. The slope of the least-square regressive linear fitting for each individual TG molecular species was defined as the correction factor for the sensitivity effect relative to T17:1 TG and tabulated for each molecular species examined (Table 1 immediately below).

TABLE 1

Sensitivity Correction Factors of Common TG Molecular Species to T17:1TG

| TG Molecular Species | Determined Correction Factor | Calculated Correction Factor* |
|---|---|---|
| T14:0 (42:0) | 0.92 ± 0.10 | 0.91 |
| T14:1 (42:3) | 1.22 ± 0.05 | 1.34 |
| T16:0 (48:0) | 0.69 ± 0.06 | 0.69 |
| T16:1 (48:3) | 1.00 ± 0.08 | 1.02 |
| 16:0/16:0/18:1 (50:1) | 0.71 ± 0.05 | 0.73 |
| 16:0/18:0/16:0 (50:0) | 0.62 ± 0.09 | 0.63 |
| 18:0/16:0/16:0 (50:0) | 0.62 ± 0.07 | 0.63 |
| T17:1 (51:3) | 1 | 0.91 |
| 16:0/18:0/18:1 (52:1) | 0.65 ± 0.05 | 0.67 |
| 16:0/18:1/18:0 (52:1) | 0.65 ± 0.08 | 0.67 |
| 16:0/20:4/16:0 (52:4) | 0.90 ± 0.09 | 0.94 |
| T18:0 (54:0) | 0.54 ± 0.09 | 0.53 |
| 18:0/18:1/18:1 (54:2) | 0.66 ± 0.07 | 0.7 |
| T18:1 (54:3) | 0.81 ± 0.06 | 0.78 |
| 16:0/20:4/18:1 (54:5) | 0.89 ± 0.08 | 0.94 |
| T18:2 (54:6) | 0.93 ± 0.03 | 1.03 |
| 18:0/20:4/18:0 (56:4) | 0.72 ± 0.09 | 0.79 |
| 18:1/20:4/18:1 (56:6) | 0.85 ± 0.09 | 0.93 |
| 18:2/20:4/18:2 (56:8) | 0.96 ± 0.08 | 1.08** |
| T20:0 (60:0) | 0.44 ± 0.06 | 0.45 |
| T20:1 (60:3) | 0.66 ± 0.06 | 0.61 |
| T20:2 (60:6) | 0.87 ± 0.08 | 0.77 |
| T20:4 (60:12) | 0.74 ± 0.08 | 1.09** |

*Calculated from $y = 4.4979 + 0.3441p - 0.1269q - 0.004845p*q + 0.00099qq$ Where p—total double bond numbers in TG; q—total carbon numbers in acyl chains of TG
**The differences between determine and calculated correction factors are over the experimental error. See text for detailed discussion.

The results demonstrated that the longer the acyl chain lengths and the lower the unsaturation index, the lower the sensitivity of TG molecular species in positive-ion ESI/S (FIGS. 2A and 2B and Table 1) with only one recognized exception (i.e., T20:4 TG). The results demonstrated that there were no differences of sensitivity correction factors between TG regioisomers (Table 1). A least-square regressive nonlinear curve fitting was performed to obtain correction factors for sensitivity of TG molecular species (except for T20:4 TG) as follows:

$$y = 4.4979 + 0.3441p - 0.1269q - 4.845 \times 10^{-3} p*q + 9.9 \times 10^{-4} q^2, \quad [3]$$

where y is a correction factor for sensitivity effect relative to T17:1, q is the total carbon number in the three acyl chains of a TG species, and p is the double bond number in a TG species.

To further assess the impact of arachidonoyl-containing triglycerides on the unanticipated lower sensitivity of T20:4 TG during ESI/MS analysis, we synthesized multiple naturally occurred arachidonyl-containing TG molecular species (i.e., 16:0/20:4/16:0, 16:0/18:1/20:4, 18:0/20:4/18:1, and 18:2/20:4/18:2 TG) and examined their ESI/MS spectroscopic properties (FIG. 1B) The experimentally determined correction factors for each of these species were generally well within the experimental error of the sensitivity factors calculated utilizing Eq. [3] (Table 1). It should be noted that the experimentally determined sensitivity factor of 18:2/20:4/18:2 TG (which contains 8 double bonds) was ~13% less than that calculated from Eq. [3]. Collectively, these results demonstrate that Eq. [3] allows accurate quantification for most naturally occurring triglycerides. However, triglycerides containing 8 to 12 double bonds are within 10-15% algorithm-predicted values and those with ≧12 double bonds should be accounted for by independent internal standards containing a similar number of double bonds. It should be recognized that the overwhelming amount of TG molecular species in biological samples contain fewer than 6 double bonds in the three acyl chains (collectively) allowing accurate quantitation using this algorithm. Moreover, direct comparisons between highly unsaturated molecular species (e.g., T20:4 TG) will still be valid, although absolute quantitative values derived from this algorithm should be interpreted with caution in the case of TG containing ≧12 double bonds.

Figure 3A:
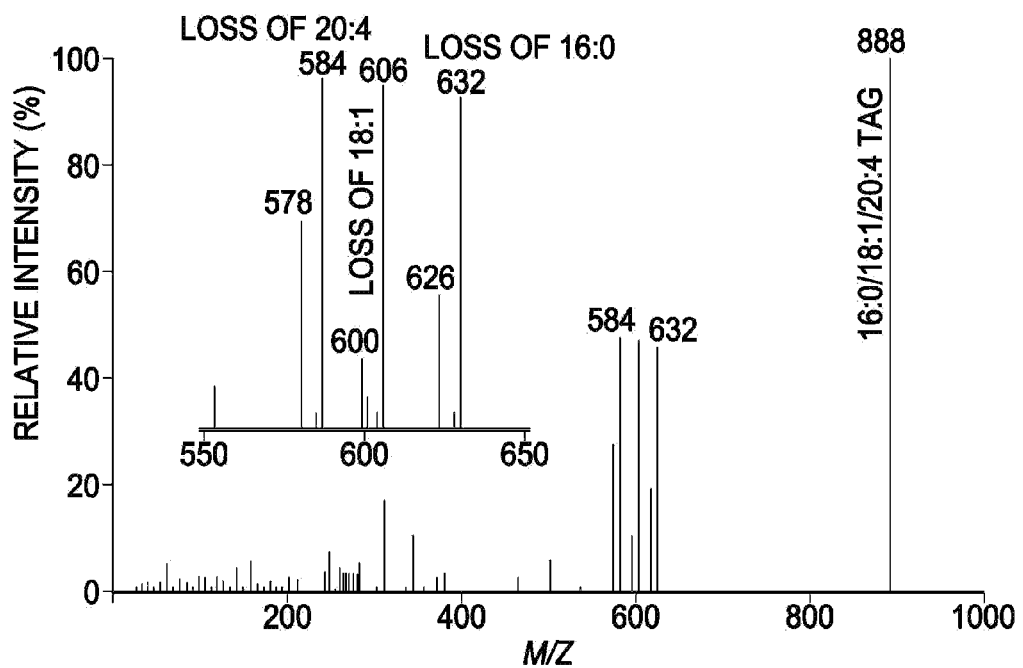
Figure 3B:
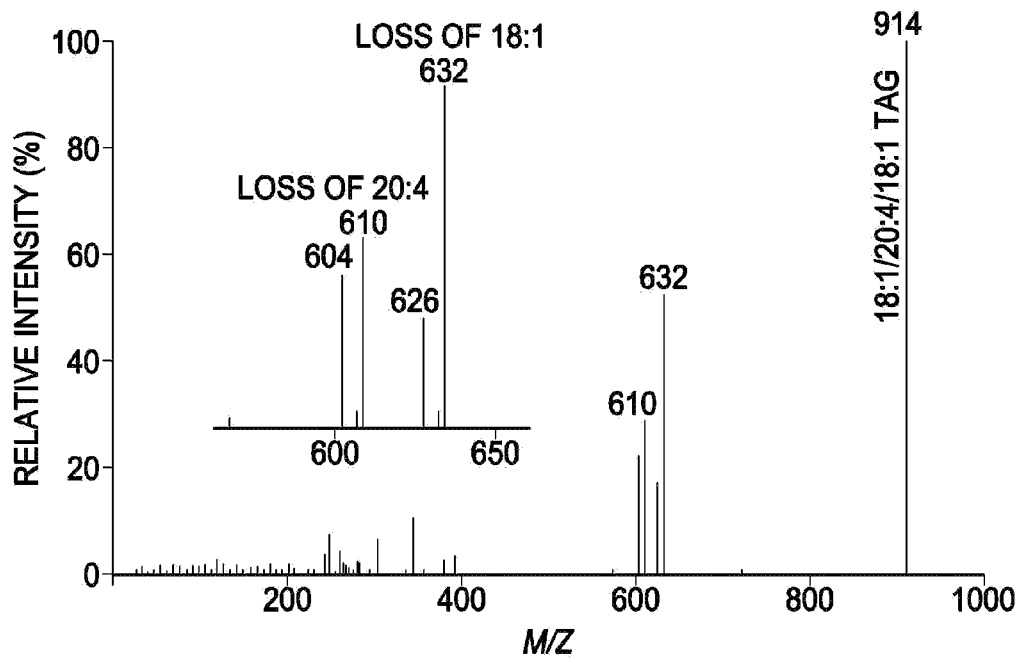

G. Fingerprinting of TG Molecular Species using Positive-Ion ESI Tandem Mass Spectrometry with Neutral Loss Scanning Our aforedescribed ESI/MS/MS of TG molecular species demonstrates that a set of abundant product ions could be generated by collisional activation which corresponded to the neutral loss of each fatty acid molecular species in the selected TG peak (insets in FIGS. 3A and 3B). Accordingly, we examined the abundance of product ions generated from TG molecular species and determined that the total number of ion counts corresponding to each fatty acid was proportional to the number of acyl chains in the parent TG molecular species (within 10% of the experimental error). For example, product ions at m/z 632, 606, and 584 in FIG. 3A correspond to the neutral loss of palmitic acid, oleic acid, and arachidonic acid from the lithiated 16:0/18:1/20:4 TG quasimolecular ion (m/z 888) which are present in a ratio of 1:1:1 (FIG. 3A). Similarly, product ions m/z 632 and 610 (FIG. 3B) correspond to the neutral loss of oleic acid and arachidonic acid from the lithiated 18:1/20:4/18:1 TG molecular ion (m/z 914) which are present in a ratio of 2:1 reflecting their abundance in the parent TG. Therefore, we explored the possibility that positive-ion ESI tandem mass spectrometry in the neutral loss mode can provide an informative fingerprint of the TG molecular species directly from biological samples without the need for prior chromatographic separation.

First, positive-ion ESI tandem mass spectra of an equimolar mixture of T:16:0, 18:1/16:0/16:0, T17:1, T18:1, and 18:1/18:1/18:0 TG (10 nM for each component) were acquired by scanning for the neutral loss of 256, 268, 282, and 284 [corresponding to the neutral loss of palmitic acid, heptadec-0O-enoic acid (17:1), oleic acid, and stearic acid, respectively] (FIG. 4). Arrangement of sequential neutral loss spectra of individual fatty acids in conjunction with their parent ion peaks results in the generation of a 2D (or multidimensional ESI/MS) spectrum which provides a detailed fingerprint of each of the acyl constituents contained in all the isobaric parent ions at a given mass value. The peak intensity ratio of acyl chains during neutral loss scanning reflected the number of each type of acyl chain present in the mixture of TG molecular species. For example, the intensity ratio of peaks at m/z 814 and 840 was present in a ratio of 3:2 during neutral loss scanning of palmitic acid (256) (Row B in FIG. 4) consistent with the presence of three palmitates in the molecular species at m/z 814 (T16:0 TG) and two palmitates in the molecular species at m/z 840 (18:0/16:0/16:0 TG). Tabulation of individual ion abundance (absolute ion counts) from the neutral loss scanning of each individual fatty acid with the molecular mass of the TG parent ion can be used to generate a two-dimensional matrix from which the fingerprinting of TG molecular species is possible (Table 2 below).

regiospecificity of each fatty acid in the glycerol backbone but does allow the quantification of the three fatty acids which reside on the glycerol of each TG molecular species. For example, the molecular species at m/z 840 appeared in neutral loss scanning mass spectra of palmitic acid (16:0, MW 256) and oleic acid (18:1, MW 282) with an approximate ratio of 2:1 (Rows B and D in FIG. 4; Table 2), suggesting that this molecular species contains two palmitates and one oleate. The total ion counts of this molecular species (after correction for $^{13}C$ isotope effects and sensitivity effects) were almost identical with the internal standard (i.e., T17:1 TG; Table 2). The obtained concentration of each individual molecular species was identical within experimental errors (right column in Table 2; 10 nM).

H. Quantitation of TG Molecular Species in Lipid Extracts of Rat Myocardium by Positive-Ion ESI Tandem Mass Spectrometry in the Neutral Loss Mode As previously reported, positive-ion ESI mass spectra of lipid extracts from rat myocardium demonstrated predominant lithiated choline-containing phospholipids (e.g., m/z 765, 767, 789, 793, and 817) as well as lithiated TG molecular species (e.g., m/z 814 and 840). Since most biological tissues have substantially more choline-containing phospholipids than TG, this overlap effectively precludes the direct quantitation of TG molecular species. However, application of positive-ion ESI tandem mass spectrometry in the neutral loss mode facilitates their quantitative analysis by "spectroscopic" resolution since the neutral loss of fatty acids is

TABLE 2

Quantitative Analysis of an Equimolar Mixture of TG Using Positive-Ion ESI/MS/MS in Neutral Loss Mode

| [M + Li]+ | TG Species | 16:0 (NL 256) | 17:1 (NL 268) | 18:1 (NL 282) | 18:0 (NL 284) | Total Ion Counts* | Total TG (nM) |
|---|---|---|---|---|---|---|---|
| 814 | T16:0 | 165.2 ± 9.9 | | | | 239.42 ± 17.6 | 9.3 ± 0.7 |
| 840 | 16:0/16:0/18:1 | 123.4 ± 4.9 | | 55.5 ± 2.4 | | 245.1 ± 12.3 | 9.5 ± 0.5 |
| 850 | T17:1 | | 258.4 ± 12.5 | | | 258.4 ± 12.5 | 10.0 ± 0.5 |
| 892 | T18:1 | | | 207.7 ± 10.1 | | 266.3 ± 10.8 | 10.3 ± 0.4 |
| 894 | 18:1/18:1/18:0 | | | 118.0 ± 7.7 | 52.1 ± 2.3 | 243.0 ± 11.5 | 9.4 ± 0.4 |
| | Total Ion Counts* | 408.5 ± 19.9 | 258.4 ± 12.5 | 510.9 ± 28.5 | 74.4 ± 3.6 | | 48.5 ± 2.5 |
| | Total FA (nM) | 47.4 ± 2.3 (5) | 30.0 ± 1.5 (3) | 59.3 ± 3.3 (6) | 8.6 ± 0.4 (1) | 145.3 ± 6.2 | |

With a known concentration of internal standard, this 2D (or multidimensional ESI/MS) mass spectroscopic procedure can directly quantitate the molecular species distribution of TG from chloroform extracts of biological samples as described below.

From the two-dimensional matrix composed of absolute ion counts generated from the neutral loss scanning of individual fatty acids, the relative contribution of individual isobaric molecular species of TG to each parent ion peak can be quantitated. After the generation of the parent ion, all fatty acids examined (i.e., 16:0, 17:1, 18:0, 18:1, 18:2, and 20:4) derived from the parent ion were released with equal efficiency after collisional activation under the conditions employed (FIG. 3). Accordingly, individual molecular species contributions can be calculated from the relative ion counts present at each molecular mass by identifying a molecular species which has a single fatty acid represented. This unitary response factor can then be utilized to deconvolute molecular species information from the 2D (or multidimensional ESI/MS) matrix of ion counts and TG molecular species mass. This approach does not determine the absent in choline glycerophospholipids due to the >100-fold more rapid loss of the polar head group than the fatty acid after collisional activation (27).

We recognized that by scanning all potential naturally occurring fatty acids of lipid extracts from rat myocardium, a two-dimensional matrix (one dimension corresponding to the fatty acids occurring in the TG molecular species of lipid mixtures and a second corresponding to parent molecular ions) could be constructed which would reveal a detailed fingerprint of individual TG molecular species directly from lipid extracts (FIG. 5). We and others have previously demonstrated that the predominant naturally occurring fatty acids in TG molecular species are 16:0, 16:1, 18:1, 18:2, and 20:4 (FIG. 5). In chloroform extracts of rat myocardium, there were more than 10 major crosspeaks present at m/z 812, 814, 836, 838, 840, 862, 864, 866, 888, 890, 892, 912, and 914 as well as an intense peak corresponding to internal standard (m/z 850) which was omitted for clarity in FIG. 5. Positive-ion ESI tandem mass spectra with NL of palmitoleic acid (16:1) and palmitic acid demonstrated several abundant buried TG molecular ion peaks (e.g., m/z 810 and 812 in Row B and m/z 812, 814, and 840 in Row C, FIG. 5).

TABLE 3

Tandem ESI Mass Spectrometric Analyses of TG Molecular Species in Lipid Extracts of Rat Myocardium (pmol/mg of protein)

| m/z | Major Molecular Species | NL16:1 | NL16:0 | NL17:1 | NL18:2 | NL18:1 | NL18:0 | NL20:4 | Total Ion Counts* | TG Content |
|---|---|---|---|---|---|---|---|---|---|---|
| 810 | 16:0/16:1/16:1(48:2) | 10.5 ± 1.8 | 4.9 ± 6.6 | | | | | | 16.9 ± 2.6 | 15 ± 2 |
| 812 | 16:0/16:0/16:1(48:1) | 17.4 ± 1.5 | 35.5 ± 3.2 | | | | | | 66.2 ± 4.1 | 59 ± 5 |
| 814 | T16:0(48:0) | | 43.4 ± 2.2 | | | | | | 62.9 ± 2.6 | 56 ± 4 |
| 836 | 16:1/16:1/18:1(50:3) | 39.4 ± 2.9 | | | | 22.2 ± 1.2 | | | 66.2 ± 4.1 | 59 ± 4 |
| 838 | 16:0/16:1/18:1&(50:2) | 33.6 ± 2.2 | 66.7 ± 4.7 | | 9.8 ± 0.8 | 33.3 ± 2.5 | | | 172.7 ± 12.1 | 155 ± 13 |
| 840 | 16:0/16:0/18:1(50:1) | | 47.5 ± 1.1 | | | 25.2 ± 1.0 | | | 102.7 ± 2.3 | 92 ± 5 |
| 850 | T17:1(53:3) | | | 167.6 ± 8.7 | | | | | 167.6 ± 8.7 | [150] |
| 862 | 16:1/18:1/18:2&(52:4) | 32.5 ± 2.6 | 33.3 ± 2.2 | | 95.0 ± 7.2 | 33.9 ± 2.0 | | 3.3 ± 0.2 | 210.0 ± 10.2 | 189 ± 12 |
| 864 | 16:0/18:1/18:2&(52:3) | 13.5 ± 1.5 | 46.4 ± 3.8 | | 55.2 ± 5.6 | 76.0 ± 7.2 | | | 221.3 ± 17.6 | 198 ± 16 |
| 866 | 16:0/18:1/18:1(52:2) | | 26.9 ± 2.2 | | | 53.8 ± 3.1 | | | 106.1 ± 5.1 | 95 ± 7 |
| 888 | 18:1/18:2/18:2&(54:5) | | 9.7 ± 0.4 | | 118.6 ± 6.7 | 52.3 ± 3.1 | | 10.4 ± 0.6 | 203.2 ± 18.7 | 182 ± 17 |
| 890 | 18:1/18:1/18:2(54:4) | | | | 54.3 ± 3.6 | 100.4 ± 6.6 | | 2.3 ± 0.2 | 182.6 ± 9.9 | 163 ± 11 |
| 892 | T18:1(54:3) | | | | | 67.2 ± 6.7 | | | 83.0 ± 7.4 | 74 ± 7 |
| 894 | 18:0/18:1/18:1(54:2) | | | | 6.1 ± 0.7 | | 10.0 ± 0.8 | | 23.0 ± 1.2 | 21 ± 1 |
| 912 | 18:1/18:2/20:4(56:7) | | | | 21.7 ± 1.5 | 17.8 ± 1.4 | | 19.5 ± 1.6 | 54.5 ± 3.2 | 49.0 ± 4 |
| 914 | 18:1/18:1/20:4&(56:6) | | | | 14.5 ± 1.2 | 6.2 ± 0.5 | 14.1 ± 1.2 | 15.8 ± 1.4 | 59.0 ± 4.2 | 53 ± 4 |
| | Total Ion Counts* | 166.6 ± 14.1 | 394.2 ± 31.5 | 167.6 ± 8.7 | 412.9 ± 33.8 | 577.8 ± 43.0 | 29.4 ± 1.8 | 53.5 ± 3.8 | | 1460 ± 115 |
| | FA Content | 447 ± 41 | 1058 ± 94 | [450] | 1109 ± 91 | 1551 ± 136 | 79 ± 5 | 144 ± 10 | 4388 ± 368 | |

By recording the cross-peak ion abundance of all relevant molecular ions (>1 mol% of total TG content) in the 2D (or multidimensional ESI/MS) spectrum by correcting the directly measured ion intensity for $^{13}$C isotope effects, a 2D (or multidimensional ESI/MS) matrix was obtained (Table 3). From each molecular ion in the 2D (or multidimensional ESI/MS) mass spectrum, the total carbon number and total number of double bonds collectively present in the three aliphatic chains can be calculated and defined as q:p (listed in parentheses in the second column in Table 3), where q is the total carbon number and p is the double bond number in the three acyl chains of the TG species. To deconvolute the molecular species information in Table 2, an iterative procedure must be employed.

First, the lowest abundant neutral loss ion in a row is located and for that molecular species the other two acyl chains ($m_2$:$n_2$ and $m_3$:$n_3$ must obey $$m_2 + m_3 = q - m \qquad [4]$$

and $$n_2 + n_3 = p - n_1, \qquad [5]$$

where $m_1$, $m_2$, and $m_3$ are integers which represent total carbon number and $n_1$, $n_2$, and $n_3$ represent total double bonds in three acyl chains, respectively. Since fatty acids in isobaric molecular species of TG must contain reciprocal changes in the carbon numbers and the number of double bonds, these two acyl chains can be readily defined from ion peaks corresponding to the neutral loss of fatty acids in the same row of Table 3.

Next, the lowest abundant peak is subtracted from the acyl chains in $m_2$ and $m_3$.

After subtraction, the next lowest abundant ion is located and a second round of deconvolution can be performed to identify a second isobaric molecular species. All TG molecular species can be defined by repeated iteration of this procedure. For example, in the TG molecular species present at m/z 862 (i.e., 52:4), there are five cross-peaks present in the same row of Table 3 resulting from the neutral loss of 16:0, 16:1, 18:1, 18:2, and 20:4. The lowest abundant ion present from the neutral loss of 20:4 (3.3×10$^3$ ion counts) is utilized for the first round of deconvolution. The other two acyl chains must contain 32 carbons and no units of unsaturation, which is only possible with two 16:0 chains. Thus, the molecular species is 16:0/16:0/20:4 TG which represents 3.3×10$^3$ ion counts relative to the internal standard. By subtracting the contribution of 16:0/16:0/20:4 TG molecular species from the ion abundance of NL 16:0 in the same row, a new value is obtained which is utilized to begin the second round of deconvolution. The next lowest abundant ion is located at the cross-position reflecting NL of 16:0 with 26.7×10$^9$ ion counts [(33.3−6.6)× 10$^3$]. Thus, the other two acyl chains must contain 36 carbons with 4 units of unsaturation which can successfully be fit by two 18:2 chains. Therefore, the molecular species responsible for these peaks is 16:0/18:2/18:2 TG with ~27×10$^3$ ion counts relative to the internal standard. The remaining ions in the m/z 862 row are present in an approximate 1:1:1 ratio corresponding to a 16:1/18:1/18:2 TG. Therefore, the molecular ion at m/z 862 can be deconvoluted into parts composed of 16:0/16:0/20:4, 16:0/18:2/18:2, and 16:1/18:1/18:2 TG molecular species with an approximate ratio of 1:9:10. All other molecular ions are similarly deconvoluted and the major molecular species corresponding to each molecular ion are listed in the second column of the 2D (or multidimensional ESI/MS) matrix (Table 3).

Our example demonstrates that TG content and molecular species composition are directly quantified from chloroform extracts of biological samples. By employing correction factors necessary to accommodate the differential sensitivity of individual TG molecular species for ionization (relative to an internal standard (T17:1 TG)), TG content can be quantified by positive-ion ESI mass spectrometry over a three order of magnitude concentration range with less than 10% error. Moreover, by generating a 2D (or multidimensional ESI/MS) matrix comprised of axes corresponding to parent ions and the neutral loss of fatty acid, the methodology described herein can be used to deconvolute the TG molecular species overlapping with other polar lipids as well as calculate contributions of individual isobaric molecular species to each parent ion peak. Thus, ESI/MS/MS in conjunction with appropriate matrix analysis allows a detailed molecular species fingerprint of individual TG molecular species directly from chloroform extracts of biological samples.

In an aspect, the term "matrix analysis" includes data deconvolution and optionally data normalization.

The aforerecited expression 1-5 represent equations or algorithms which in an aspect we applied to provide a TG molecular species determination.

Correction factors derived from the algorithm generated herein are only accurate to ±5% for molecular species containing less than 8 double bonds (collectively) and only accurate to ±15% for molecular species containing 8 to 12 double bonds (collectively). Fortunately, highly polyunsaturated TG molecular species (>8 double bonds, collectively) are rare in biological samples. If an accurate analysis of TG molecular species containing multiple polyunsaturated fatty acyl chains is required, use of additional internal standards with a similar degree of unsaturation would be prudent. Third, both the collisional activation energy as well as spectrometer tuning and calibration are of substantial importance in generating a 2D (or multidimensional ESI/MS) matrix which accurately reflect TG molecular species content in the neutral loss mode. If the collisional activation energy is too high (e.g., >40 eV), fragmentation of acyl chains becomes severe and the abundance of product ions corresponding to neutral loss of fatty acids from a TG molecular species will be compromised by the further differential fragmentation of these product ions. If the collisional activation energy is too low (e.g., <30 eV), the efficiency of collisional dissociation is lost and the exquisite sensitivity of this method is compromised. Therefore, this dc offset voltage set on the second quadrupole must be tested initially on each instrument. Moreover, the tuning and calibration of the spectrometer are also critical since the accuracy of this methodology is not only dependent upon the mass accuracy of both the first and third quadrupoles but also dependent upon the neutral loss mass difference between these two analyzers. Finally, fluctuations of experimental conditions (e.g., infusion rate, drying gas temperature and pressure, collisional gas pressure and energy, and vacuum system) during neutral loss scanning must be avoided. Averaging several sets of acquired experimental data at different time periods from an identical sample can minimize this type of experimental error.

Aside from the aforegoing limitations, 2D (or multidimensional ESI/MS) mass spectrometry of TG molecular species is a new, rapid, and convenient and direct approach to analyze the TG content of biological samples under different pathophysiologic perturbations. Although minor errors (typically less than 10%) are inherent in the assumptions utilized, fingerprinting of TG molecular species in disease states by the methods described herein provides the most discriminating comparisons between TG molecular species described to date. Furthermore, through the utilization of isotopically labeled fatty acids (e.g., deuterium or 13C) and giving these to subjects or patients unique insights into the turnover of individual molecular species are possible which will hopefully lead to an increased understanding of the role of TG in health and disease.

In an aspect, the above-described inventive methods are utilized by physicians and pharmaceutical companies to determine the risk of each individual (or group of) molecular species as an independent factor in the development of coronary artery disease, stroke, atherosclerosis and obesity as well as to target agents to selectively modify triglyceride molecular species (e.g., saturated triglycerides). Coronary artery disease, stroke, atherosclerosis and obesity are afflictions of humans which take hundreds of thousands of lives each year unnecessarily. Medical advances which assess the risk of an individual to develop one or more of these afflictions are highly desired. Moreover, these methods can be utilized to determine which lipid lowering drug is most efficacious in clinical trials and to monitor the response of patients to tailored drug therapy.

In an aspect these inventive methods are utilized to determine and identify a lipid lowering drug(s) which is most efficacious in clinical trials and other tests and to monitor the response of patients to tailored drug therapy.

Lipid lowering drugs are especially useful for treating patients who have high levels of fat in the blood which may have come about as a result of an inherited condition known as familial hyperlipidaemia. Such lipid lowering drug therapy is highly desired to lower the levels of fat in the blood and to lower the risk of atherosclerosis (hardening of the arteries) and heart disease, and an early death. From vast libraries of potential candidate drugs for pharmacological effective treatment, the management of such libraries need to have better ways of assessing and identifying those candidate drugs which have the highest potential to provide patient lipid lowering capability in practice. In an aspect, this invention provides a method of identifying those lipid lowering drugs which have the capability to lower lipid concentrations in the blood streams of humans after the administration of an effective amount of a lipid lowering drug to that patient.

Lipid lowering drugs are useful in treating coronary artery disease which is the number one killer of Americans today. This disease is caused by the buildup on plaque, deposits of fatty like substances and is called atherosclerosis. When a coronary artery is blocked by such plaque a heart attack can occur which is termed a myocardial infarction. It is highly desired to identify a lipid lowering drug and to assign a risk to an individual of a potential development of a medical problem due to high fat levels in his/her blood.

Recently there have been strides in pharmacogenomics which relates to the tailoring of drugs for individuals based on individual genomic characteristics that may play an important part in the individual's response to a drug. Individual drug therapy is likely to become a major therapy in the fight against killer diseases. Treating physicians benefit by knowing whether a drug efficacy is subject to genetic polymorphisms in the patient being treated which inhibit the patients response to the drug treatment. Feedback to the treating physician on the drug's biochemical response within the treated subject is of great importance in determining better how to use the drug in a more effective individual specific therapy.

In an aspect, the methods herein are useful to indicate the risk or likelihood of getting a disease, help confirm a diagnosis and assist in planning or customizing patent treatment. A method for assessing and assigning a risk to each individual (or group of individuals) based on TG molecular species as an independent factor in the development of at least one of condition in that individual for a medical condition selected from coronary artery disease, stroke, atherosclerosis and obesity comprises analyzing a biological sample of an individual for TG molecular species determination, administering a therapeutic amount of a drug to the individual, analyzing a corresponding biological sample of said administered individual, comparing the TG molecular species determination after drug administration with the TG molecular species determination prior to the drug administration and determining a risk therefrom associated with that individual.

The comparison of the TG molecular species determination of the biological samples is indicative of development of the condition for that individual. A risk is assigned to that individual for a respective medical condition which is indicative of the risk to that individual developing that respective medical condition at some time during his/her lifetime.

A method for determining an agent which selectively targets triglyceride molecular species (e.g., saturated triglycerides) comprises analyzing a biological sample of at least one individual for TG molecular species determination, administering a therapeutic amount of a drug to the individual, analyzing a biological sample of said administered individual, comparing the TG molecular species determination after said administration with the TG molecular species determination prior to the drug administration and determining an effect if any on the individual of the drug administration. In an aspect, the comparison of the TG molecular species determination of the biological samples is indicative of development or risk of the condition for that individual.

A method of identifying a candidate lipid modulating drug having lipid modulating drug efficacy comprises selecting a biological sample to be taken, analyzing a biological sample of at least one individual for TG molecular species determination, administering a candidate lipid lowering drug to the individual, analyzing a biological sample of said administered individual, comparing the TG molecular species determination after said administration with the TG molecular species determination prior to the drug administration and determining an effect if any on the individual of the drug administration. In an aspect, the comparison of TG analysis is indicative of the lipid metabolic altering capacity of an administered drug. In an aspect, the amount of candidate lipid lowering drug provided to the individual is a therapeutic amount and the drug is a pharmacologically acceptable chemical.

In an aspect, dynamic incorporation of stable isotopes $^2H$ palmitate and oral administration the timed dynamic response to lipid loading and turnover can be assessed.

In an aspect, a method to diagnose and determine the response of patients to tailored drug therapy comprises analyzing a biological sample of at least one individual for TG molecular species determination, administering a therapeutic amount of a drug to the patient, analyzing a biological sample of said administered to patient, comparing the TG molecular species determination after the administration with the TG molecular species determination prior to the drug administration and determining an effect if any on the individual of the drug administration. In an aspect, the comparison of TG analysis is indicative of a tailored drug therapy. In an aspect, the amount of drug provided to the individual is a therapeutic amount and the drug is a pharmacologically acceptable chemical.

In an aspect a method of screening candidate chemicals for lipid modulating potential in a subject comprises analyzing a biological sample of at least one individual for TG molecular species determination, administering a drug to that biological subject, analyzing a biological sample taken from the treated subject, comparing the TG molecular species determination of the treated subject with a TG molecular species determination prior to the drug administration and determining therefrom an effect on the subject of the drug administration. In an aspect, the comparison of TG analysis is indicative of a candidate chemical having a lipid modulating potential. In an aspect, the amount of candidate lipid lowering drug provided to the individual is a therapeutic amount and the drug is a pharmacologically acceptable chemical.

All publications, patents and patent applications are herein incorporated by reference in their entirety to the same extent as if each individual publication, patent or patent application was specifically and individually indicated to be incorporated by reference in its entirety.

2D (or multidimensional ESI/MS) Mass Spectrometric Fingerprinting of Lipid Classes, Subclasses And Individual Molecular Species Directly from Chloroform Extracts (Strategy)

Figure 6:
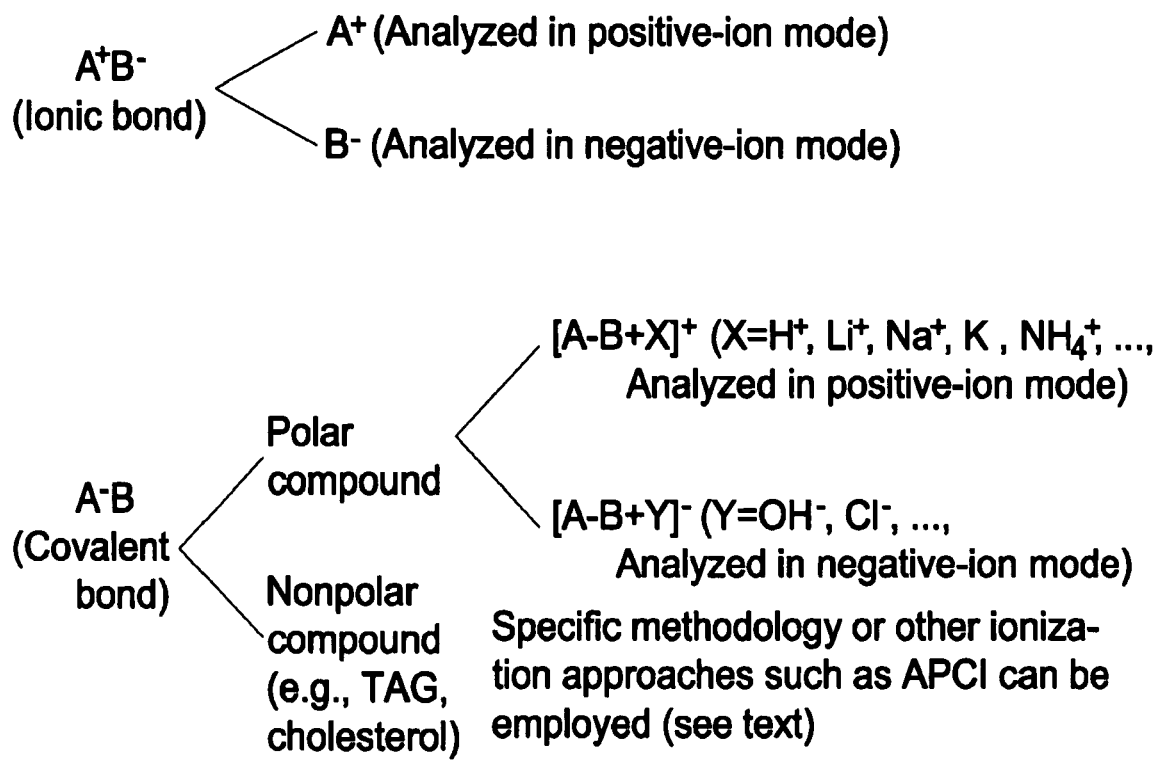
FIG. 6. Diagram of the ionization of ionic or covalent-linked compounds by electrospray.
Figure 7:
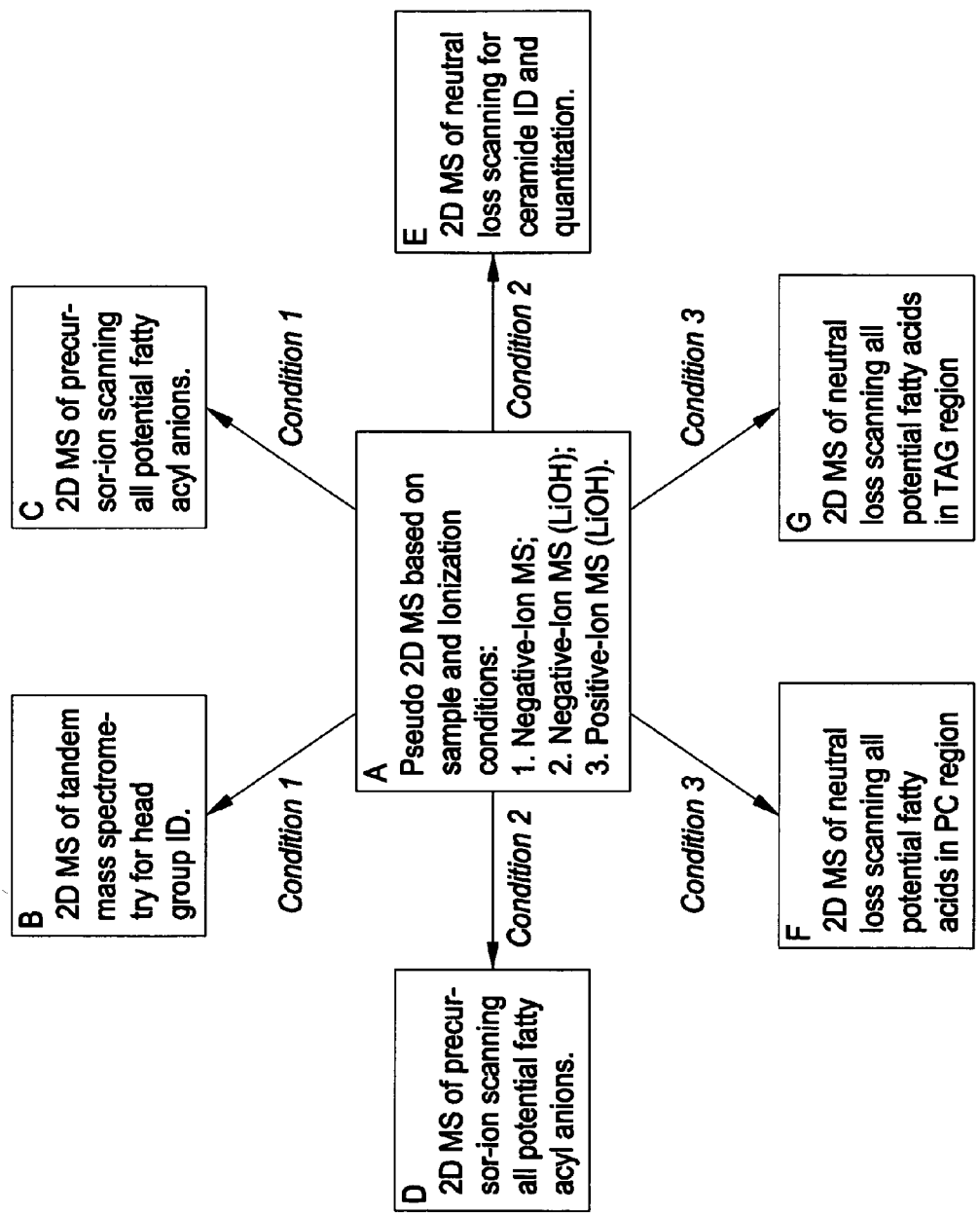
FIG. 7. A strategy for global lipidome analysis by two-dimensional electrospray ionization mass spectrometry. This diagram provides an overview of the 2D (or multidimensional ESI/MS) mass spectrometric approach beginning with the extraction and the production of reagent ion-analyte pairings (center box, A). Subsequent 2D (or multidimensional ESI/MS) mass spectrometric analysis under neutral conditions (boxes B and C) leads to identification of anionic lipids. Addition of LiOH just prior to sample injection (Condition 2) and subsequent 2D (or multidimensional ESI/MS) analysis (boxes D and E) in the negative-ion mode leads to fingerprinting of individual molecular species of ethanolamine glycerophospholipids, nonesterified fatty acids, and ceramides. Next, by changing the source polarity to the positive-ion mode under alkaline conditions (Condition 3), individual molecular species of choline glycerophospholipids, sphingomyelins, and triacylglycerols can be fingerprinted by 2D (or multidimensional ESI/MS) mass spectrometry (boxes F and G). Through this approach all major classes, subclasses, and individual molecular species can be fingerprinted and quantitated through the 2D (or multidimensional ESI/MS) strategy described in the text.

ESI can also be used for molecules which do not posses any intrinsic ionizable site through formation of adduct ions as illustrated in FIG. 6. Thus, as long as a sufficient dipole potential is present in a molecule to interact with either a small anion or cation, it can be ionized during the ESI process if appropriate conditions are utilized. For example, although triacylglycerols (TAG) containing long chain fatty acids are nonpolar lipids, TAG can be ionized and quantitated with a sensitivity in the low picomole range through formation of lithiated adducts formed from chelated lithium ions non-covalently associated with the carbonyl in the infused solution (8, 36).

The utility of selective ESI volatization is based on the differential propensity of each lipid class to acquire either positive or negative charges under the source high voltage. This was exploited to allow the resolution of lipid classes directly from chloroform extracts without prior chromatographic separation (25, 26). In essence, lipid classes can be separated through their endogenous electric potential, thereby obviating multiple sequential chromatographic procedures. Through judicious use of sample preparation, each class of lipids can be resolved in the ionization source and individual molecular species can be further resolved by MS and/or tandem MS. During the last decade, studies in our group and those of our colleagues have demonstrated that ESI/MS of lipids represented one of the most sensitive, discriminating, and direct methods to assess alterations in the cellular lipidome (see refs. 25, 26, 28, 36, 37, 43, 46, 47, 48 for examples).

Through appropriate sample preparation ESI/MS allows: 1) the complete quantitative analysis of lipid classes, subclasses, and individual molecular species in minutes without prior chromatographic separation or derivatization; 2) a higher signal to noise ratio in comparison to other mass spectrometric approaches; 3) a nearly linear relationship between the relative intensities of molecular ions and the mass of individual lipids over a 10,000-fold dynamic range; 4) independence of ion intensity (within experimental error (<5%))

on the nature of the polar lipid subclass or the individual molecular species; and 5) excellent reproducibility of sample measurements (<5% of experimental error). Through implementation of these techniques, a high throughput platform for the detailed study of lipid alterations has been developed at a time when lipid-induced disease states are epidemic in industrialized nations (e.g., diabetes, obesity, and atherosclerosis).

The principles used in the 2D (or multidimensional ESI/MS) ESI/MS quantitation of cellular lipidomes directly from lipid extracts of biological samples are derived from the ability to induce specific analyte-reagent ion interactions (which effectively resolve lipid classes in the ion source) in conjunction with neutral loss or precursor-ion scanning of each class or subgroup of ionized species. Through this approach, the individual molecular species, as well as the amounts of individual isobaric species in each ion peak, can be directly determined using three different analyte and reagent ion combinations as schematized in FIG. 7. Through judicious selection of ion-pairing reagents, this method can effectively fingerprint hundreds of different lipid molecular species from multiple different lipid classes and subclasses through the analysis of the intensities of 2D (or multidimensional ESI/MS) cross peaks derived from neutral loss and/or precursor-ion scanning. In this paper, we show 2D (or multidimensional ESI/MS) mass spectra of hepatic lipids under three different reagent ion-analyte pairings which effectively fingerprint most of the major and many of the minor lipid classes in the mouse liver lipidome directly from its crude chloroform extract.

2D (or Multidimensional ESI/MS) Mass Spectrometric Analysis of Heptic Lipid Classes And Molecular Species under Condition 1

Figure 8:
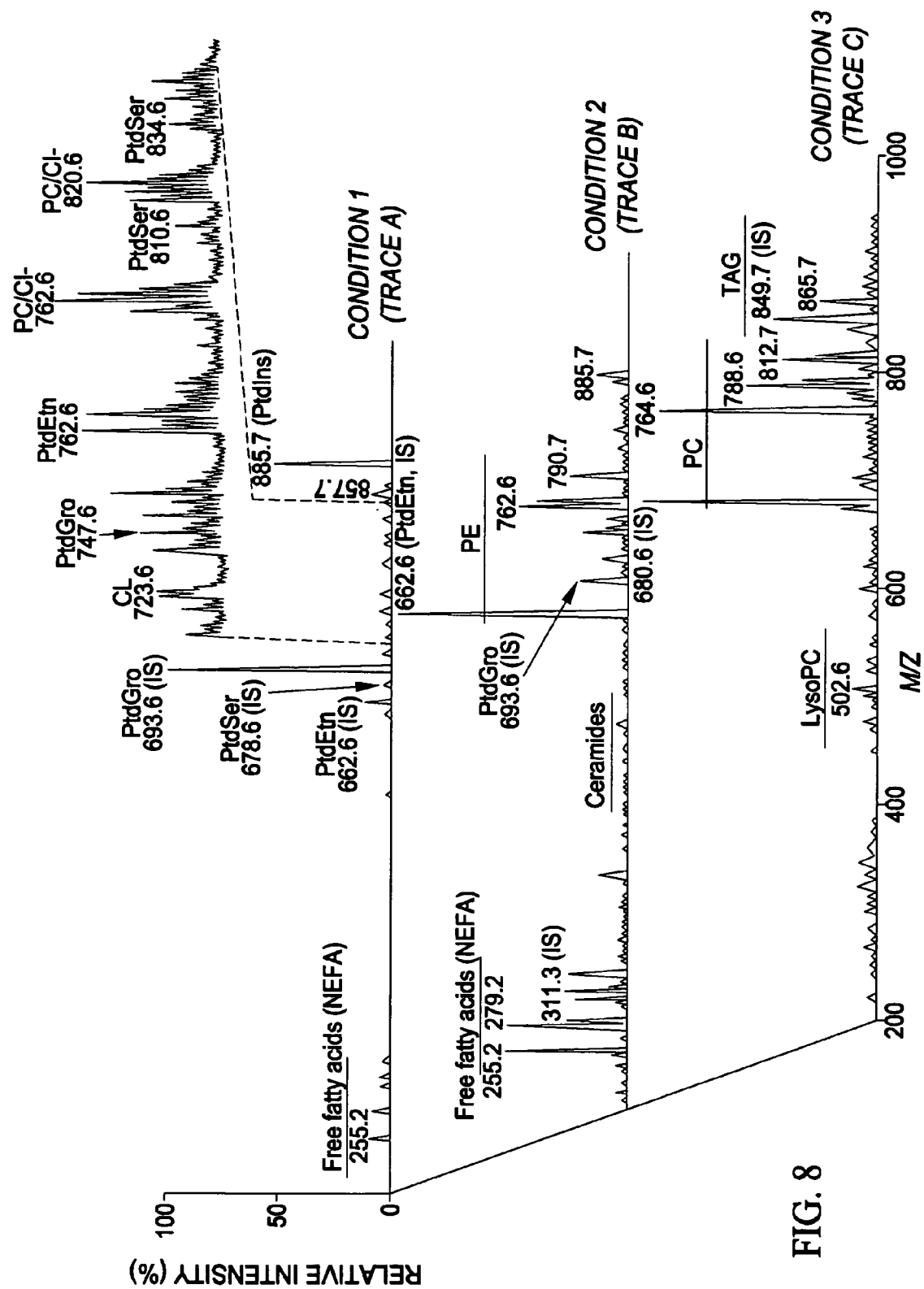
FIG. 8. A pseudo two dimensional (or multidimensional) electrospray ionization mass spectrum of lipid classes resolved by intrasource class-selective ionization. Hepatic lipid extracts were prepared as described in "Experimental Protocol" and treated with either no addition (Condition 1, Trace A), addition of 50 nmol LiOH/mg of protein and analyzed in the negative-ion mode (Condition 2, Trace B) or treated with LiOH and analyzed in the positive-ion mode (Condition 3, Trace C). "I.S." denotes internal standard; "CL" represents doubly-charged cardiolipin. All mass spectral traces were displayed after normalization to the base peak in each individual spectrum.
Figure 9A:
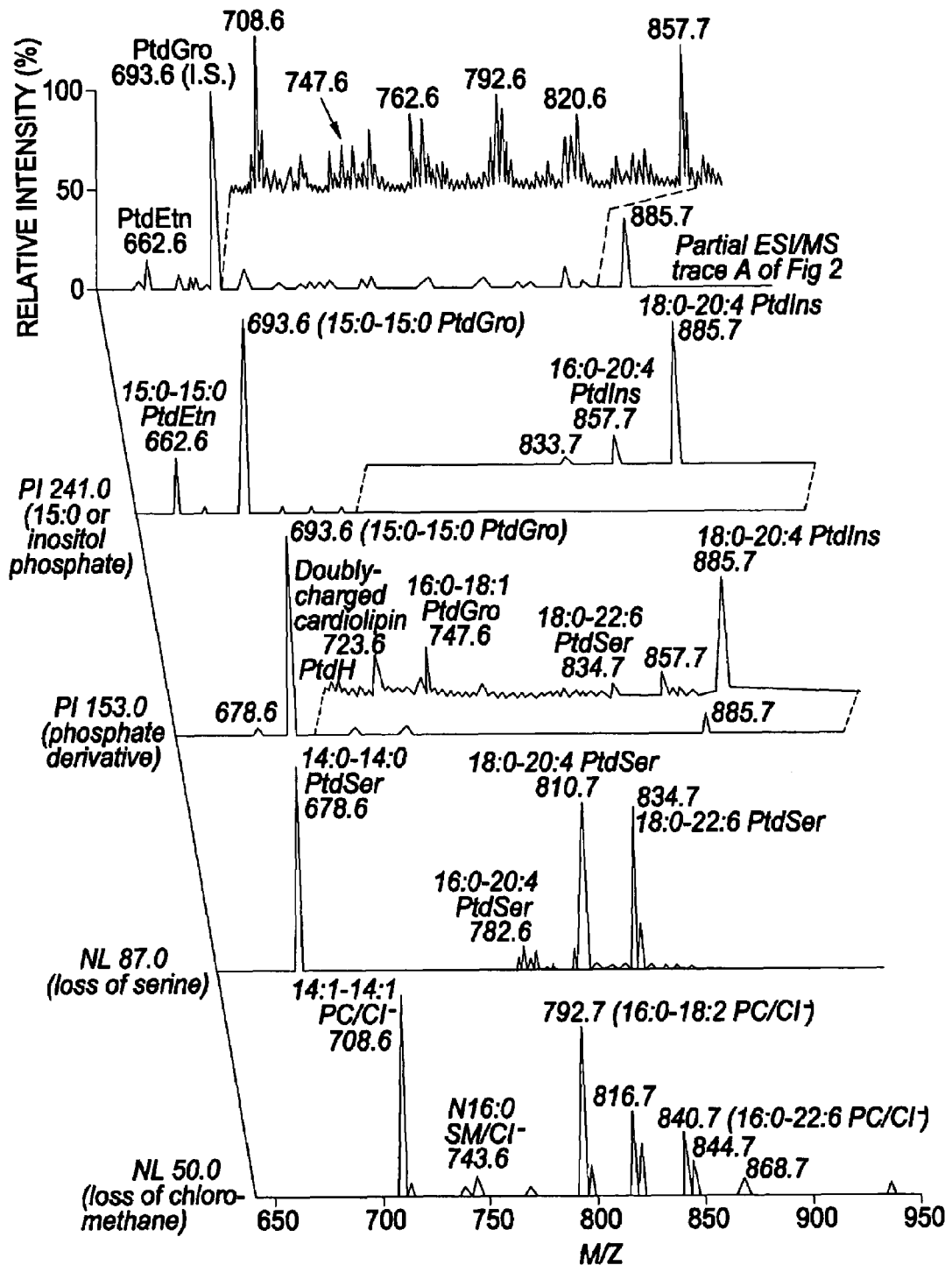
FIG. 9. Two-dimensional electrospray ionization mass spectra of a mouse liver chloroform extract acquired under condition 1. The 2D (or multidimensional ESI/MS) mass spectrum A shows anionic or pseudoanionic lipid molecular species by neutral loss and precursor-ion scanning of their head groups. A conventional ESI mass spectrum was acquired in the negative-ion mode under condition 1 (Trace A of FIG. 8) prior to analysis in the second dimension by precursor-ion scanning of m/z 241.1 (inositol phosphate) or m/z 153.0 (glycerophosphate derivative). Each precursor-ion (PI) scan was acquired by scanning the first quadrupole from m/z 650 to 950 at a rate of 300 amu/s and fixing the third quadrupole at the indicated m/z value. Serine glycerophospholipid molecular species were identified by the neutral loss of serine (87.0 amu). Chlorinated choline glycerophospholipid molecular species were identified by the neutral loss of 50.0 amu resulting from the loss of chloromethane. Each neutral loss (NL) scan was acquired by simultaneously scanning the first and third quadrupoles at a fixed mass difference (neutral loss) at a rate of 300 amu/s while the first quadrupole was scanned over m/z 650 to 950. The 2D (or multidimensional ESI/MS) mass spectrum B was used to identify the acyl chain composition of each anionic or pseudoanionic molecular ion. Each PI scan was acquired by scanning the first quadrupole from m/z 650 to 950 at a rate of 300 amu/s and fixing the third quadrupole at an ion corresponding to a naturally-occurring acyl carboxylate anion. In both NL and PI scans, the second quadrupole acts as a collision cell in which a collision gas pressure of 1 mT was employed. Different collisional energies for each different NL or PI scan are stated in the "Experimental Protocol". All mass spectral traces were displayed after normalization to the most intense peak in each individual spectrum.

First, under condition 1 the diluted chloroform extract of liver is analyzed directly at neutral pH by negative-ion mass spectroscopy of lithium-coordinated species which selects for ionization of anionic lipid species that possess an inherent negative charge (trace A, FIG. 8). The negative-ion mass spectrum of chloroform extracts of hepatic tissues acquired under condition 1 displays a molecular species fingerprint reflecting the presence of multiple lipid molecular ions. To determine the chemical structure and assignments of individual peaks corresponding to the lipid classes and molecular species, either neutral loss or precursor-ion scanning (or both) of head group loss from each of the lipid classes were performed in a 2D (or multidimensional ESI/MS) manner (FIG. 9A). For example, precursor-ion scanning of m/z 241.1 (corresponding to the presence of inositol phosphate) was used to identify phosphatidylinositol (PtdIns) molecular species; neutral loss scanning of 87.0 amu (corresponding to the presence of serine) was used for phosphatidylserine (PtdSer) molecular species; and precursor-ion monitoring of m/z 153.0 (corresponding to a glycerol phosphate derivative) was used to substantiate the assignments of all anionic phospholipids [27, 28, 29, 31] (FIG. 9A). Similarly, neutral loss scanning of 50.0 amu corresponding to the loss of methyl chloride [27] was used to identify chlorinated choline-containing phospholipid molecular species (FIG. 9A). The identity of aliphatic chains in each of these ion peaks was determined by the cross peaks of a 2D (or multidimensional ESI/MS) tandem mass spectrum which consisted of precursor-ion scans of all naturally-occurring fatty acids (FIG. 9B).

Figure 9B:
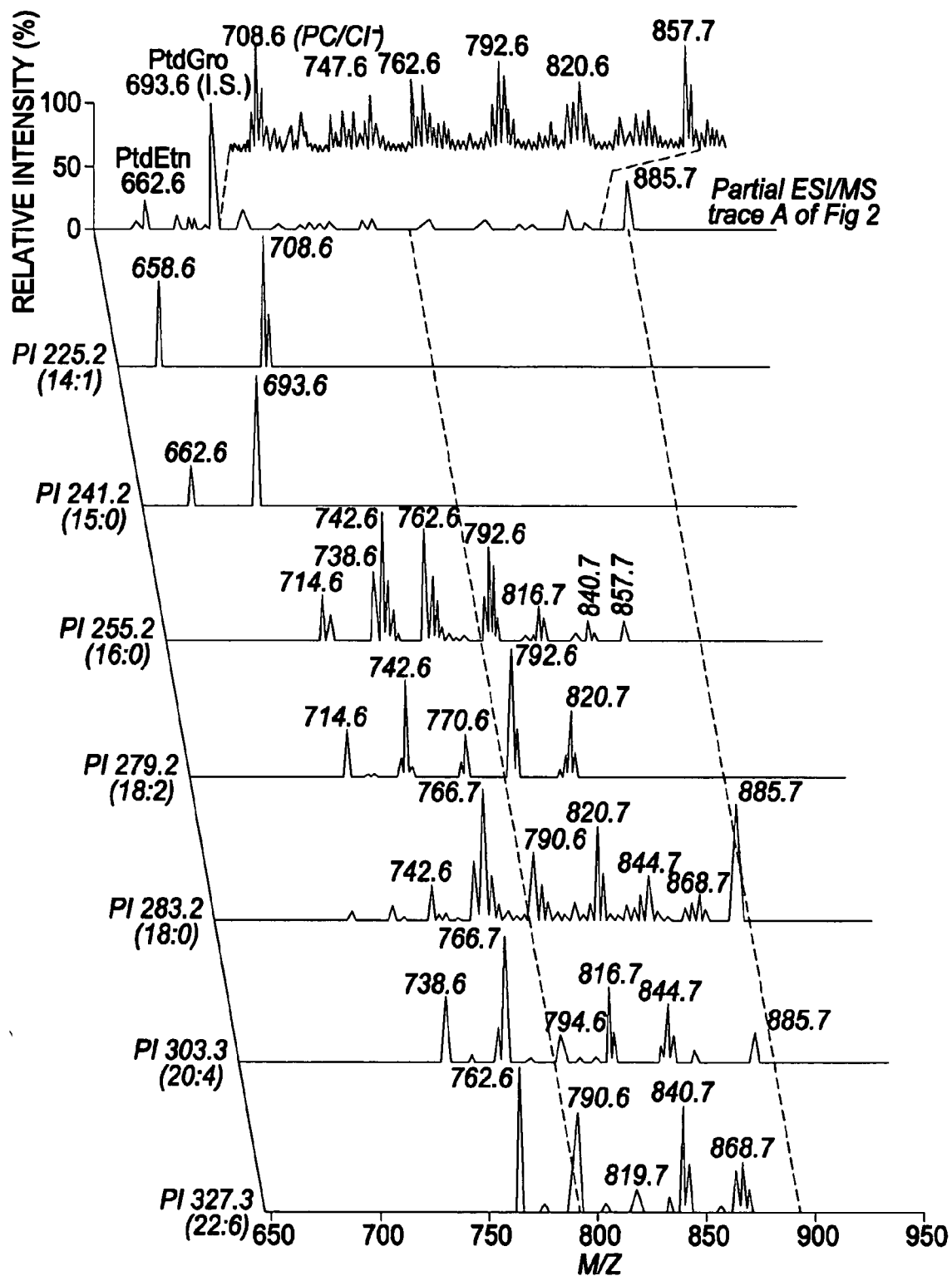

Each of ion cross peaks in each 2D (or multidimensional ESI/MS) mass spectrum provides essential information on the identity of the lipid class (FIG. 9A) and the relative content of the individual molecular species in that class (FIG. 9B). Thus, the molecular species content is actually determined utilizing multiple different approaches from a single lipid extract providing a detailed fingerprint in multiple dimensions of the cellular anionic lipidome. The results in FIGS. 9A and 9B not only identify the molecular species giving rise to the ion peaks in the pseudo 2D (or multidimensional ESI/MS) mass spectrum in FIG. 8, but also resolve isobaric molecular species to identify the fractional percentage of each molecular species contributing to the observed pseudomolecular ions. Through analysis of cross peak intensity ratios in FIG. 9B, the regiospecificity of the aliphatic chains can be determined by previously defined fragmentation kinetics [27]. Information on choline glycerophospholipids (PC) as their chlorine adducts can also be obtained from these 2D (or multidimensional ESI/MS) mass spectra (FIG. 9) and can be used to confirm the molecular species assignments, to resolve the isobaric peaks, and to determine the regiospecificity of the aliphatic chains in each PC molecular species which will be quantitatively analyzed under condition 3 (see below).

Thus, 2D (or multidimensional ESI/MS) mass spectroscopic analyses under condition 1 identified the large majority of individual molecular species of anionic phospholipid classes (e.g., PtdIns, phosphatidylglycerol (PtdGro), PtdSer, cardiolipin, and phosphatidic acid (PtdH)) and pseudoanionic (e.g., chlorinated PC) lipid molecular ions displayed in Trace A of FIG. 8. It was previously demonstrated that the ionization efficiency of anionic lipids (e.g., PtdGro and PtdIns) is identical within experimental error in dilute lipid solutions [25] and that there is a linear relationship between ion intensity and lipid concentration in the low concentration regime [25, 32-35]. Therefore, by comparing the intensity of each ion peak with anionic lipid internal standards (i.e., 15:0 -15:0 PtdGro, m/z 693.6, and 14:0-14:0 PtdSer, m/z 677.6) in Trace A of FIG. 8 and appropriate correction for $^{13}$C isotope effects [36,37] in conjunction with the refinement of low abundance species or species in isobaric ion peaks by using 2D (or multidimensional ESI/MS) mass spectra in FIG. 9, masses of individual molecular ions can be obtained. Through this approach, we found that the mouse liver contained 3.1±0.5, 1.5±0.3, 0.8±0.1, 0.9±0.1, and 0.10±0.02 nmol/mg of protein of PtdIns, PtdSer, PtdGro, cardiolipin, and PtdH, respectively. These values agree closely with previously published values of hepatic lipids in the literature determined utilizing multiple sequential column chromatographic steps which take days as opposed to minutes to perform [38-40]. It is important to remember that pH values can influence the charge states of PtdH and may also affect the distribution of cardiolipin in singly-charged or doubly-charged ionic forms. Thus, similar conditions should be employed and additional internal standards can be used as necessary.

2D (or Multidimensional ESI/MS) Mass Spectrometric Analysis of Hepatic Lipid Classes And Molecular Species under Condition 2

Figure 10A:
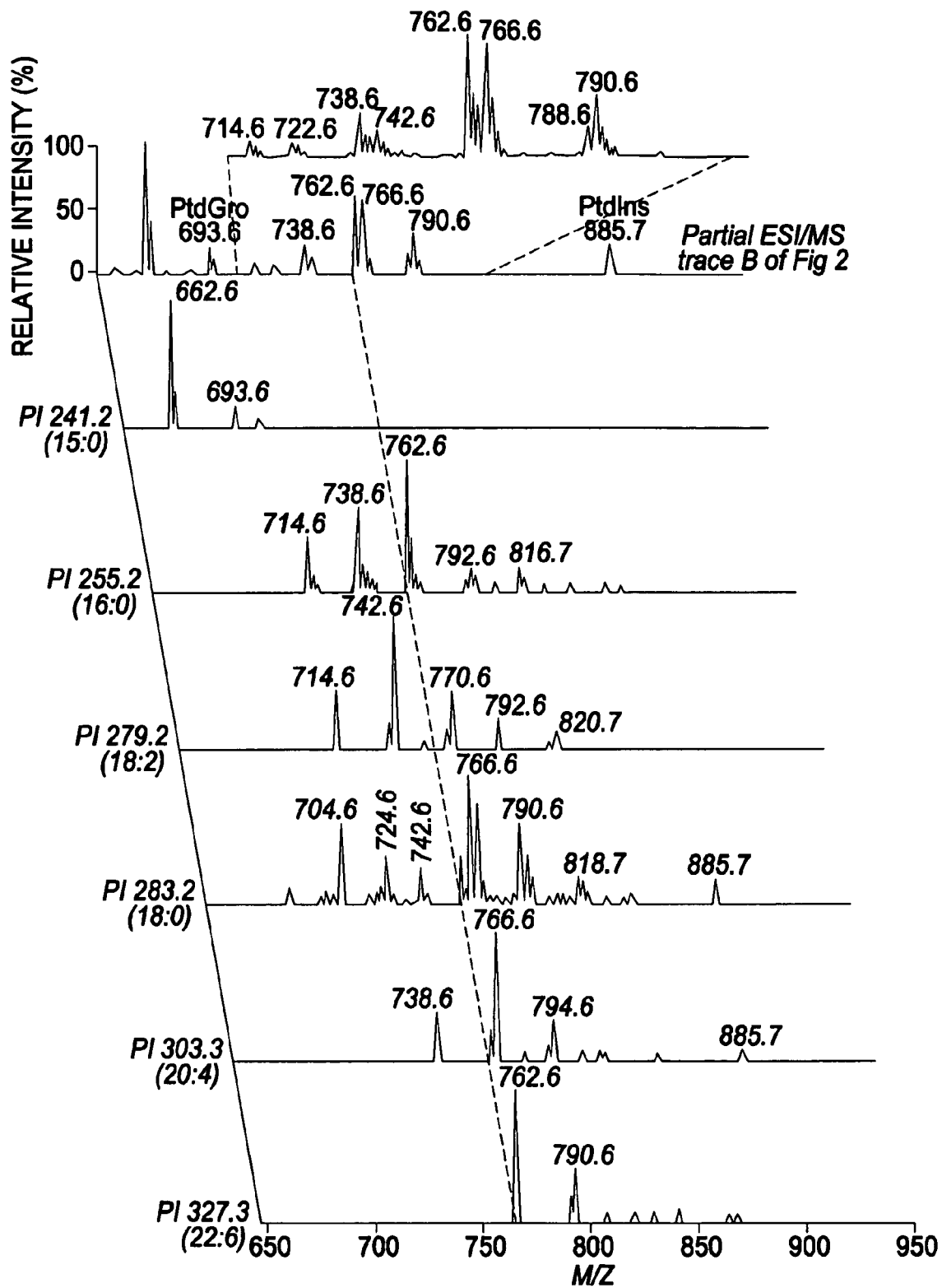
FIG. 10. Two-dimensional electrospray ionization mass spectra of a mouse liver chloroform extract acquired under condition 2. The 2D (or multidimensional ESI/MS) mass spectrum A was used to identify aliphatic chain composition of ethanolamine glycerophospholipid molecular species (under condition 2). After the addition of LiOH to the sample, the first dimension spectrum was obtained (top trace) and individual molecular species were quantified by comparisons with internal standard. Next precursor-ion (PI) scan of representative aliphatic chains was utilized to confirm the molecular species assignments, identify isobaric molecular species, and provide additional quantitative information on the regiospecificity of the aliphatic chains. Each PI scan was acquired by scanning the first quadrupole from m/z 650 to 950 at a rate of 300 amu/s and fixing the third quadrupole at an ion corresponding to a naturally-occurring acyl carboxylate anion. The 2D (or multidimensional ESI/MS) mass spectrum B was used to identify and quantitate ceramide molecular species. Under condition 2, the first dimension spectra from m/z 500 to 680 did not reveal peaks corresponding to the molecular masses of known ceramides. However, neutral loss (NL) scanning of either 327.3 amu (specific for 2-hydroxy ceramides), 256.2 amu (highly sensitive for nonhydroxy ceramides), or 240.2 amu (equally sensitive for both hydroxy and nonhydroxy ceramides) easily identify and quantify multiple ceramide molecular species. Each NL scan was acquired by simultaneous scanning of the first and third quadrupoles at a fixed mass difference (neutral loss) at a rate of 300 amu/s while the first quadrupole was scanned over m/z 500 to 680. The second quadrupole was used as a collision cell in which a collision gas pressure of 1 mT was employed. Different collisional energies for each different NL or PI scan are stated in the "Experimental Protocol". All mass spectral traces were displayed after normalization to the base peak in the individual spectrum.
Figure 10B:
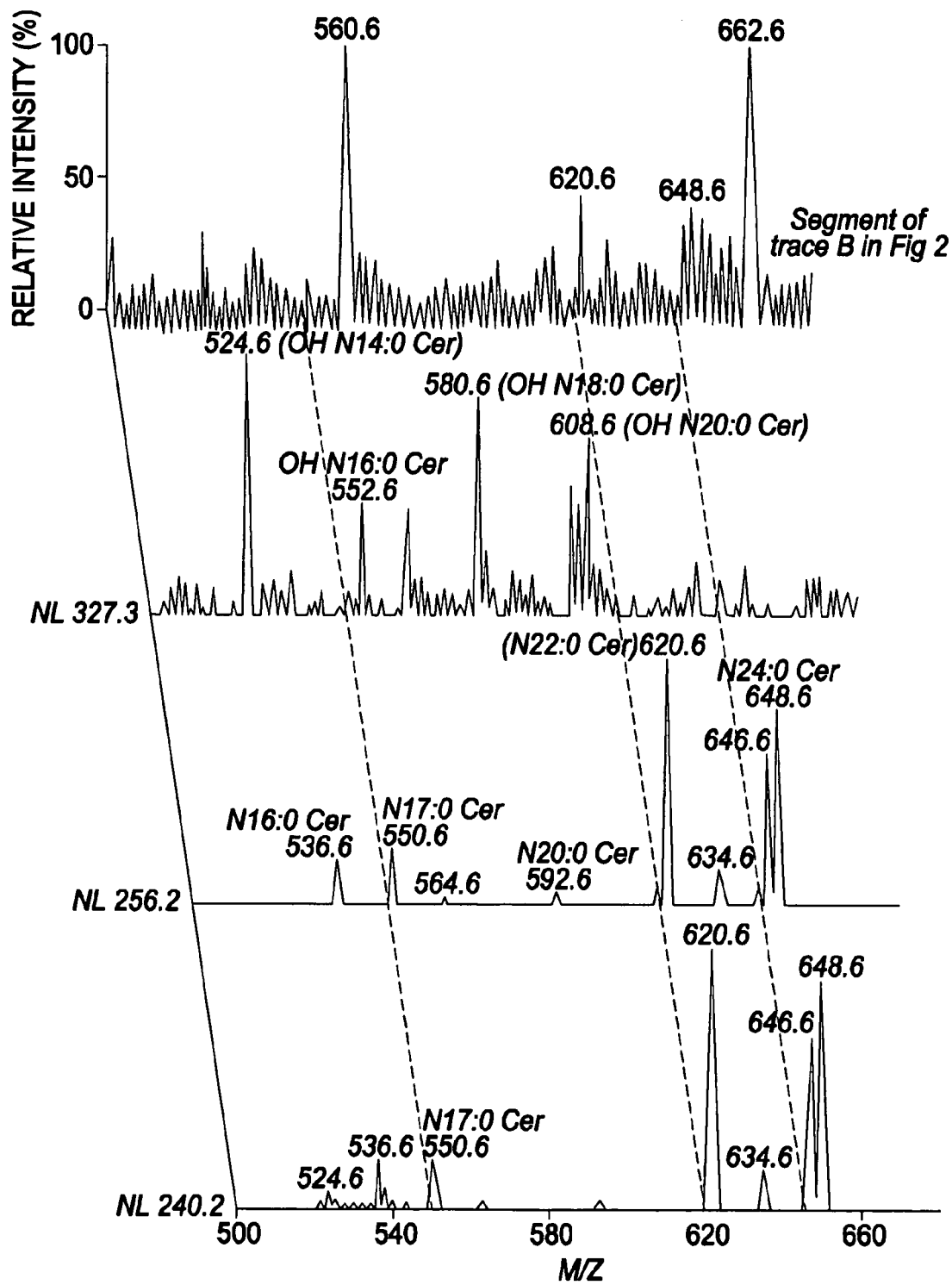

Next, in the presence of LiOH (FIG. 7), zwitterionic ethanolarnine glycerophospholipid (PE) molecular species are rendered anionic by deprotonation of their positively-charged amine. Negative-ion ESI results in abundant pseudomolecular ion peaks corresponding to individual PE molecular species which are quantified by comparison of their ion peak intensities with that of their internal standard (i.e., 15:0-15:0 PtdEtn) in Trace B of FIG. 8 after correction for $^{13}$C isotope effects [36,37]. Since alkalization by addition of LiOH results in the production of the lithium salt of doubly-charged PtdSer, PE molecular species are now readily resolved from their PtdSer counterparts. Other classes of anionic lipids (e.g., PtdGro and PtdIns) do not overlap with PE species since their endogenous masses are well separated from ethanolamine glycerophospholipid species (top trace) and due to the nitrogen rule. Moreover, the amounts of each of these anionic phospholipids are quite small in comparison to the mass of PE species. The chemical identities of these peaks (and underlying isobaric molecular species) can be readily determined by 2D (or multidimensional ESI/MS) mass spectrometry employing precursor-ion scanning of all naturally-occurring aliphatic chains. Inspection of the precursor ion scans readily identify the peaks at m/z 762.6 as 16:0-22:6 PtdEtn, the peak at m/z 766.6 as 18:0-20:4 PtdEtn and the peak at m/z 790.6 as 18:0-22:6 PtdEtn (FIG. 10A). There are 30.3±1.3 nmol PE/mg of protein in the liver homogenates with major peaks at m/z 762.6 (present in 11.0±0.9 nmol/mg of protein by comparison with PE internal standard), m/z 766.6 (9.9±0.9 nmol/mg of protein), and m/z 790.6 (4.91±0.44 nmol/mg of protein). The individual molecular species composition of minor PE molecular species corresponding to low intensity peaks (and underlying isobaric species) could be carefully refined by 2D (or multidimensional ESI/MS) mass spectrometry employing precursor-ion scanning of all naturally-occurring aliphatic chains (FIG. 10A). These measurements confirm the composition of the acyl moieties, identify their regiospecificity, and deconvolute the relative contributions of isobaric molecular species. Through precursor-ion scanning of naturally-occurring aliphatic chains, the cross peaks at each molecular species are in relative proportion to the mass abundance of that aliphatic chain in the PE class of lipids (FIG. 10A).

Similarly, under condition 2, non-esterified fatty acids (NEFA) exist as their lithium coordinated carboxylate anions in solution. Thus, abundant pseudomolecular ion peaks corresponding to NEFA molecular species are apparent (Trace B of FIG. 8). Through this approach, NEFA molecular species can be directly quantitated by comparisons of their ion peak intensities with that of their internal standard (i.e., 20:0 FA) after correction for $^{13}$C isotope effects. It was found that there are 35.4±3.0 nmol NEFA/mg protein in the liver homogenates.

The amide proton in ceramide molecular species is partially removed by base under condition 2, allowing ceramides to be directly quantitated by comparisons with a ceramide internal standard. However, since most tissues contain only diminutive amounts of ceramide, we have developed a 2D (or multidimensional ESI/MS) tandem mass spectrometric approach to reduce background noise to measure ceramide molecular species (FIG. 9B). For analysis of ceramide molecular species containing 18-carbon sphingosine, neutral loss scanning greatly facilitates the identification and quantification of these low abundance constituents. Since the low abundance of ceramide requires background elimination, tandem mass spectrometric scanning for neutral loss of 327.3 amu (for hydroxy ceramides) or 256.2 amu (for nonhydroxy-containing ceramides) is typically employed. As can be seen both hydroxy- and nonhydroxy-containing substituents can be easily determined (Panel E of FIG. 7 and FIG. 10B). For quantitation, neutral loss scanning of 240.2 amu (corresponding to the loss a 2-trans-palmitoleyl alcohol) can be employed which is not sensitive to variations in the acyl chain substituent [36]. There was a total of 505±12 pmol of ceramide/mg of protein present in liver homogenates.

2D (or Multidimensional ESI/MS) Mass Spectrometric Analysis of Heptic Lipid Classes And Molecular Species under Condition 3

Figure 11A:
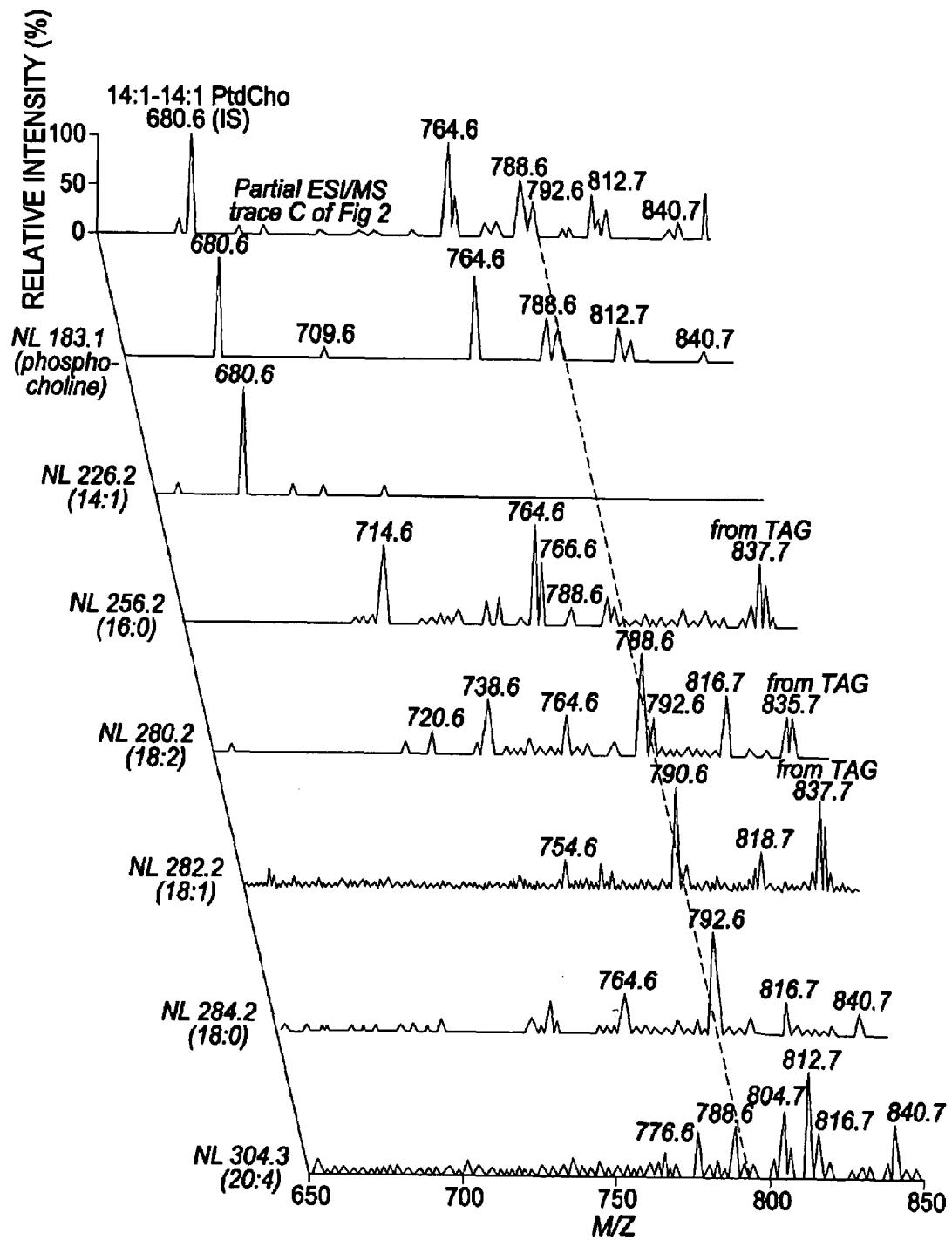
FIG. 11. Two-dimensional electrospray ionization mass spectra of a mouse liver chloroform extract acquired under condition 3. The 2D (or multidimensional ESI/MS) mass spectrum A shows choline-containing phospholipids analyzed by neutral loss of their head group and aliphatic chains. After the addition of LiOH to the sample, a first dimension spectrum was obtained (top trace) in the positive-ion mode (Condition 3) and individual molecular species were quantified by comparisons with selected internal standards. Next, neutral loss scanning of representative aliphatic chains or phosphocholine was utilized to confirm the molecular species assignments and identify isobaric molecular species. Each neutral loss (NL) scan was acquired by simultaneous scanning of the first and third quadrupoles at a fixed mass difference corresponding to the neutral loss of either a phosphocholine (NL 183.1) or a naturally-occurring fatty acid, respectively. The first quadrupole was scanned in a mass range of PC molecular species (m/z 650 to 850) at a rate of 300 amu/s. The 2D (or multidimensional ESI/MS) mass spectrum B shows an analogous approach for triacylglycerol molecular species analysis utilizing neutral losses. After the addition of LiOH to the sample, a first dimension spectrum was obtained (top trace) in positive-ion mode (Condition 3). Next neutral loss scanning of all naturally-occurring aliphatic chains was utilized to confirm the molecular species assignments, identify isobaric molecular species, and quantify triacylglycerol individual molecular species by comparisons with a selected internal standard. Each NL scan was acquired by simultaneous scanning of the first and third quadrupoles at a fixed mass differences corresponding to neutral loss of a naturally-occurring free fatty acid. The first quadrupole was scanned through the mass range of TAG molecular species (m/z 800 to 950) at a rate of 300 amu/s. The second quadrupole was used as a collision cell in which a collision gas pressure of 1 mT was employed and a collisional energy of 35 eV was applied. All mass spectra were displayed after normalization to the most abundant peak in the individual spectrum.
Figure 11B:
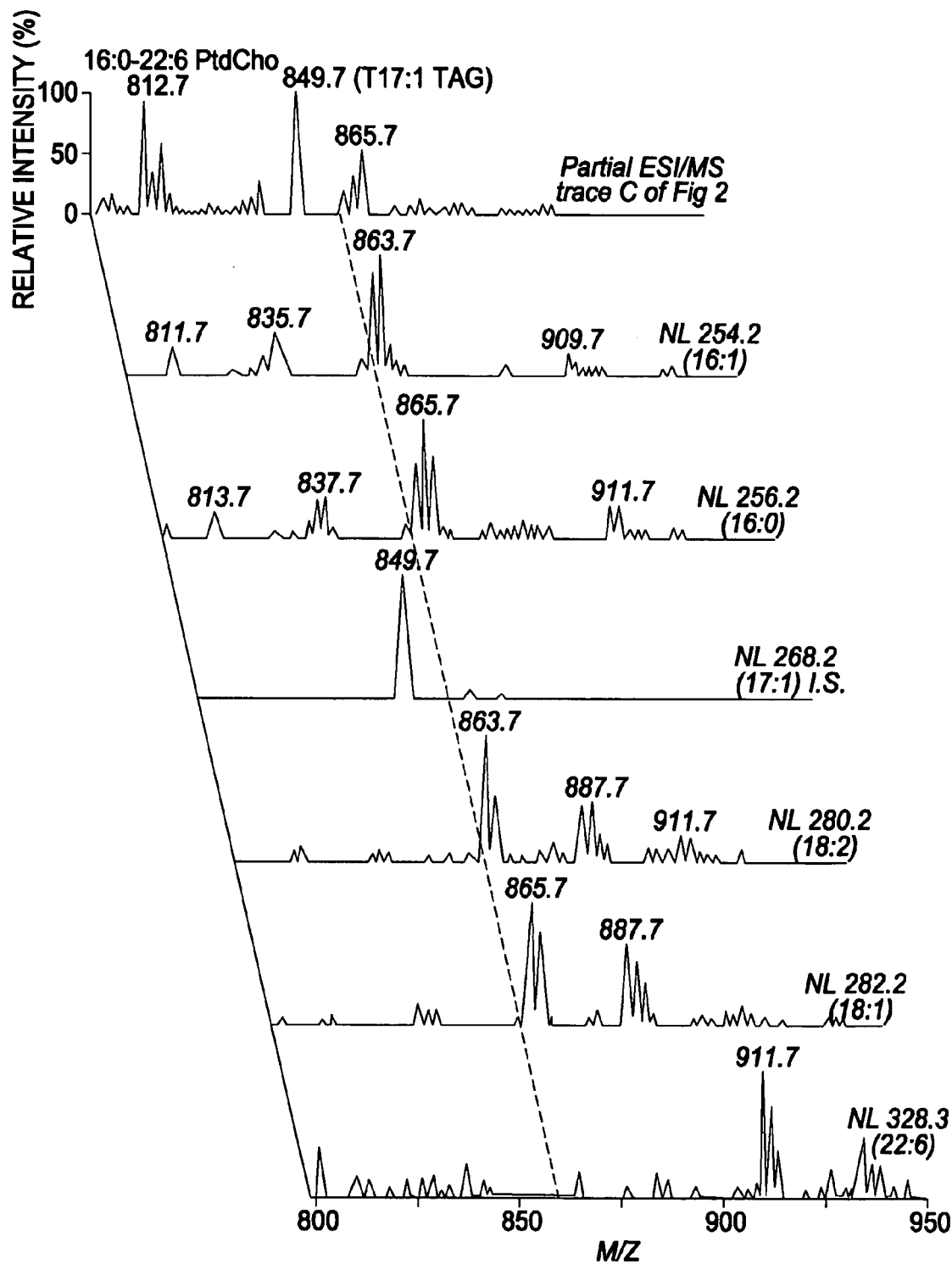

Under condition 3, the dilute chloroform extract is at alkaline pH and the mass spectrometer's ion source is switched to the positive-ion mode. By selecting positive ions, molecular species of PC and TAG are readily ionized while molecular classes which contain a negative charge (including anionic lipids and PE species) are largely prevented from forming positively-charged ions during the electrospray ionization process. Accordingly, the positive-ion mass spectrum contains ion peaks corresponding to lithiated phosphocholine-containing molecular species (PC, SM and minor amounts of lysophosphatidylcholine (lysoPtdCho)) and TAG molecular species (Trace C of FIG. 8). The contents of PC, SM, and lysoPtdCho molecular species were quantified by comparison of their ion peak intensities with that of their corresponding internal standards. We found 45.3±1.1, 3.5±0.4, and 1.8±0.2 nmol PC, SM, and lysoPtdCho/mg of protein in liver homogenates, respectively, which again agree well with previously published values of hepatic lipids in the literature determined utilizing multiple sequential column chromatographic steps [38-40]. The identities of PC and SM individual molecular species can be confirmed and their relative abundance can be redundantly determined by 2D (or multidimensional ESI/MS) mass spectrometry using either condition 1 or 3 in conjunction with 2D (or multidimensional ESI/MS) neutral loss scanning or precursor-ion scanning (FIGS. 9A and 11A). Furthermore, discrimination of SM and PC molecular species has been made either by nitrogen role or by comparisons of the tandem mass spectra acquired under conditions 1 and 3 with the mass spectrum obtained under condition 3. In tandem mass spectra, ion peaks corresponding to the SM molecular species are markedly enhanced relative to the ion peaks of PC species due to the differential fragmentation pattern of PC and SM species previously demonstrated [27].

In addition to the identification of phosphocholine-containing molecular species under condition 1 (FIG. 9), phosphocholine-containing molecular species can be quantified in the positive-ion mode under condition 3. A 2D (or multidimensional ESI/MS) approach under condition 3 provides additional information for confirmation of the molecular identities of choline-containing phospholipids species and their relative abundance. Moreover, neutral loss scanning for the phosphocholine head group (neutral loss of 183.1 amu) or naturally-occurring aliphatic chains give rise to background free spectra demonstrating the relative mass representation of phosphocholine-containing molecular species as well as each aliphatic chain in individual molecular species of choline glycerophospholipids (FIG. 11A).

For triacylglycerol analysis, neutral loss scanning represents a special case since numerous isobaric peaks are present which preclude molecular species determination by product-ion analysis alone. The 2D (multidimensional) mass spectrometric approach utilizing neutral loss analyses of all potential naturally-occurring fatty acids in TAG species contains critical information on the amount and identity of TAG molecular species (FIG. 11B) as previously described [34]. For example, the abundant cross ion peaks at m/z 865.7 present in the neutral loss scanning of 254.2, 256.2, 280.2, and 282.2 amu (the broken line in FIG. 11B), demonstrate that the ion peak at m/z 865.7 was an isobaric peak comprised of lithiated 16:1-18:1-18:1 and 16:0-18:1-18:2 TAG species. We have identified at least 21 abundant TAG species in mouse liver (the present method does not distinguish regioisomers). The total amount of TAG in mouse liver homogenates is 11.1±0.9 nmol/mg of protein.

Discussion

The multi-dimensional mass spectrometric approach described in this study allows the sensitive, rapid, and detailed fingerprinting of hundreds of individual molecular species of lipids. Through multiple complimentary 2D and multidimensional approaches, the molecular species composition is directly identified and the mass content can be iteratively and redundantly refined after it is initially determined from values obtained in first dimensional mass spectra. The benefits of this 2D (or multidimensional ESI/MS) mass spectrometric approach include definitive peak assignments substantiated by multiple independent mass spectrometric criteria, a dramatic reduction in background noise (which is especially useful for identification and refined quantitation of low abundance molecular species) and the direct discrimination of contributing isobaric molecular species. Through this approach, changes in cellular lipidomes in response to disease states, pharmacological therapy, or cellular nutrient status can be identified leading to insights into lipid-mediated disease processes. The data stream from the spectrometer using these approaches is readily adaptable to automated analysis utilizing appropriate weighting algorithms. A 3D configuration of ESI mass spectrum can thus be executed by data herein through combining 2D (or multidimensional ESI/MS) mass spectra for head group analysis with additional spectra of acyl chain distributions. Computer analysis of these 2D (or multidimensional ESI/MS) or 3D mass spectra, in conjunction with algorithms for weighted combinations of appropriate refinements, can thus provide the foundation for automated multiple dimensional mass spectrometry of lipids and other cellular constituents.

ESI tandem mass spectrometry has previously demonstrated its utility for the elucidation of lipid classes, individual molecular species, and even regioisomers [26, 27, 28, 29, 31, 41-44]. We utilized previously developed scanning modes in combination with newly developed ones to provide an integrated platform exploiting the intrasource separation technique to serve as a foundation for development of methods for the detailed study of cellular lipidomes. The traditional ID mass spectroscopic approach requires hundreds of operator-initiated individual analyses to assign the chemical composition and regiospecificity of aliphatic chains. In contrast, the utilization of these 2D (or multidimensional ESI/MS) techniques allows the identification of aliphatic chains in the peaks of interest by a high throughput approach from a platform suitable for automation and automated data analysis. Moreover, the present method excludes contamination of ions resulting from the presence of naturally occurring $^{13}C$ in closely neighboring peaks. The practical utility of this effect can be seen from direct examination of spectra of PC and TAG (condition 3) which both contribute ions to the observed peak at m/z 813.7 (M+1 for PC and M for TAG). In operator-initiated examination of this peak by collision-induced dissociation, contributions of aliphatic chains in PC molecular species (M+1) would be present at m/z 813.7 resulting from $^{13}C$ isotope effects. In contrast, with the 2D (or multidimensional ESI/MS) techniques presented, direct assessments of aliphatic chain composition are possible without contributions from neighboring peaks. By using this 2D (or multidimensional ESI/MS) approach, the identification of ether lipids now can become routine providing new technology to study the role of ether lipids in signaling processes and human disease. Moreover, discrimination of SM and PC molecular species using the 2D (or multidimensional ESI/MS) approach is now obvious, providing investigators with new tools to study sphingolipid functions in plasma membrane and lipid rafts and its interactions with cholesterol.

In our very early studies, we found a linear relationship between ion intensity and lipid concentration in the low lipid concentration regime where ionization efficiency largely depends on the nature of the polar head group of lipids (25). As an extreme case, we examined the relationship between 16:0 lysoPtdCho and 16:0-16:0 PtdCho. Addition of selected amounts of 16:0 lysoPtdCho to a solution of containing 16:0-16:0 PtdCho resulted in a linear correlation between their molar ratio and the ratio of their respective sodiated ion peak intensities in positive-ion mode after correction for $^{13}C$ isotope effects with a slope of 1.00 and a correlation coefficient factor ($\gamma^2$) of 0.998 [25]. This linear relationship was independently demonstrated by multiple other investigators [25, 32-35]. Therefore, this relationship serves as a benchmark for the quantitative ESI/MS analysis of lipid molecular species in one class using only one internal standard with ±5% of accuracy after correction for $^{13}C$ isotope effects. If additional accuracy is sought, other structurally similar lipids should be utilized as internal standards as necessary.

However, we stress and have emphasized that this liner relationship is valid only at low concentrations of lipid in the infusion solution in which lipid-lipid interactions and ion suppression are rare [25]. When the concentration of lipids in the infusion solution increases to the point where lipid-lipid interactions predominate, the effects of acyl chain length and unsaturation on lipid quantitation become apparent. This is largely due to lipid-lipid interactions which are highly dependent on the physical properties of the lipids under study. A linear relationship in the low concentration regime, as well as a nonlinear and structure-dependent relationships in the high concentration regimes, have been recently demonstrated [34-35]. Another reason underlying nonlinear relationships is that the effects of $^{13}C$ isotope on the quantitation have not been considered by most investigators. This results in a decline in ion intensity as the chain length increases (i.e., type I $^{13}C$ isotope effect) or due to a random influence from the type II $^{13}C$ isotope effects [36, 37]. It needs to be emphasized that quantitation of lipid molecular species using tandem mass spectrometry must be made with caution and appropriate justifications since fragmentation kinetics can be substantially different depending on the collisional activation energy employed and the structure of individual molecular species under study [27, 35, 37, 45]. We also point out another advantage of this 2D (or multidimensional ESI/MS) approach is to ratiometrically compare the relative amounts of molecular species in different states, such as health and disease. Since the relative fragmentation rates of identical molecular species reflects the intrinsic chemical properties of the species in dilute solution, ratiometric comparison of molecular species from a given class can provide important clues to molecular mechanisms underlying the disease process under study.

Collectively, this study presents a 2D (or multidimensional ESI/MS) ESI mass spectrometric approach for the analyses of the global lipidome in biological samples. Through quantitation of each class of lipids in an ESI mass spectrum by comparisons to internal standards which possess well-defined ionization and fragmentation characteristics similar to the molecules of interest, quantification can be readily performed. This 2D (or multidimensional ESI/MS) ESI mass spectrometric approach can be readily automated to provide a platform for fingerprinting thousands of lipid molecular species to provide new insights into the mechanisms through which alterations in lipid metabolism mediate lipotoxicity and provide a rapid method to assess the effects of diet or pharmacotherapy on lipid metabolism in multiple disease states.

Figure 12:
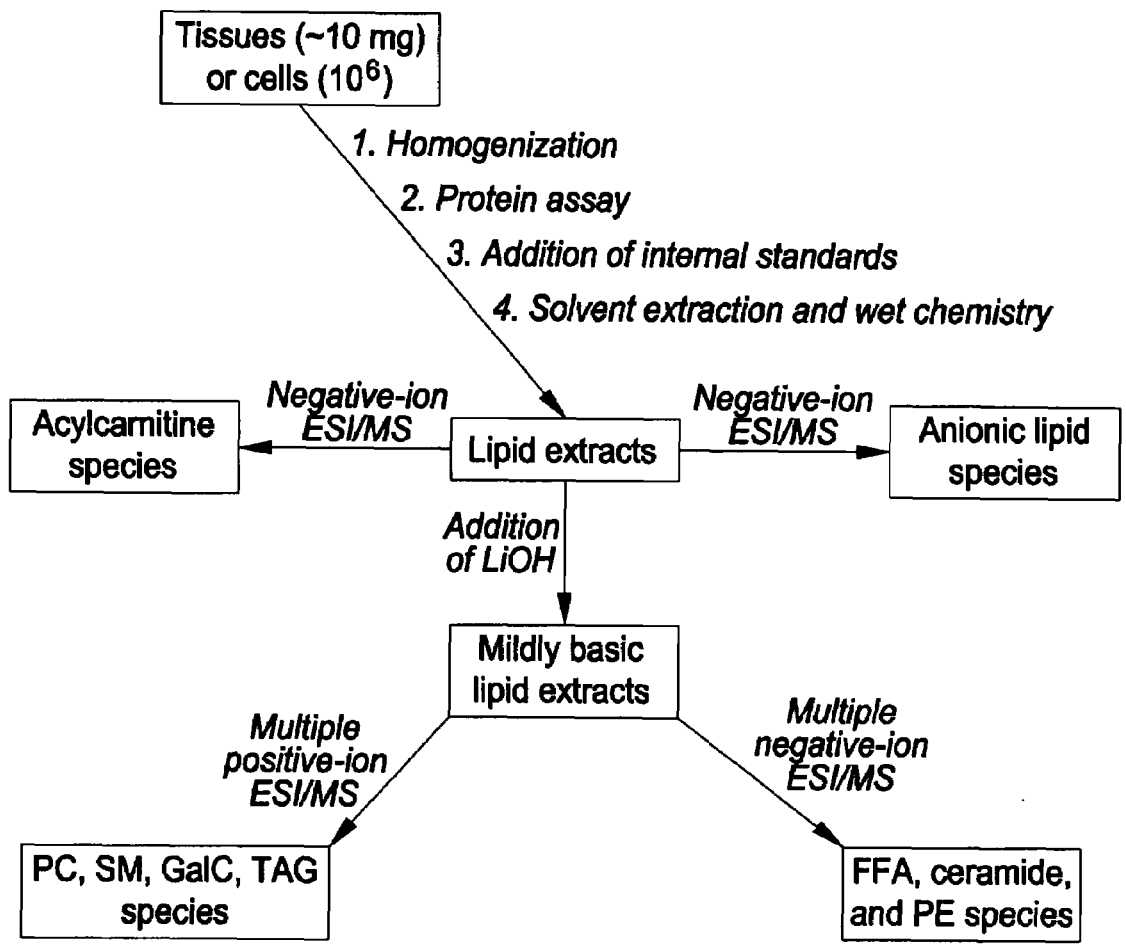
FIG. 12. Schematic diagram of the experimental strategy used for global analyses of cellular lipidomes directly from crude extracts of biological samples.

A commonly-used strategy for lipidome analyses from different biological samples without the need for prior chromatographic separation of lipidomes is illustrated in FIG. 12. Anionic lipids including cardiolipin, phosphatidylglycerols (PtdGro), phosphatidylinositols (PtdIns), phosphatidylserines (PtdSer), phosphatidic acids (PtdH), and sulfatides in the diluted chloroform extracts of biological samples can be analyzed by negative-ion ESI-MS and quantitated by comparisons of the individual ion peak intensity with an internal standard (e.g., 14:0-14:0 PtdGro for anionic phospholipids or N16:0 sulfatide for sulfatides) after correction for $^{13}$C isotope effects relative to the internal standards as described (26, 49) (see ref. 36 for considerations for $^{13}$C isotope effects). Previously, it has been demonstrated that different molecular species of anionic phospholipids have nearly identical ionization efficiencies after corrections for $^{13}$C isotope effects (±10%) for molecular species containing acyl chains with 14 to 20 carbons and different numbers of double bonds (25). A typical negative-ion ESI/MS mass spectrum of a mouse myocardial lipid extract (FIG. 13A) demonstrates multiple abundant anionic phospholipid molecular species which has been identified by tandem mass spectrometry (27, 28). It should be noted that ESI/MS was utilized instead of ESI tandem mass spectrometry for quantitation of lipidome since the latter technique results in differential fragmentation rates for individual molecular species containing different acyl constituents which are highly sensitive to the collisional activation energy employed (28, 36, 37, 45).

Figure 13A:
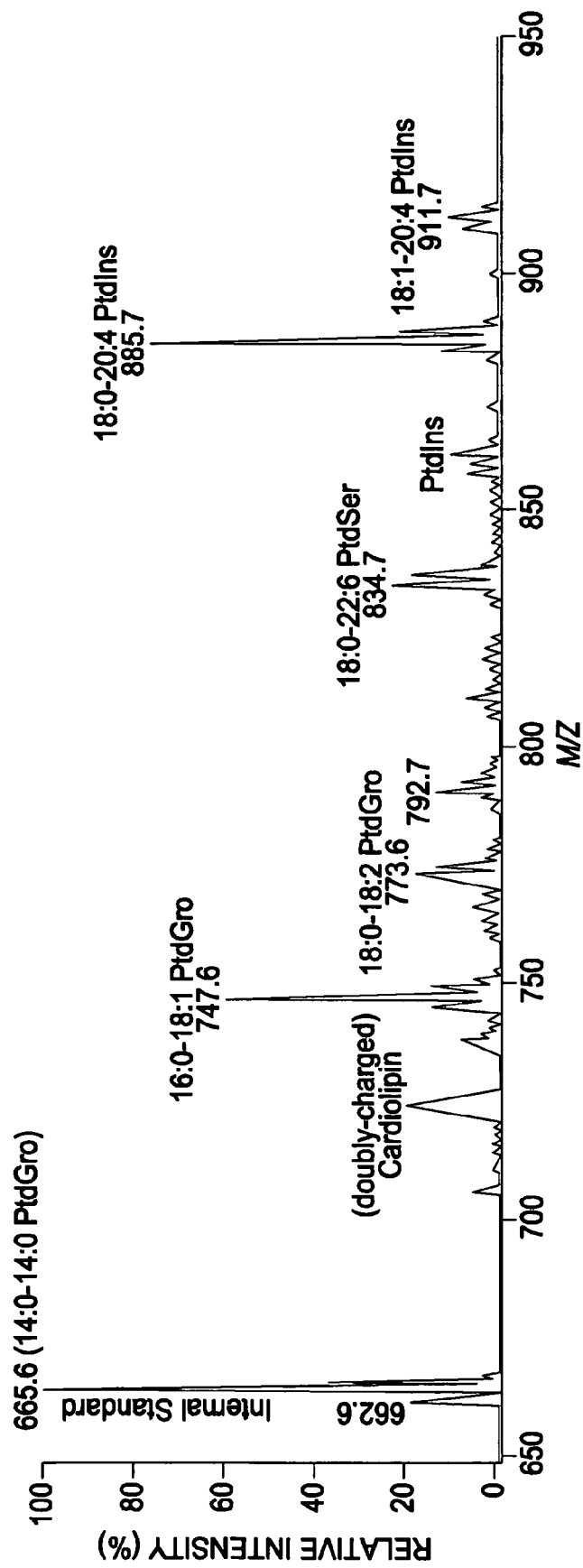
FIG. 13. Electrospray ionization mass spectra of a mouse myocardial lipid extract. Panel A shows a negative-ion ESI mass spectrum in the absence of LiOH in the lipid extract. Panels B and C show negative- and positive-ion ESI mass spectra of the lipid extract after addition of LiOH, respectively. Mouse myocardial lipids were extracted by a modified Bligh and Dyer method. The identities of all indicated molecular species have been confirmed by ESI tandem mass spectrometry.
Figure 13B:
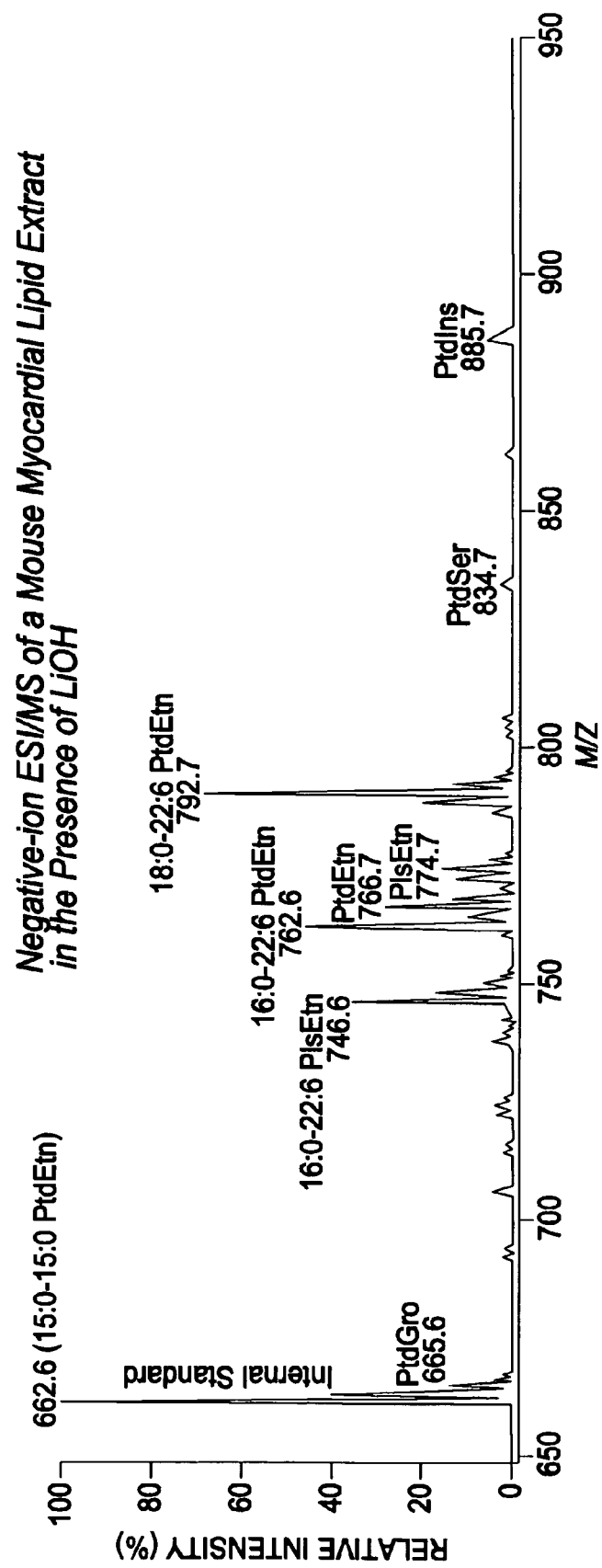

Prior to the analyses of galatocerebrosides (GalC), choline glycerophospholipids (PC), ethanolamine glycerophospholipids (PE), sphingomyelins (SM) in the diluted lipid extracts, LiOH in methanol (50 nmol/mg of protein) is usually added to each individual cellular extract of biological samples to supply counter ions for GalC, PC, and SM analysis and to turn PE molecular species into anionic phospholipids, thereby achieving the separation of lipid classes in electrospray ion source (FIG. 12). PE molecular species can then be directly quantitated by comparison with an internal standard (e.g., 15:0-15:0 PtdEtn) after correction for $^{13}$C isotope effects relative to the internal standard by ESI/MS in negative-ion mode (FIG. 12). A typical negative-ion ESI/MS mass spectrum of the mouse myocardial lipid extract (the identical extract used for the acquisition of FIG. 13A) after addition of a small amount of LiOH displays multiple abundant PE molecular species (FIG. 13B). Identification of ion peaks containing phosphoethanolamine can be achieved utilizing precursor-ion analysis as described previously (28). Acyl chain(s) of each individual PE molecular species can be identified either utilizing product-ion ESI tandem mass spectrometry as previously described (27) or employing an efficient two-dimensional fingerprinting technique by ESI tandem mass scanning of all potential acyl carboxylate ions in the precursor-ion mode. A typical two-dimensional precursor-ion fingerprint (FIG. 14) demonstrates different acyl chain constituents of PE molecular species of a mouse myocardial lipid extract (the identical extract used for the acquisition of FIG. 13B). Quantification of ion peaks corresponding to multiple individual molecular ions can be substantiated utilizing product-ion ESI tandem mass spectrometric analyses as described previously (27). Plasmenylethanolamine (PlsEtn) molecular species can be distinguished from alkyl-acyl phospholipid molecular species by treating lipid extracts with acidic vapors prior to mass spectrometric analyses as described previously (50).

PC and SM molecular species in the diluted tissue extracts can be directly quantitated as their lithium adducts by comparison with an internal standard (e.g., lithiated 14:1-14:1 PtdCho) after correction for 13C isotope effects relative to the internal standard in the positive-ion mode (FIG. 12). GalC molecular species in the diluted tissue extracts can also be directly quantitated as their lithium adducts by comparison with an internal standard (e.g., lithiated d35-N18:0 GalC) after correction for $^{13}$C isotope effects relative to the internal standard in the positive-ion mode (FIG. 12). Individual molecular species can be identified by tandem mass spectrometry (27, 28, 43). A typical positive-ion ESI/MS mass spectrum of a mouse myocardial lipid extract (the identical extract used for the acquisition of FIG. 13B) demonstrates multiple abundant choline-containing phospholipid molecular species (FIG. 13C).

Figure 15A:
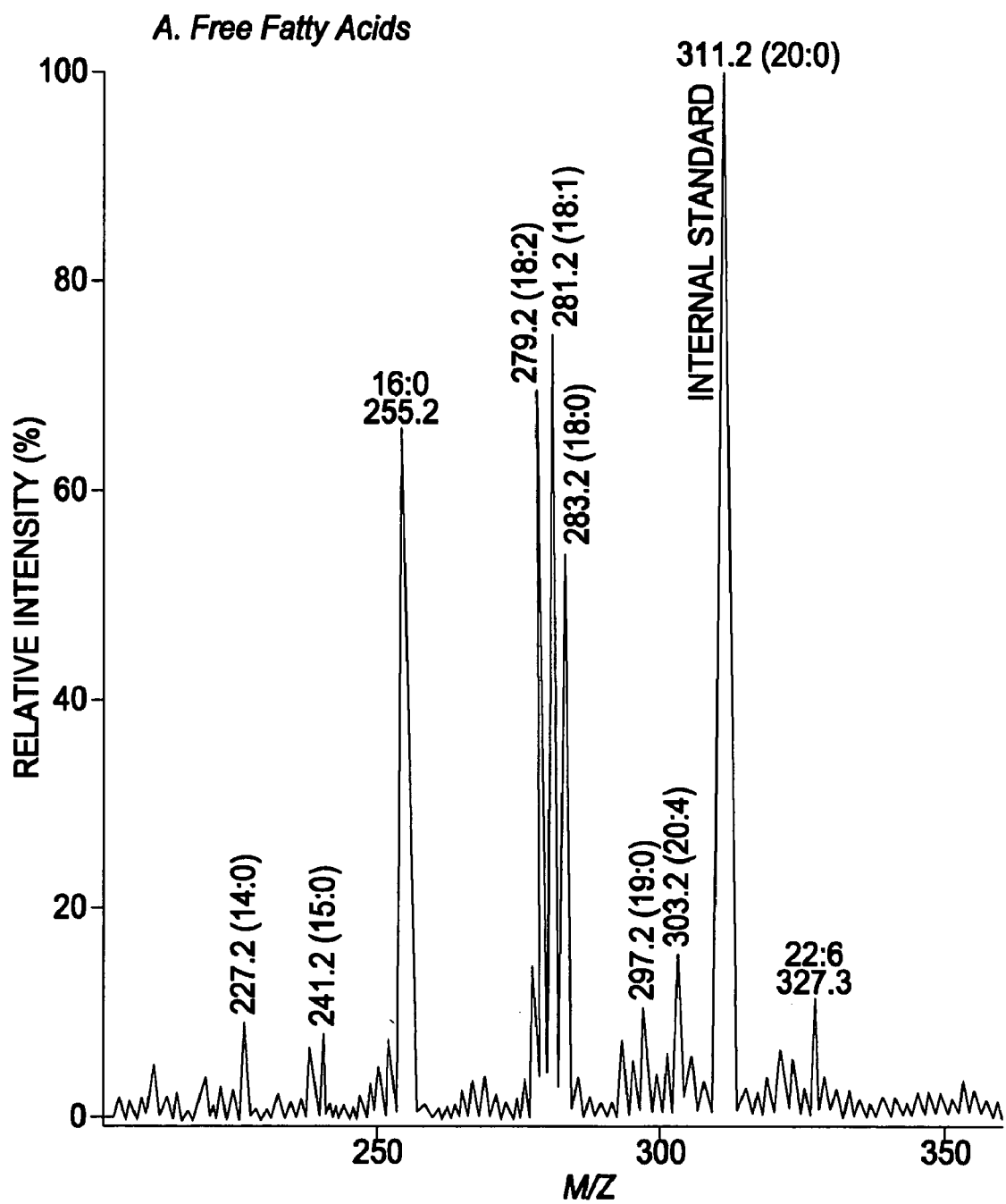
FIG. 15. Quantitative analyses of free fatty acid and ceramide molecular species by electrospray ionization mass spectrometry. Negative-ion ESI mass spectrum (Panel A) of the identical extract after addition of LiOH used in FIG. 13 demonstrates multiple free fatty acid molecular species in the extract. Negative-ion ESI neutral loss scanning of 240.2 u (Panel B) of the identical lipid extract after addition of LiOH demonstrates multiple ceramide molecular species.
Figure 15B:
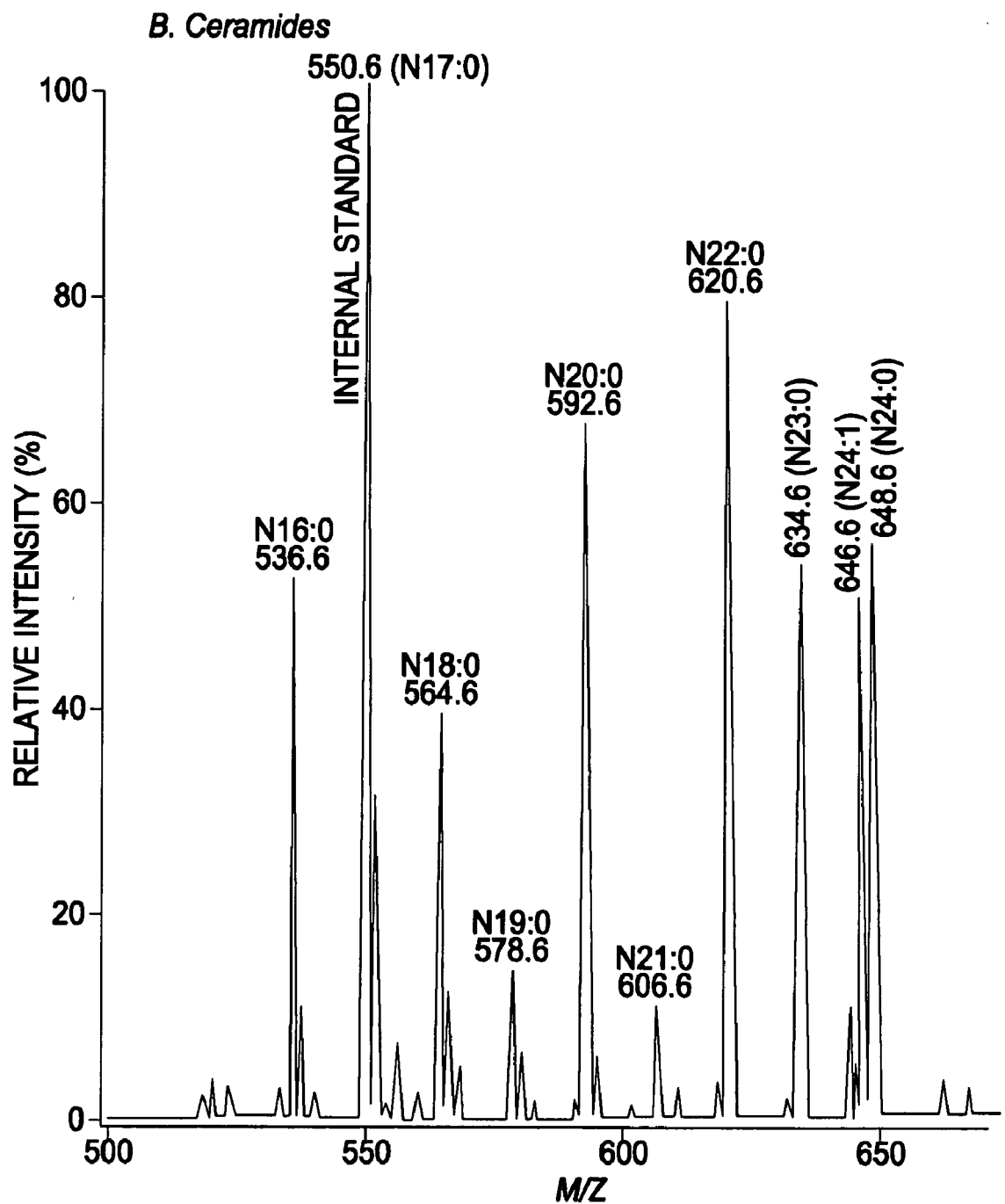

Due to the low abundance of some lipid metabolites (less than a few percents of total lipids) in lipid extracts of biological samples, either special sample preparations or separate ESI/MS analyses typically need to be performed. For example, after rendering the lipid extract solution basic by addition of a small amount of LiOH in methanol, free fatty acids (FFA) in solution will be converted to their carboxylate anion and can be easily quantified by ESI/MS in negative-ion mode scanning through the mass range from 200 to 400. Therefore, quantification is easily accomplished utilizing an internal standard (e.g., 20:0 FFA). A typical negative-ion ESI mass spectrum of a mouse myocardial lipid extract in the presence of a small amount of LiOH (the identical solution used for the acquisition of FIGS. 13B and 13C) displays very abundant FFA molecular species (FIG. 15A).

It has been demonstrated that non-hydroxy and 2-hydroxy subclasses of ceramide molecular species displayed distinct fragmentation patterns in product-ion ESI tandem mass spectra (37). A unique abundant product ion corresponding to the neutral loss of mass 256.2 or 327.3 u is present in the fragmentation pattern of non-hydroxy or 2-hydroxy ceramide molecular species, respectively. Thus, negative-ion neutral loss scannings of mass 256.2 and 327.3 u during direct infusion of crude lipid extracts in the presence of LiOH can be performed to identify non-hydroxy and 2-hydroxy ceramide molecular species in the lipid extracts (37). In addition, a common product ion with identical abundance corresponding to the neutral loss of mass 240.2 u for both subclasses of ceramide is also present in all product-ion mass spectra of ceramides containing N-acyl sphingosine with an 18-carbon homolog. Thus, quantitation of ceramide molecular species from crude extracts of biological samples in comparisons with an internal standard after correction for $^{13}$C isotope effects can be achieved by neutral loss scanning of mass 240.2 u (37). For example, negative-ion ESI tandem mass spectrometry with neutral loss scanning of mass 240.2 u of a mouse myocardial lipid extract in the presence of a small amount of LiOH (the identical solution used for the acquisition of FIGS. 13 and 15A) demonstrates over 10 ceramide molecular species (FIG. 15B) which can be quantified in comparisons to an internal standard (N17:0 ceramide (m/z 550.6)).

Figure 13C:
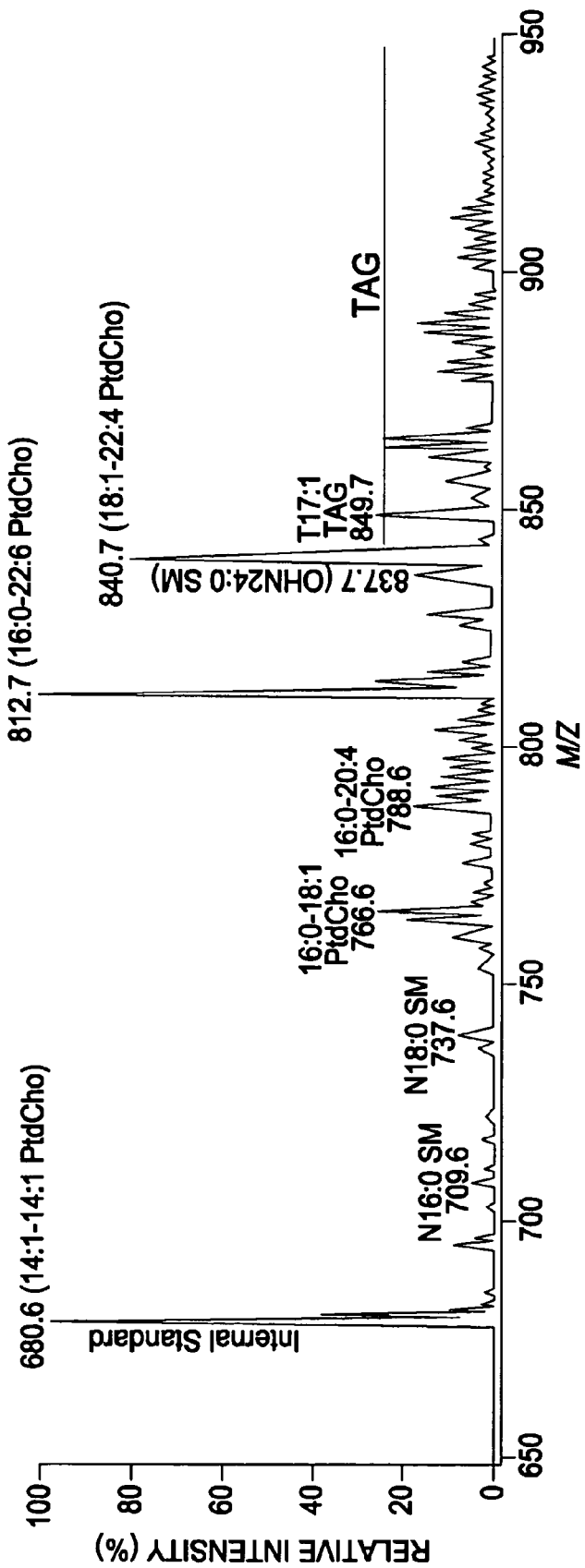
Figure 14:
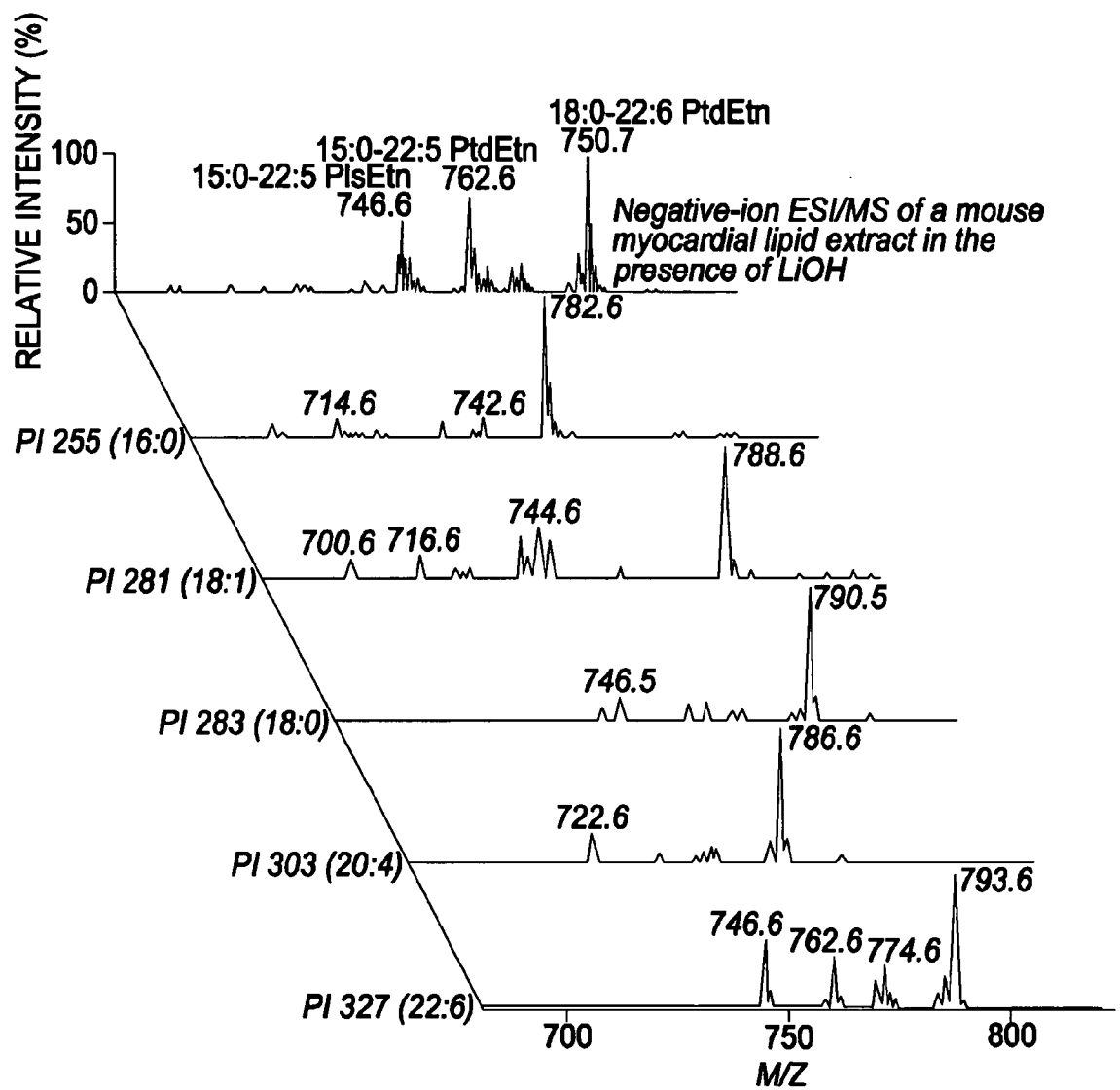
FIG. 14. The two-dimensional fingerprint of ethanolamine glycerophospholipid molecular species in a mouse myocardial lipid extract by negative-ion electrospray ionization tandem mass spectrometry in the precursor-ion mode. The lipid extract is identical to the one described in the legend of FIG. 13 obtained in the presence of LiOH. All precursor-ion (PI) mass spectra displayed are normalized to the base peak in the individual mass spectrum.
Figure 16:
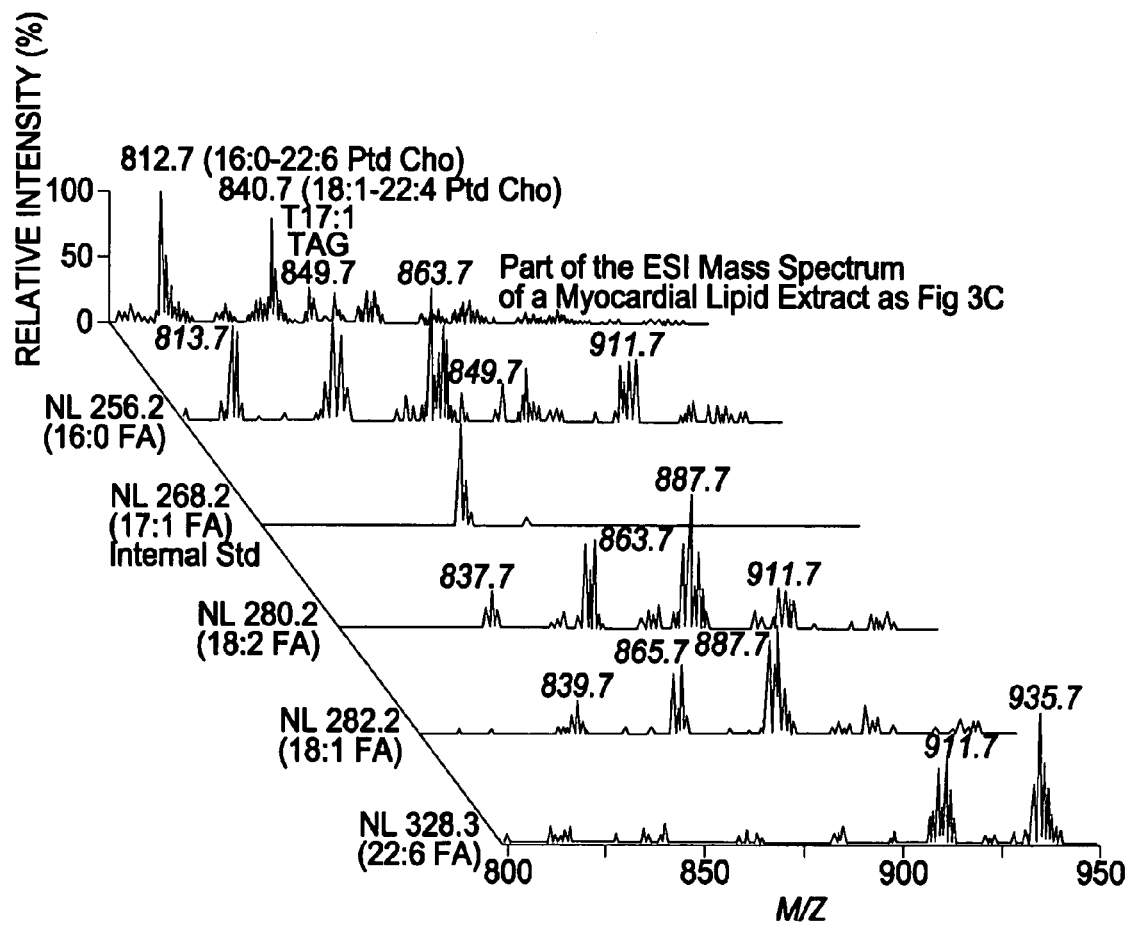
FIG. 16. Two-dimensional fingerprint of triacylglycerol molecular species of a mouse myocardial lipid extract by positive-ion electrospray ionization tandem mass spectrometry. The lipid extract is identical to the one described in the legend of FIG. 13 in the presence of LiOH. All neutral loss (NL) mass spectra displayed are normalized to the base peak in the individual mass spectrum.

Intriguingly, TAG (a class of nonpolar lipids) also show abundant lithiated ions in positive-ion ESI mass spectra of lipid extracts under the ionization conditions employed (FIG. 13C). However, direct TAG quantitation as their lithiated adducts by positive-ion ESI/MS is still confounded by the presence of overlapping peaks from choline glycerophospholipids and the presence of multiple isobaric molecular species in the majority of TAG pseudomolecular ion peaks (FIG. 13C). Accordingly, we have recently exploited the rapid loss of phosphocholine from choline glycerophospholipids in conjunction with neutral-loss scanning of individual fatty acids of TAG to directly quantitate TAG from biological extracts 36). Deconvolution of overlapping and isobaric peaks in the positive-ion ESI mass spectra of lipid extracts by two-dimensional fatty acyl group analyses is accomplished by iterative processing resulting in a detailed molecular species fingerprint of individual TAG molecular species directly from chloroform extracts of biological samples. A typical two-dimensional fingerprint of TAG molecular species of a mouse myocardial lipid extract (as shown in FIG. 13C) demonstrates the lipid constituents (FIG. 16). In this figure, the importance of the rapid loss of phosphocholine from PC and its impact on leaving the TAG molecular species behind for neutral loss analyses of fatty acyl chains is been well demonstrated. For example, the spectrum acquired from neutral loss scanning of 328.3 u (corresponding to 22:6 FFA) displays very low abundant ion peaks corresponding to PC molecular species containing 22:6 while the abundant displayed peaks in the neutral loss spectrum are those from low abundant TAG ion peaks in the MS spectrum. This method readily detects as little as 0.1 pmol of each TAG molecular species from crude lipid extracts and is linear over a 1000-fold dynamic range (36). Therefore, fingerprinting and quantitation of individual TAG molecular species directly from chloroform extracts of biological samples can be achieved with an error of approximately 10% which has been routinely attained in our laboratories (36, 51-53).

While the present invention has been described with reference to what are presently considered to be the preferred examples, it is to be understood that the invention is not limited to the examples herein. Rather the scope of the invention is intended to cover various modifications and equivalent arrangements included within the spirit and scope of the appended claims.

REFERENCES

1. Saudek, C. D., and Eder, H. A. (1979) Lipid metabolism in diabetes mellitus. Am. J. Med. 66, 843-852.
2. Dhalla, M. S., Elimban, V., and Rupp, H. (1992) Paradoxical role of lipid metabolism in heart function and dysfunction. Mol. Cell. Biochem. 116, 3-9.
3. Lee, Y., Hirose, H., Ohneda, M., Johnson, J. H. McGarry, J. D., and Unger, R. H. (1994) β-cell lipotoxicity in the pathogenesis of non-insulin-dependent diabetes mellitus of obese rats: Impairment in adipocyte β-cell relationships. Proc. Natl. Acad. Sci. USA 91, 10878-10882.
4. Unger, R. H. (1995) Lipotoxicity in the pathogenesis of obesity-dependent NIDDM. Diabetes 44, 863-870.
5. Goldberg, I. J. (1996) Lipoprotein lipase and lipolysis: Central roles in lipoprotein metabolism and atherogenesis. J. Lipid Res. 37, 693-707.
6. Lopaschuk, G. D. (1996) Abnormal mechanical function in diabetes: Relationship to altered myocardial carbohydrate/lipid metabolism. Coron. Artery Dis. 7, 116-128.
7. Stanley, W. C., Lopaschuk, G. D., and McCormack, J. G. (1997) Regulation of energy substrate metabolism in the diabetic heart. Cardiovasc. Res. 34, 25-33.
8. Han, X., Abendschein, D. R. Kelley, J. G., and Gross, R. W. (2000) Diabetes-induced changes in specific lipid molecular species in rat myocardium. Biochem. J. 352, 79-89.
9. Innis, S. M. (1993) The colostrum-deprived piglet as a model for study of infant lipid nutrition. J. Nutr. 123, 386-390.
10. Cole, T. G., Klotzsch, S. G., and McNamara, J. R. (1994) Measurement of triacylglyceride concentration. In Laboratory Measurement of Lipids, Lipoproteins and Apolipoproteins (Rifai, N., and Warnick, R., Eds.), pp. 81-90, AACC Press, Washington, DC.
11. Dobson, G., Christie, W. W., and Nikolova-Damyanova, B. (1995) Silver ion chromatography of lipids and fatty acids. J. Chromatogr. B. 671, 197-222.
12. Bartle, K. D., and Clifford, A. A. (1994) Supercritical fluid extraction and chromatography of lipid materials. In Developments in the Analysis of Lipids (Tyman, J. H. P., and Gordon, M. H., Eds.), pp. 1-41, Royal Soc. Chem., Cambridge, UK.
13. Demirbuker, M., Blomberg, L., Olsson, N. U., Bergqvist, M., Herslof, B. G., and Jacobs, F. A. (1992) Characterization of triacylglycerols in the seeds of Aquilegia vulgaris by chromatographic and mass spectrometric methods. Lipids 27, 436-411.
14. Evershed, R. P. (1996) High resolution triacylglycerol mixture analysis using high temperature gas chromatography mass spectrometry with a polarizable stationary phase, negative ion chemical ionization, and mass resolved chromatography. J. Am. Soc. Mass Spectrom 7, 350-361.
15. Lamberto, Z. M., and Saitta, M. (1995) Principal component analysis in fast atom bombardment-mass spectrometry of triacylglycerols in edible oils. J. Am. Oil Chem. Soc. 72, 867-871.
16. Duffin, K. L., Henion, J. D., and Shieh, J. J. (1991) Electrospray and tandem mass spectrometric characterization of acylglycerol mixtures that are dissolved in nonpolar solvents. Anal. Chem. 63, 1781-1788.
17. Cheng, C., Gross, M. L., and Pittenauer, E. (1998) Complete structural elucidation of triacylglycerols by tandem sector mass spectrometry. Anal. Chem. 70, 4417-4426.
18. Myher, J. J., Kuksis, A., Geher, K., Park, P. W., and Diersen-Schede, D. A. (1996) Stereospecific analysis of triacylglycerols rich in long-chain polyunsaturated fatty acids. Lipids 31, 207-215.
19. Byrdwell, W. C., and Emken, E. A. (1995) Analysis of triacylglycerides using atmospheric pressure chemical ionization mass spectrometry. Lipids 30, 173-175.
20. Hsu, F. F., and Turk, J. (1999) Structural characterization of triacylglycerols as lithiated adducts by electrospray ionization mass spectrometry using low-energy collisionally activated dissociation on a triple stage quadruple instrument. J. Am. Soc. Mass Spectrom 10, 587-599.
21. Asbury, G. R., Al-Saad, K., Siems, W. F., Hannan, R. M., and Hill, H. H. (1999) Analysis of triacylglycerols and whole oils by matrix-assisted laser desorption/ionization time of flight mass spectrometry. J. Am. Soc. Mass Spectrom. 10, 983-991.
22. Glenn, K. C., Shieh, J. J., and Laird, D. M. (1992) Characterization of 3T3-L1 storage lipid metabolism: Effect of somatotropin and insulin on specific pathways. Endocrinology 131, 115-1124
23. Fink, L. W., and Gross, R. W. (1984) Modulation of canine myocardial sarcolemmal membrane fluidity by amphiphilic compounds. Circ. Res. 55, 585-594
24. Bligh, E. G., an Dyer, W. J. (1959) A rapid method of total lipid extraction and purification. Can. J. Biochem. Physiol. 37, 911-917
25. Han, X., and Gross, R. W. (1994) Electrospray ionization mass spectroscopic analysis of human erythrocyte plasma membrane phospholipids. Proc. Natl. Acad. Sci. USA 91, 10635-10639
26. Han, X., Gubitosi-Klug, R., A., Collins, B. J., and Gross, R. W. (1996) Alterations in individual molecular species of human platelet phospholipids during thrombin stimulation: Electrospray ionization mass spectrometry-facilitated identification of the boundary conditions for the magnitude and selectivity of thrombin-induced platelet phospholpid hydrolysis. Biochemistry 35, 5822-5832.
27. Han., X., and Gross, R. W. (1995) Structural determination of picomole amounts of phospholipids via electrospray ionization tandem mass spectrometry. J. Am. Soc. Mass Spectrom. 6, 1202-1210

28. B. Brügger, G. Erben, R. Sandhoff, F. T. Wieland, W. D. Lehmann, Quantitative analysis of biological membrane lipids at the low picomole level by nano-electrospray ionization tandem mass spectrometry. Proc. Natl. Acad. Sci. USA 94 (1997) 2339-2344.

29. R. Welti, W. Li, M. Li, Y. Sang, H. Biesiada, H.-E. Zhou, C. B. Rajashekar, T. D. Williams, X. Wang, Profiling membrane lipids in plant stress responses. Role of phospholipase Da in freezing-induced lipid changes in Arabidopsis. J. Biol. Chem. 277 (2002) 31994-32002.

30. T. S. Blom, M. Koivusalo, E. Kuismanen, R. Kostiainen, P. Somerharju, E. Ikonen, Mass spectrometric analysis reveals an increase in plasma membrane polyunsaturated phospholipid species upon cellular cholesterol loading. Biochemistry 40 (2001) 14635-14644.

31. K. Ekroos, I. V. Chernushevich, K. Simons, A. Shevchenko, Quantitative profiling of phospholipids by multiple precursor ion scanning on a hybrid quadrupole time-of flight mass spectrometer. Anal. Chem. 74 (2002) 941-949.

32. H.-Y. Kim, T. C. L. Wang, Y.-C. Ma, Liquid chromatography/mass spectrometry of phospholipids using electrospray ionization. Anal. Chem. 66 (1994) 3977-3982.

33. W. D. Lehmann, M. Koester, G. Erben, D. Keppler, Characterization and quantification of rat bile phosphatidylcholine by electrospray-tandem mass spectrometry. Anal. Biochem. 246 (1997) 102-110.

34. M. Koivusalo, P. Haimi, L. Heikinheimo, R. Kostiainen, P. Somerharju, Quantitative determination of phospholipid compositions by ESI-MS: effects of acyl chain length, unsaturation, and lipid concentration on instrument response. J. Lipid Res. 42 (2001) 663-672.

35. C. J. DeLong, P. R. S. Baker, M. Samuel, Z. Cui, M. J. Thomas, Molecular species composition of rat liver phospholipids by ESI-MS/MS: the effect of chromatography. J. Lipid Res. 42 (2001) 1959-1968.

36. X. Han, R. W. Gross, Quantitative analysis and molecular species fingerprinting of triacylglyceride molecular species directly from lipid extracts of biological samples by electrospray ionization tandem mass spectrometry. Anal. Biochem. 295 (2001) 88-100.

37. X. Han, Characterization and direct quantitation of ceramide molecular species from lipid extracts of biological samples by electrospray ionization tandem mass spectrometry. Anal. Biochem. 302 (2002) 199-212.

38. N. M. Neskovic, D. M. Kostic, Quantitative analysis of rat liver phospholipids by a two-step thin-layer chromatographic procedure. J. Chromagr. 35 (1968) 297-300.

39. J. N. Miceli, W. J. Ferrell, Quantitative distribution of lipids in mouse total liver, mitochondria, and microsomes. Physiol. Chem. Phys. 4 (1972) 131-138.

40. D. Tsambaos, A. Kalofoutis, S. Georgiou, A. Koulocheris, Oral acitretin induces alterations in mouse liver phospholipid composition. In Vivo 6 (1992) 85-87.

41. X. Han, R. W. Gross, Structural determination of lysophospholipid regioisomers by electrospray ionization tandem mass spectroscopy. J. Am. Chem. Soc. 118 (1996) 451-457.

42. P. B. W. Smith, A. P. Snyder, C. S. Harden, Characterization of bacterial phospholipids by electrospray ionization tandem mass spectrometry. Anal. Chem. 67 (1995) 1824-1830.

43. F.-F. Hsu, A. Bohrer, J. Turk, Formation of lithiated adducts of glycerophosphocholine lipids facilitates their identification by electrospray ionization tandem mass spectrometry. J. Am. Soc. Mass Spectrom. 9 (1998) 516-526.

44. F.-F. Hsu, J. Turk, Characterization of phosphatidylinositol, phosphatidylinositol-4-phosphate, and phosphatidylinositol-4,5-bisphosphate by electrospray ionization tandem mass spectrometry: a mechanistic study. J. Am Soc. Mass Spectrom. 11 (2000) 986-999.

45. M. C. Sullards, Analysis of sphingomyelin, glucosylceramide, ceramide, sphingosine, and sphingosine 1-phosphate by tandem mass spectrometry. Methods Enzymol. 312 (2000) 32-45.

46. Kerwin, J. L, Tuininga, A. R. and Ericsson, L. H. (1994) Identification of molecular species of glycerophospholipids and sphingomyelin using electrospray mass spectrometry. J. Lipid Res. 35, 1102-1114.

47. Fridriksson, E. K., Shipkova, P. A., Sheets, E. D., Holowka, D., Baird, B. and McLafferty, F. W. (1999) Quantitative analysis of phospholipids in functionally important membrane domains from RBL-2H3 mast cells using tandem high-resolution mass spectrometry. Biochemistry 38, 8056-8063.

48. Pike, L. J., Han, X., Chung, K.-N. and Gross, R. W. (2002) Lipid rafts are enriched in arachidonic acid and plasmenylethanolamine and their composition is independent of caveolin-1 expression: A quantitative electrospray ionization/mass spectrometric analysis. Biochemistry 41, 2075-2088.

49. Han, X., Cheng, H., Fryer, D. J., Fagan, A. M. and Holtzman, D. M. (2003) Novel role for apolipoprotein E in the central nervous system: Modulation of sulfatide content. J. Biol. Chem. 278, 8043-8051.

50. Ford, D. A., Rosenbloom, K. B. and Gross, R. W. (1992) The primary determinant of rabbit myocardial ethanolamine phosphotransferase substrate selectivity is the covalent nature of the sn-1 aliphatic group of diradyl glycerol acceptors. J. Biol. Chem. 267, 11222-11228.

51. Finck, B. N., Lehman, J. J., Leone, T. C., Welch, M. J., Bennett, M. J., Kovacs, A., Han, X., Gross, R. W., Kozak, R., Lopaschuk, G. D. and Kelly, D. P. (2002) The cardiac phenotype induced by PPAR☐ overexpression mimics that caused by diabetes mellitus. J. Clin. Invest. 109, 121-130.

52. Finck, B. N., Han, X., Courtois, M., Aimond, F., Nerbonne, J. M., Kovacs, A., Gross, R. W. and Kelly, D. P. (2003) A critical role for PPAR☐-mediated lipotoxicity in the pathogenesis of diabetic cardiomyopathy: Modulation of phenotype by dietary fat content. Proc. Natl. Acad. Sci. USA 100, 1226-1231.

53. Listenberger, L., Han, X., Lewis, S. E., Cases, S., Farese Jr., R. V., Ory, D. S. and Schaffer, J. E. (2003) Triglyceride accumulation protects against fatty acid-induced lipotoxicity. Proc. Natl. Acad. Sci. USA 100, 3077-3082.

What is claimed is:

1. A method for the determination of cellular lipid individual molecular species composition of matter in a biological sample, said method comprising:

subjecting the biological sample to lipid extraction to obtain a lipid extract;

subjecting the lipid extract to two dimensional electrospray ionization tandem mass spectrometry (ESI/MS/MS);

generating a two dimensional plot representing molecular ions of the lipid extract on a first axis and at least one of neutral loss scans of fatty acids of the lipid extract and precursor ion scans on a second axis; and comparing peak heights for the molecular ions with that for an internal standard to at least one of identify and quantify the lipid molecular species.

2. A method in accordance with claim 1 wherein the lipid extract is obtained via at least one of a chloroform lipid extraction, a chloroform/methanol extraction, and a butanol extraction.

3. A method in accordance with claim 1 wherein said extraction is of at least one of a blood, serum, tissue, tissue biopsy, feces and urine sample.

4. A method in accordance with claim 1 wherein said biological sample is at least one of a mammalian tissue, a plant tissue, a microbiological sample, and a fungal sample.

5. A method in accordance with claim 4 wherein the mammalian tissue is human tissue and the lipid is at least one of a triacylglyceride, a phospholipid, and any other lipid species contained within biologic membranes.

6. A method in accordance with claim 1 further comprising determining a fingerprint profile of a lipid individual molecular species.

7. A method in accordance with claim 6 wherein said fingerprint profile represents the individual molecular species of a lipid composition of matter.

8. A method in accordance with claim 1 wherein said lipid comprises at least one of phospholipids, fatty acids, fatty amides, eicosanoids, sphingolipids, glycolipids, steroids, ceramides, acylCoA, acylcamitine, acylprotiens, acylpeptides, diglycerides, monoglycerides, anadamide and 2-arachidonyl glycerol or oxidized nitrated or sulfated species therefrom or other derivatives know to those in the field.

9. A method in accordance with claim 8 wherein said phospholipid is selected from the group consisting of choline glycerophospholipids, sphingomeyelin, ethanolamine glycerophospholipids, mono and dimethyl ethanolamine, glycerophospholipds, serine glycerophospholipids, inositol glycerophospholipids, cardiolipin, phosphatidic acid, phosphatidylglycerol, phasphatidylethanol and oxidized derivatives thereof.

10. A method in accordance with claim 9 wherein said choline glycerophospholipids are selected from the group consisting of plasmenycholine, phosphatidylcholine, and plasmanylcholine.

11. A method for the determination of cellular lipid individual molecular species composition of matter directly from a lipid extract of a biological sample, said method comprising:

subjecting said lipid extract to electrospray ionization tandem mass spectrometry;

generating a two dimensional plot of molecular ions of the lipid extract versus at least one of neutral loss scans and precursor ion scans of lipid classes of the lipid extract; and comparing peak heights for the molecular ions with that for an internal standard to identify and/or quantify the lipid molecular species.

12. A method in accordance with claim 11 wherein said lipid extract is obtained via at least one of chloroform extraction, a chloroform/ methanol extraction, and a butanol extraction.

13. A method in accordance with claim 11 wherein said internal standard includes a control sample of lipid molecular species.

14. A method in accordance with claim 11 further comprising at least one of iteratively deconvoluting and normalizing the peak heights for the molecular ions.

15. A method in accordance with claim 11 further comprising deconvoluting the intensity of two dimensional intercept contours of at least one of the neutral loss scans and the precursor ion scans for multidimensional mass spectrometry.

16. A method in accordance with claim 11 wherein said biological sample is at least one of a mammalian and a plant tissue.

17. A method in accordance with claim 16 wherein said mammalian tissue is human tissue.

18. A method in accordance with claim 11 wherein the biological sample is an aqueous human fluid sample subjected to at least one of centrifugation and conventional column chromatography suitable for separation of lipoproteins to resolve lipids into different lipoprotein fractions.

19. A method in accordance with claim 18 wherein the aqueous human fluid sample is at least one of whole blood, blood serum, blood plasma, liver and urine.

20. A method in accordance with claim 19 wherein the lipid extract is obtained by extraction of said biological sample with at least one of chloroform and any other solvent.

* * * * *